US008689647B2

(12) United States Patent
Stein

(10) Patent No.: US 8,689,647 B2
(45) Date of Patent: *Apr. 8, 2014

(54) SENSING MODULE HAVING A PIEZO-RESISTIVE SENSOR FOR ORTHOPEDIC LOAD SENSING INSERT DEVICE

(75) Inventor: Marc Stein, Chandler, AZ (US)

(73) Assignee: Orthosensor Inc., Dania Beach, FL (US)

( * ) Notice: Subject to any disclaimer, the term of this patent is extended or adjusted under 35 U.S.C. 154(b) by 57 days.

This patent is subject to a terminal disclaimer.

(21) Appl. No.: 13/539,476

(22) Filed: Jul. 1, 2012

(65) Prior Publication Data

US 2012/0283600 A1    Nov. 8, 2012

Related U.S. Application Data

(63) Continuation of application No. 12/826,349, filed on Jun. 29, 2010, now Pat. No. 8,245,583.

(51) Int. Cl.
*G01L 1/04* (2006.01)
(52) U.S. Cl.
USPC ........................................ 73/862.636; 73/777
(58) Field of Classification Search
USPC ..................... 73/760, 777, 862.636
See application file for complete search history.

(56) References Cited

U.S. PATENT DOCUMENTS

| | | | |
|---|---|---|---|
| 4,066,082 A | 1/1978 | Arcan et al. | |
| 4,899,761 A | 2/1990 | Brown et al. | |
| 5,470,354 A | 11/1995 | Hershberger et al. | |
| 5,669,914 A | 9/1997 | Eckhoff | |
| 6,739,068 B1 | 5/2004 | Rinner | |
| 6,796,988 B2 | 9/2004 | Melkent et al. | |
| 7,153,281 B2 | 12/2006 | Holmes | |
| 7,195,645 B2 | 3/2007 | Disilvestro et al. | |
| 7,384,403 B2 | 6/2008 | Sherman | |
| 7,559,951 B2 | 7/2009 | DiSilvestro et al. | |
| 7,575,602 B2 | 8/2009 | Amirouche et al. | |
| 7,615,055 B2 | 11/2009 | DiSilvestro | |
| 2003/0036764 A1 | 2/2003 | Hamada | |
| 2003/0187351 A1 | 10/2003 | Franck et al. | |
| 2004/0019382 A1 | 1/2004 | Amirouche et al. | |
| 2004/0064073 A1 | 4/2004 | Heldreth | |
| 2004/0064191 A1 | 4/2004 | Wasielewski | |
| 2004/0152970 A1 | 8/2004 | Hunter et al. | |
| 2005/0234555 A1 | 10/2005 | Sutton et al. | |
| 2007/0233267 A1 | 10/2007 | Amirouche et al. | |
| 2008/0082118 A1 | 4/2008 | Edidin et al. | |
| 2008/0228195 A1 | 9/2008 | Von Jako et al. | |
| 2009/0005708 A1 | 1/2009 | Johanson et al. | |
| 2010/0010494 A1 | 1/2010 | Quirno | |

(Continued)

*Primary Examiner* — Max Noori

(57) ABSTRACT

A sensing insert device (100) is disclosed for measuring a parameter of the muscular-skeletal system. The sensing insert device (100) can be temporary or permanent. Used intra-operatively, the sensing insert device (100) comprises an insert dock (202) and a sensing module (200). The sensing module (200) is a self-contained encapsulated measurement device having at least one contacting surface that couples to the muscular-skeletal system. The sensing module (200) comprises one or more sensing assemblages, electronic circuitry (307), an antenna (2302), and communication circuitry (320). The sensing assemblages are between a top plate (1502) and a bottom plate (1504) in a sensing platform (121). The sensing assemblages comprise a load disc (2004) and a piezo-resistive sensor (2002) to measure the parameter. An elastic support structure or springs (1108) is coupled between the top plate (1502) and the bottom plate (1504) to prevent cantilevering of a surface.

20 Claims, 24 Drawing Sheets

(56) References Cited

U.S. PATENT DOCUMENTS

| | | |
|---|---|---|
| 2010/0022874 A1 | 1/2010 | Wang et al. |
| 2011/0166491 A1* | 7/2011 | Sankai .......................... 601/84 |
| 2013/0079669 A1* | 3/2013 | Stein et al. .................... 600/587 |
| 2013/0079672 A1* | 3/2013 | Stein et al. .................... 600/587 |

* cited by examiner

DATA PACKET

1300

1400

SENSING MODULE HAVING A PIEZO-RESISTIVE SENSOR FOR ORTHOPEDIC LOAD SENSING INSERT DEVICE

CROSS-REFERENCE TO RELATED APPLICATIONS

This application is a continuation of application Ser. No. 12/826,349 filed on Jun. 29, 2010 the content of which is hereby incorporated by reference in its entirety.

FIELD

The present invention pertains generally to a joint prosthesis, and particularly to methods and devices for assessing and determining proper alignment and placement of an implant component or components during joint reconstructive surgery and long-term implantation.

BACKGROUND

The skeletal system of a mammal is subject to variations among species. Further changes can occur due to environmental factors, degradation through use, and aging. An orthopedic joint of the skeletal system typically comprises two or more bones that move in relation to one another. Movement is enabled by muscle tissue and tendons attached to the skeletal system of the joint. Ligaments hold and stabilize the one or more joint bones positionally. Cartilage is a wear surface that prevents bone-to-bone contact, distributes load, and lowers friction.

There has been substantial growth in the repair of the human skeletal system. In general, orthopedic joints have evolved using information from simulations, mechanical prototypes, and patient data that is collected and used to initiate improved designs. Similarly, the tools being used for orthopedic surgery have been refined over the years but have not changed substantially. Thus, the basic procedure for replacement of an orthopedic joint has been standardized to meet the general needs of a wide distribution of the population. Although the tools, procedure, and artificial joint meet a general need, each replacement procedure is subject to significant variation from patient to patient. The correction of these individual variations relies on the skill of the surgeon to adapt and fit the replacement joint using the available tools to the specific circumstance.

BRIEF DESCRIPTION OF THE DRAWINGS

Various features of the system are set forth with particularity in the appended claims. The embodiments herein, can be understood by reference to the following description, taken in conjunction with the accompanying drawings, in which:

DETAILED DESCRIPTION

Figure 1:
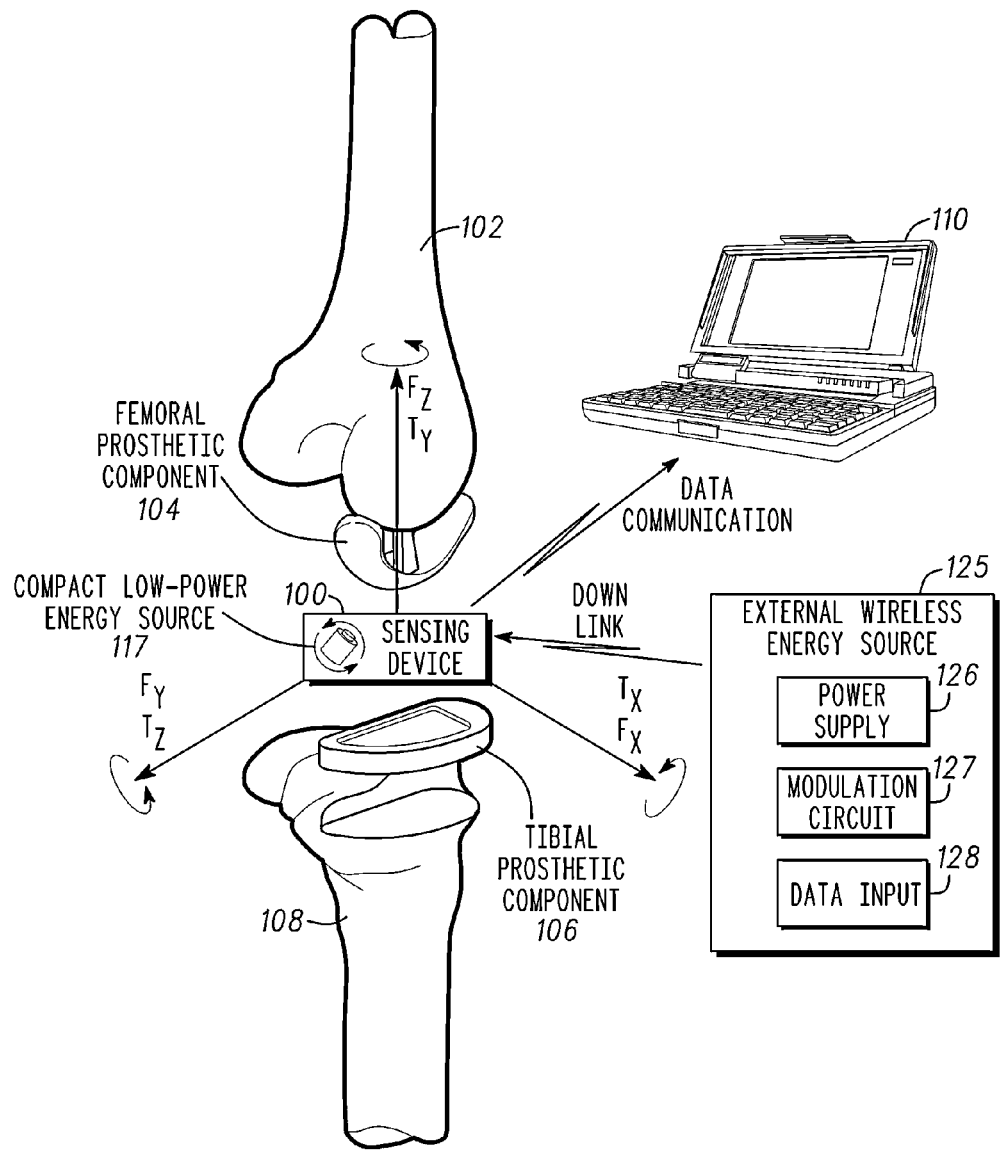
FIG. 1 is an illustration of an application of sensing insert device in accordance with an exemplary embodiment.

Embodiments of the invention are broadly directed to measurement of physical parameters. Many physical parameters of interest within physical systems or bodies can be measured by evaluating changes in the characteristics of energy waves or pulses. As one example, changes in the transit time or shape of an energy wave or pulse propagating through a changing medium can be measured to determine the forces acting on the medium and causing the changes. The propagation velocity of the energy waves or pulses in the medium is affected by physical changes in of the medium. The physical parameter or parameters of interest can include, but are not limited to, measurement of load, force, pressure, displacement, density, viscosity, localized temperature. These parameters can be evaluated by measuring changes in the propagation time of energy pulses or waves relative to orientation, alignment, direction, or position as well as movement, rotation, or acceleration along an axis or combination of axes by wireless sensing modules or devices positioned on or within a body, instrument, appliance, vehicle, equipment, or other physical system.

In all of the examples illustrated and discussed herein, any specific materials, temperatures, times, energies etc. . . . for process steps or specific structure implementations should be interpreted to be illustrative only and non-limiting. Processes, techniques, apparatus, and materials as known by one of ordinary skill in the art may not be discussed in detail but are intended to be part of an enabling description where appropriate.

Note that similar reference numerals and letters refer to similar items in the following figures. In some cases, numbers from prior illustrations will not be placed on subsequent figures for purposes of clarity. In general, it should be assumed that structures not identified in a figure are the same as previous prior figures.

In the present invention these parameters are measured with an integrated wireless sensing module or device comprising an i) encapsulating structure that supports sensors and contacting surfaces and ii) an electronic assemblage that integrates a power supply, sensing elements, ultrasound resonator or resonators or transducer or transducers and ultrasound waveguide or waveguides, biasing spring or springs or other form of elastic members, an accelerometer, antennas and electronic circuitry that processes measurement data as well as controls all operations of energy conversion, propagation, and detection and wireless communications. The wireless sensing module or device can be positioned on or within, or engaged with, or attached or affixed to or within, a wide range of physical systems including, but not limited to instruments, appliances, vehicles, equipments, or other physical systems as well as animal and human bodies, for sensing and communicating parameters of interest in real time.

FIG. 1 is an illustration of an application of sensing insert device 100 in accordance with an exemplary embodiment. The medical device incorporates a loop antenna 107. In this example, the medical device can intra-operatively assess a load on the prosthetic knee components (implant) and collect load data for real-time viewing of the load over various applied loads and angles of flexion. By way of the loop antenna 107, a compact low-power energy source 117, and associated transceiver electronics, the sensing insert device 100 can transmit measured load data to a receiver for permitting visualization of the level and distribution of load at various points on the prosthetic components. This can aid the surgeon in making any adjustments needed to achieve optimal joint balancing. The insert device 100 further includes a compact low-power energy source 117.

In general, device 100 has at least one contacting surface that couples to the muscular-skeletal system. As shown, a first and a second contacting surface respectively couple to a femoral prosthetic component 104 and a tibial prosthetic component 106. Device 100 is designed to be used in the normal flow of an orthopedic surgical procedure without special procedures, equipment, or components. Typically, one or more natural components of the muscular-skeletal system are replaced when joint functionality substantially reduces a patient quality of life. A joint replacement is a common procedure in later life because it is prone to wear over time, can be damaged during physical activity, or by accident.

A joint of the muscular-skeletal system provides movement of bones in relation to one another that can comprise angular and rotational motion. The joint can be subjected to loading and torque throughout the range of motion. The joint typically comprises two bones that move in relation to one another with a low friction flexible connective tissue such as cartilage between the bones. The joint also generates a natural lubricant that works in conjunction with the cartilage to aid in ease of movement. Sensing insert device 100 mimics the natural structure between the bones of the joint. Insert device 100 has a contacting surface on which a bone or a prosthetic component can moveably couple. A knee joint is disclosed for illustrative purposes but sensing insert device 100 is applicable to other joints of the muscular-skeletal system. For example, the hip, spine, and shoulder have similar structures comprising two or more bones that move in relation to one another. In general, insert device 100 can be used between two or more bones allowing movement of the bones during measurement or maintaining the bones in a fixed position.

The load sensor insert device 100 and the receiver station 110 forms a communication system for conveying data via secure wireless transmission within a broadcasting range over short distances on the order of a few meters to protect against any form of unauthorized or accidental query. In one embodiment, the transmission range is five meters or less which is approximately a dimension of an operating room. In practice, it can be a shorter distance 1-2 meters to transmit to a display outside the sterile field. The transmit distance will be even shorter when device 100 is used in a prosthetic implanted component. Transmission occurs through the skin of the patient and is likely limited to less than 0.5 meters. A combination of cyclic redundancy checks and a high repetition rate of transmission during data capture permits discarding of corrupted data without materially affecting display of data In the illustration, a surgical procedure is performed to place a femoral prosthetic component 104 onto a prepared distal end of the femur 102. Similarly, a tibial prosthetic component 106 is placed to a prepared proximal end of the tibia 108. The tibial prosthetic component 106 can be a tray or plate affixed to a planarized proximal end of the tibia 108. The sensing insert device 100 is a third prosthetic component that is placed between the plate of the tibial prosthetic component 106 and the femoral prosthetic component 104. The three prosthetic components enable the prostheses to emulate the functioning of a natural knee joint. In one embodiment, sensing insert device 100 is used during surgery and replaced with a final insert after quantitative measurements are taken to ensure optimal fit, balance, and loading of the prosthesis.

In one embodiment, sensing insert device 100 is a mechanical replica of a final insert. In other words, sensing insert device 100 has substantially equal dimensions to the final insert. The substantially equal dimensions ensure that the final insert when placed in the reconstructed joint will have similar loading and balance as that measured by sensing insert device 100 during the trial phase of the surgery. Moreover, passive trial inserts are commonly used during surgery to determine the appropriate final insert. Thus, the procedure remains the same. It can measure loads at various points (or locations) on the femoral prosthetic component 104 and transmit the measured data to a receiving station 110 by way of an integrated loop antenna 107. The receiving station 110 can include data processing, storage, or display, or combination thereof and provide real time graphical representation of the level and distribution of the load.

As one example, the sensing insert device 100 can measure forces (Fx, Fy, and Fz) with corresponding locations and torques (e.g. Tx, Ty, and Tz) on the femoral prosthetic component 104 and the tibial prosthetic component 106. It can then transmit this data to the receiving station 110 to provide real-time visualization for assisting the surgeon in identifying any adjustments needed to achieve optimal joint balancing.

In a further example, an external wireless energy source 125 can be placed in proximity to the medical sensing device 100 to initiate a wireless power recharging operation. As an example, the external wireless energy source 125 generates energy transmissions that are wirelessly directed to the medical sensing device 100 and received as energy waves via resonant inductive coupling. The external wireless energy source 125 can modulate a power signal generating the energy transmissions to convey downlink data that is then demodulated from the energy waves at the medical sensing device 100. As described above, the sensing insert device 100 is a sensing insert device 100 suitable for use in knee joint replacement surgery. The external wireless energy source 125 can be used to power the sensing insert device 100 during the surgical procedure or thereafter when the surgery is complete and the sensing insert device 100 is implanted for long-term use. The method can also be used to provide power and communication where the sensing insert device 100 is in a final insert that is part of the final prosthesis implanted in the patient.

In one system embodiment, the sensing insert device 100 transmits measured parameter data to a receiver 110 via one-way data communication over the up-link channel for permitting visualization of the level and distribution of the parameter at various points on the prosthetic components. This, combined with cyclic redundancy check error checking, provides high security and protection against any form of unauthorized or accidental interference with a minimum of added circuitry and components. This can aid the surgeon in making any adjustments needed to optimize the installation. In addition to transmitting one-way data communications over the up-link channel to the receiver station 110, the sensing insert device 100 can receive downlink data from the external wireless energy source 125 during the wireless power recharging operation. The downlink data can include component information, such as a serial number, or control information, for controlling operation of the sensing insert device 100. This data can then be uploaded to the receiving system 110 upon request via the one-way up-link channel, in effect providing two-way data communications over separate channels.

Separating uplink and downlink telemetry eliminates the need for transmit-receive circuitry within the sensing insert device 100. Two unidirectional telemetry channels operating on different frequencies or with different forms of energy enables simultaneous up and downlink telemetry. Modulating energy emissions from the external wireless energy source 125 as a carrier for instructions achieves these benefits with a minimum of additional circuitry and components by leveraging existing circuitry and antenna, induction loop, or piezoelectric components on the load sensor insert device 100. The frequencies of operation of the up and downlink telemetry channels can also be selected and optimized to interface with other devices, instruments, or equipment as needed. Separating uplink and downlink telemetry also enables addition of downlink telemetry without altering or upgrading existing chip-set telemetry for the one-way transmit. That is, existing chip-set telemetry can be used for encoding and packaging data and error checking without modification, yet remain communicatively coupled to the separate wireless power down-link telemetry operation for download operations herein contemplated.

As shown, the wireless energy source 125 can include a power supply 126, a modulation circuit 127, and a data input 128. The power supply 126 can be a battery, a charging device, a capacitor, a power connection, or other energy source for generating wireless power signals to power the sensing insert device 100. The external wireless energy source can transmit energy in the form of, but not limited to, electromagnetic induction, or other electromagnetic or ultrasound emissions. In at least one exemplary embodiment, the wireless energy source 125 includes a coil to electromagnetically couple with an induction coil in sensing device 100 when placed in close proximity. The data input 128 can be a user interface component (e.g., keyboard, keypad, or touchscreen) that receives input information (e.g., serial number, control codes) to be downloaded to the load sensor insert device 100. The data input 128 can also be an interface or port to receive the input information from another data source, such as from a computer via a wired or wireless connection (e.g., USB, IEEE802.16, etc.). The modulation circuitry 127 can modulate the input information onto the power signals generated by the power supply 126.

Figure 2:
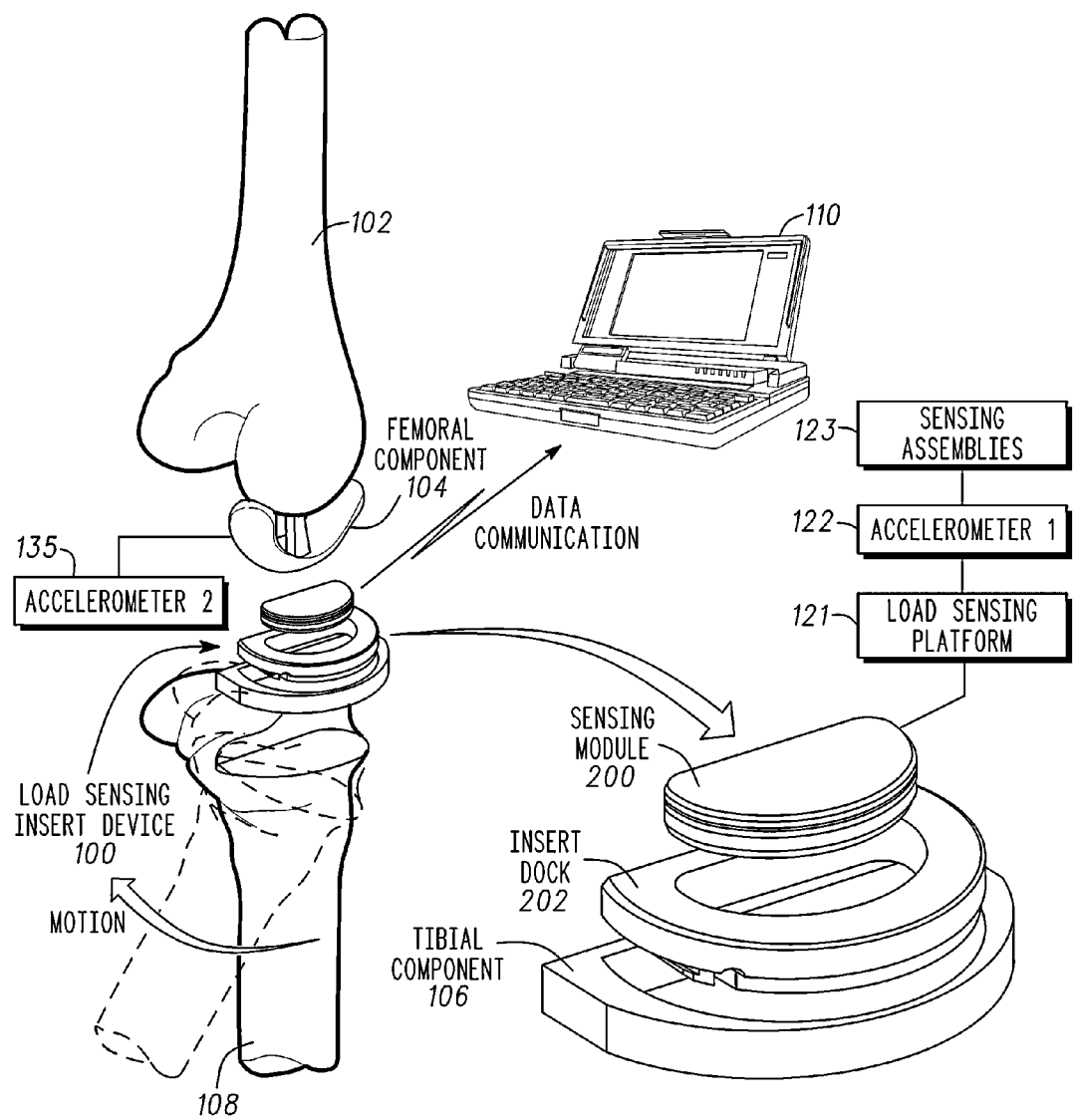
FIG. 2 is an illustration of a sensing insert device placed in a joint of the muscular-skeletal system for measuring a parameter in accordance with an exemplary embodiment.

FIG. 2 is an illustration of a sensing insert device 100 placed in a joint of the muscular-skeletal system for measuring a parameter in accordance with an exemplary embodiment. In particular, sensing insert device 100 is placed in contact between a femur 102 and a tibia 108 for measuring a parameter. In the example, a force, pressure, or load is being measured. The device 100 in this example can intra-operatively assess a load on prosthetic components during the surgical procedure. As mentioned previously, sensing insert device 100 collects data for real-time viewing of the load forces over various applied loads and angles of flexion. It can measure the level and distribution of load at various points on the prosthetic component and transmit the measured load data by way data communication to a receiver station 110 for permitting visualization. This can aid the surgeon in making any adjustments needed to achieve optimal joint balancing.

A proximal end of tibia 108 is prepared to receive tibial prosthetic component 106. Tibial prosthetic component 106 is a support structure that is fastened to the proximal end of the tibia and is usually made of a metal or metal alloy. The tibial prosthetic component 106 also retains the insert in a fixed position with respect to tibia 108. Similarly, a distal end of femur 102 is prepared to receive femoral prosthetic component 104. The femoral prosthetic component 104 is generally shaped to have an outer condylar articulating surface. The preparation of femur 102 and tibia 108 is aligned to the mechanical axis of the leg. The sensing insert device 100 provides a concave or flat surface against which the outer condylar articulating surface of the femoral prosthetic component 104 rides relative to the tibia prosthetic component 106. In particular, the top surface of the sensing module 200 faces the condylar articulating surface of the femoral prosthetic component 104, and the bottom surface of the insert dock 202 faces the top surface of the tibial prosthetic component 106.

A final insert is subsequently fitted between femoral prosthetic component 104 and tibial prosthetic component 106 that has a bearing surface that couples to femoral component 104 allowing the leg a natural range of motion. The final insert is has a wear surface that is typically made of a low friction polymer material. Ideally, the prosthesis has an appropriate loading, alignment, and balance that mimics the natural leg and maximizes the life of the artificial components. It should be noted that sensing module 200 can be placed a final insert and operated similarly as disclosed herein. The sensing module 200 can be used to periodically monitor status of the permanent joint.

The sensing insert device 100 is used to measure, adjust, and test the reconstructed joint prior to installing the final insert. As mentioned previously, the sensing insert device 100 is inserted between the femur 102 and tibia 108. The condyle surface of femoral component 104 contacts a major surface of device 100. The major surface of device 100 approximates a surface of a final insert. Tibial prosthetic component 106 can include a cavity or tray on the major surface that receives and retains the insert dock 202 and a sensing module 200 during a measurement process. Each insert dock 202 has an opening to receive the sensing module 200. In one embodiment, the insert dock 202 can be of different sizes and shapes but each accepts the same sensing module 200. It should be noted that sensing insert device 100 is coupled to and provides measurement data in conjunction with other implanted prosthetic components. In other words, the prosthetic components are the permanent installed components of the patient.

Insert dock 202 is provided in different sizes and shapes. Insert dock 202 can comprise many different sizes and shapes to interface appropriately with different manufacturer prosthetic components. Prosthetic components are made in different sizes to accommodate anatomical differences over a wide population range. Similarly, insert dock 202 is designed for different prosthetic sizes manufactured by the same company. In at least one embodiment, multiple docks of different dimensions are provided for a surgery. In general, the docks are selected having a major surface that fit a corresponding major surface of the tibial prosthetic component 106. More than one dock can be provided each having a different height or thickness. The thickness of the final insert is determined by the surgical cuts to the muscular-skeletal system and measurements provided by sensing module 200. The surgeon selects dock 202 based on the gap between the femur and tibial cuts. The surgeon inserts the sensing module 200 in an opening of the selected dock. The selected dock 202 and sensing module 200 are then inserted in the knee joint to interact with the final femoral and tibial prosthetic components. The surgeon may try two or more insert docks 202 of different thicknesses (or height) before making a final decision. Each trial by the surgeon can include modifications to the joint and tissue. In one embodiment, sensing insert device 100 selected by the surgeon has substantial equal dimensions to the final insert used. The insert dock 202 allows standardization on a single sensing module 200 for different prosthetic platforms. Thus, the sensing module 200 is common to the different insert docks 202 allowing improved quality, reliability, and performance.

In one embodiment, one or more insert docks 202 are used to measure, a force, pressure or load in one or more compartments of the knee having the selected predetermined height or thickness. The surgeon determines an appropriate thickness for the final insert that yields an optimal loading and balance. In general, the absolute loading over the range of motion is kept within a predetermined range. The insert dock 202 and sensing module 200 can be removed from the joint if the absolute loading is found to be above or below the predetermined range. The sensing module 200 is removed from the dock 202 and another selected having a different height. The sensing module 200 is reused and placed in the newly selected dock 202 having a different height or thickness. The dock 202 is then inserted into the knee joint. Measurements are taken to determine if the force, pressure, or load applied by the knee is within the predetermined range.

Once the measurements indicate that the measured loading is within the predetermined range, soft tissue tensioning can be used to adjust the absolute loading. The knee balance can also be adjusted within a predetermined range if a total knee reconstruction is being performed and a sensing module 202 is used in each compartment. The position or location where the applied force, pressure, or loading occurs can also be measured by sensing module 200 allowing adjustment over the range of motion. Tibial prosthetic component 106 and device 100 have a combined thickness that represents a combined thickness of tibial prosthetic component 106 and a final (or chronic) insert of the knee joint. Thus, the final insert thickness or depth is chosen based on the trial performed using device 100. Typically, the final insert thickness is identical to the device 100 to maintain the measured loading and balance. In one embodiment, sensing module 200 and insert docks 202 are disposed of after surgery. Alternatively, the sensing module 200 and insert docks 202 can be cleaned, sterilized, and packaged for reuse.

The prosthesis incorporating device 100 emulates the function of a natural knee joint. Device 100 can measure loads or other parameters at various points throughout the range of motion. Data from device 100 is transmitted to a receiving station 110 via wired or wireless communications. In one embodiment, the surgeon can view the transmitted information on a display. The affect of adjustments made by the surgeon can be viewed in real time with the measurements provided by sensing module 200. The dock 202 and sensing module 200 is removed after the measurements indicate that the force, pressure, or loading is correct, the knee is in balance, and the contact to the insert is centered throughout the range of motion. The final insert is then installed. The final insert will have substantially equal dimensions as the trial insert thereby having similar loadings, balance, and centering. In one embodiment, the final insert includes a sensing module 200 for providing parameter measurement data on the joint throughout its useable life.

In a first embodiment, device 100 is a disposable system. Device 100 can be disposed of after using the sensing insert device 100 to optimally fit the joint implant. Device 100 is a low cost disposable system that reduces capital costs, operating costs, facilitates rapid adoption of quantitative measurement, and initiates evidentiary based orthopedic medicine. In a second embodiment, a methodology can be put in place to clean and sterilize device 100 for reuse. In a third embodiment, device 100 can be incorporated in a tool instead of being a component of the replacement joint. The tool can be disposable or be cleaned and sterilized for reuse. In a fourth embodiment, device 100 can be a permanent component of the replacement joint. Device 100 can be used to provide both short term and long term post-operative data on the implanted joint. In a fifth embodiment, device 100 can be coupled to the muscular-skeletal system. In all of the embodiments, receiving station 110 can include data processing, storage, or display, or combination thereof and provide real time graphical representation of the level and distribution of the load. Receiving station 110 can record and provide accounting information of device 100 to an appropriate authority.

The sensing insert device 100, in one embodiment, comprises a load sensing platform 121, an accelerometer 122, and sensing assemblies 123. This permits the sensing device 100 to assess a total load on the prosthetic components when it is being moved. The system accounts for forces due to gravity and motion. In one embodiment, load sensing platform 121 includes two or more load bearing surfaces, at least one energy transducer, at least one compressible energy propagating structure, and at least one member for elastic support. The accelerometer 122 can measure acceleration. Acceleration can occur when the sensing device 100 is moved or put in motion. Accelerometer 122 can sense orientation, vibration, and impact. In another embodiment, the femoral component 104 can similarly include an accelerometer 135, which by way of a communication interface to the sensing insert device 100, can provide reference position and acceleration data to determine an exact angular relationship between the femur and tibia. The sensing assemblies 123 can reveal changes in length or compression of the energy propagating structure or structures by way of the energy transducer or transducers. Together the load sensing platform 121, accelerometer 122 (and in certain cases accelerometer 135), and sensing assemblies 123 measure force or pressure external to the load sensing platform 121 or displacement produced by contact with the prosthetic components.

In at least one exemplary embodiment, an energy pulse is directed within one or more waveguides in device 100 by way of pulse mode operations and pulse shaping. The waveguide is a conduit that directs the energy pulse in a predetermined direction. The energy pulse is typically confined within the waveguide. In one embodiment, the waveguide comprises a polymer material. For example, urethane or polyethylene are polymers suitable for forming a waveguide. The polymer waveguide can be compressed and has little or no hysteresis in the system. Alternatively, the energy pulse can be directed through the muscular-skeletal system. In one embodiment, the energy pulse is directed through bone of the muscular-skeletal system to measure bone density. A transit time of an energy pulse is related to the material properties of a medium through which it traverses. This relationship is used to generate accurate measurements of parameters such as distance, weight, strain, pressure, wear, vibration, viscosity, and density to name but a few.

Incorporating data from the accelerometer 122 with data from the other sensing components 121 and 123 assures accurate measurement of the applied load, force, pressure, or displacement by enabling computation of adjustments to offset this external motion. This capability can be required in situations wherein the body, instrument, appliance, vehicle, equipment, or other physical system, is itself operating or moving during sensing of load, pressure, or displacement. This capability can also be required in situations wherein the body, instrument, appliance, vehicle, equipment, or other physical system, is causing the portion of the body, instrument, appliance, vehicle, equipment, or other physical system being measured to be in motion during sensing of load, pressure, or displacement.

The accelerometer 122 can operate singly, as an integrated unit with the load sensing platform 121, and/or as an integrated unit with the sensing assemblies 123. Integrating one or more accelerometers 122 within the sensing assemblages 123 to determine position, attitude, movement, or acceleration of sensing assemblages 123 enables augmentation of presentation of data to accurately identify, but not limited to, orientation or spatial distribution of load, force, pressure, displacement, density, or viscosity, or localized temperature by controlling the load and position sensing assemblages to measure the parameter or parameters of interest relative to specific orientation, alignment, direction, or position as well as movement, rotation, or acceleration along any axis or combination of axes. Measurement of the parameter or parameters of interest may also be made relative to the earth's surface and thus enable computation and presentation of spatial distributions of the measured parameter or parameters relative to this frame of reference.

In one embodiment, the accelerometer 122 includes direct current (DC) sensitivity to measure static gravitational pull with load and position sensing assemblages to enable capture of, but not limited to, distributions of load, force, pressure, displacement, movement, rotation, or acceleration by controlling the sensing assemblies to measure the parameter or parameters of interest relative to orientations with respect to the earths surface or center and thus enable computation and presentation of spatial distributions of the measured parameter or parameters relative to this frame of reference.

Embodiments of device 100 are broadly directed to measurement of physical parameters, and more particularly, to evaluating changes in the transit time of a pulsed energy wave propagating through a medium. In-situ measurements during orthopedic joint implant surgery would be of substantial benefit to verify an implant is in balance and under appropriate loading or tension. In one embodiment, the instrument is similar to and operates familiarly with other instruments currently used by surgeons. This will increase acceptance and reduce the adoption cycle for a new technology. The measurements will allow the surgeon to ensure that the implanted components are installed within predetermined ranges that maximize the working life of the joint prosthesis and reduce costly revisions. Providing quantitative measurement and assessment of the procedure using real-time data will produce results that are more consistent. A further issue is that there is little or no implant data generated from the implant surgery, post-operatively, and long term. Device 100 can provide implant status data to the orthopedic manufacturers and surgeons. Moreover, data generated by direct measurement of the implanted joint itself would greatly improve the knowledge of implanted joint operation and joint wear thereby leading to improved design and materials.

As mentioned previously, device 100 can be used for other joint surgeries; it is not limited to knee replacement implant or implants. Moreover, device 100 is not limited to trial measurements. Device 100 can be incorporated into the final joint system to provide data post-operatively to determine if the implanted joint is functioning correctly. Early determination of a problem using device 100 can reduce catastrophic failure of the joint by bringing awareness to a problem that the patient cannot detect. The problem can often be rectified with a minimal invasive procedure at lower cost and stress to the patient. Similarly, longer term monitoring of the joint can determine wear or misalignment that if detected early can be adjusted for optimal life or replacement of a wear surface with minimal surgery thereby extending the life of the implant. In general, device 100 can be shaped such that it can be placed or engaged or affixed to or within load bearing surfaces used in many orthopedic applications (or used in any orthopedic application) related to the musculoskeletal system, joints, and tools associated therewith. Device 100 can provide information on a combination of one or more performance parameters of interest such as wear, stress, kinematics, kinetics, fixation strength, ligament balance, anatomical fit and balance.

Figure 3:
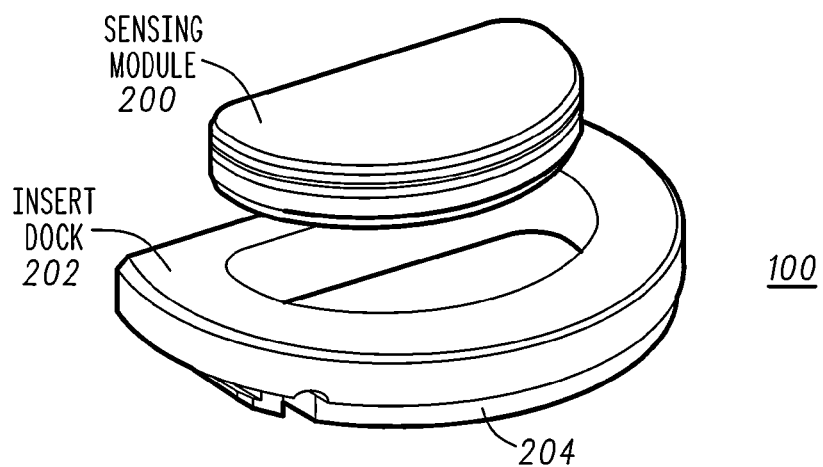
FIG. 3 is a perspective view of a medical sensing platform comprising an encapsulating enclosure in accordance with one embodiment.

FIG. 3 is a perspective view of a medical sensing platform comprising an encapsulating enclosure in accordance with one embodiment. In general, parameters of the muscular-skeletal system can be measured with a sensing module 200 that in one embodiment is an integral part of a complete sensing insert device 100. The sensing module 200 is a self-contained sensor within an encapsulating enclosure that integrates sensing assemblages, an electronic assemblage that couples to the sensing assemblages, a power source, signal processing, and wireless communication. All components required for the measurement are contained in the sensing module 200. The sensing module 200 has at least one contacting surface for coupling to the muscular-skeletal system. A parameter of the muscular-skeletal system is applied to the contact surfaces to be measured by the one or more sensing assemblages therein. As will be disclosed in further detail herein, the sensing module 200 is part of a system that allows intra-operative and post-operative sensing of a joint of the muscular-skeletal system. More specifically, sensing module 200 is placed within a temporary or permanent prosthetic component that has a similar form factor as the passive prosthetic component currently being used. This has a benefit of rapid adoption because the sensing platform is inserted identically to the commonly used passive component but can provide much needed quantitative measurements with little or no procedural changes.

As shown, the sensing insert device 100 comprises an insert dock 202 and the sensing module 200. Sensing insert device 100 is a non-permanent or temporary measurement device that is used intra-operatively to provide quantitative data related to the installation of prosthetic components such as in joint replacement surgery. The combination of the insert dock 202 and sensing module 202 has a form factor substantially equal to a final insert device. The final insert device can be a passive component or sensored incorporating sensing module 200. The substantially equal form factor of sensing insert device 100 results in no extraneous structures in the surgical field that can interfere with the procedure. For example, a final insert device is designed to mimic the function of the natural component it is replacing. The final insert device allows natural movement of the muscular-skeletal system and does not interfere with ligaments, tendons, tissue, muscles, and other components of the muscular-skeletal system. Similarly, sensing insert device 100 allows exposure of the surgical field around the joint by having the similar form factor as the final insert thereby allowing the surgeon to make adjustments during the installation in a natural setting with quantitative measurements to support the modifications.

In one embodiment, insert dock 202 is an adaptor. Insert dock 202 is made in different sizes. In general, prosthetic components are manufactured in different sizes to accommodate variation in the muscular-skeletal system from person to person. In the example, the size of insert dock 202 is chosen to mate with the selected prosthetic implant components. In particular, a feature 204 aligns with and retains insert dock 202 in a fixed position to a prosthetic or natural component of the muscular-skeletal system. The insert dock 202 is a passive component having an opening for receiving sensing module 200. The opening is positioned to place the contacting surfaces in a proper orientation to measure the parameter when used in conjunction with other prosthetic components. The insert dock 202 as an adaptor can be manufactured at low cost. Moreover, insert dock 202 can be formed for adapting to different prosthetic manufacturers thereby increasing system flexibility. This allows a standard sensing module 200 to be provided but customized for appropriate size and dimensions through dock 202 for the specific application and manufacturer component.

The one or more sensing assemblages within sensing module 200 couple to the contacting surfaces of sensing module 200 for receiving the applied parameter of the muscular-skeletal system. In one embodiment, a sensing assemblage comprises one or more energy transducers coupled to an elastic structure. The elastic structure allows the propagation of energy waves. The forms of energy propagated through the elastic energy propagating structures may include, but is not limited to, sound, ultrasound, or electromagnetic radiation including radio frequency, infrared, or light. A change in the parameter applied to the contacting surfaces results in a change a dimension of the elastic structure. The dimension of the elastic structure can be measured precisely using continuous wave, pulsed, or pulsed echo measurement. The dimension and material properties of the elastic structure have a known relationship to the parameter being measured. Thus, the dimension is precisely measured and converted to the parameter. Other factors such as movement or acceleration can be taken into account in the calculation. As an example, a force, pressure, or load applied to the one or more contacting surfaces of sensing module 200 is used to illustrate a parameter measurement hereinbelow. It should be noted that this is for illustration purposes and that the sensing module 200 can be used to measure other parameters.

As will be shown ahead, the encapsulating enclosure can serve in a first embodiment as a trial implant for orthopedic surgical procedures, namely, for determining load forces on prosthetic components and the musculoskeletal system. In a second embodiment, the encapsulating enclosure can be placed within a permanent prosthetic component for long term monitoring. The encapsulating enclosure supports and protects internal mechanical and electronic components from external physical, mechanical, chemical, and electrical, and electromagnetic intrusion that might compromise sensing or communication operations of the module or device. The integration of the internal components is designed to minimize adverse physical, mechanical, electrical, and ultrasonic interactions that might compromise sensing or communication operations of the module or device.

Figure 4:
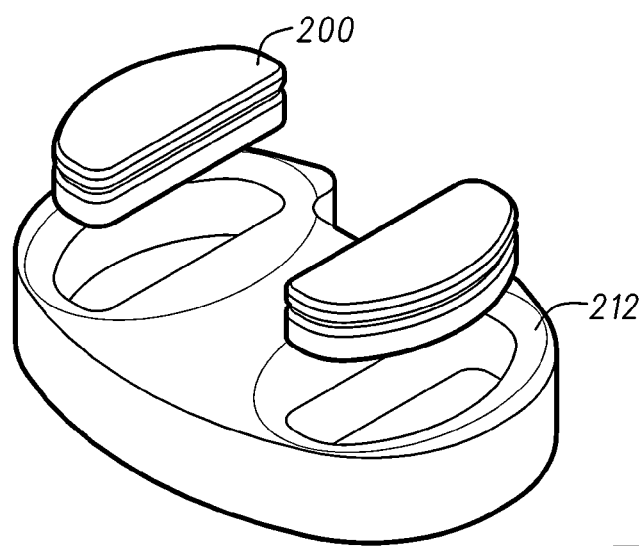
FIG. 4 is a perspective view of a medical sensing device suitable for use as a bi-compartmental implant and comprising an encapsulating enclosure in accordance with one embodiment.

FIG. 4 is a perspective view of a medical sensing device suitable for use as a bi-compartmental implant and comprising an encapsulating enclosure in accordance with one embodiment. As shown, the sensing insert device 100 comprises two sensing modules 200. Each sensing module 200 is a self-contained encapsulated enclosure that can make individual or coordinated parameter measurements. For example, the sensing insert device 100 can be used to assess load forces on a bi-compartmental knee joint implant. In particular, both sensing modules 200 can individually, or in combination, report applied loading forces. Bi-compartmental sensing provides the benefit of providing quantitative measurement to balance each compartment in relation to one another.

Similar to that described above, insert dock 202 is an adaptor having two openings instead of one. Insert dock 202 can be made in different sizes to accommodated different sized prosthetic components and different manufacturers. The insert dock 202 with two openings is a passive component for receiving two separate sensing modules 200. The opening is positioned to place the contacting surfaces in a proper orientation to measure the parameter when used in conjunction with other prosthetic components. In general, encapsulated enclosures can be positioned on or within, or engaged with, or attached or affixed to or within, a wide range of physical systems including, but not limited to instruments, appliances, vehicles, equipments, or other physical systems as well as animal and human bodies, for sensing and communicating the parameter or parameters of interest in real time. Similar to that described above, insert dock 202 as an adaptor can be manufactured at low cost providing design flexibility and allowing rapid adoption of quantitative measurement.

Figure 5:
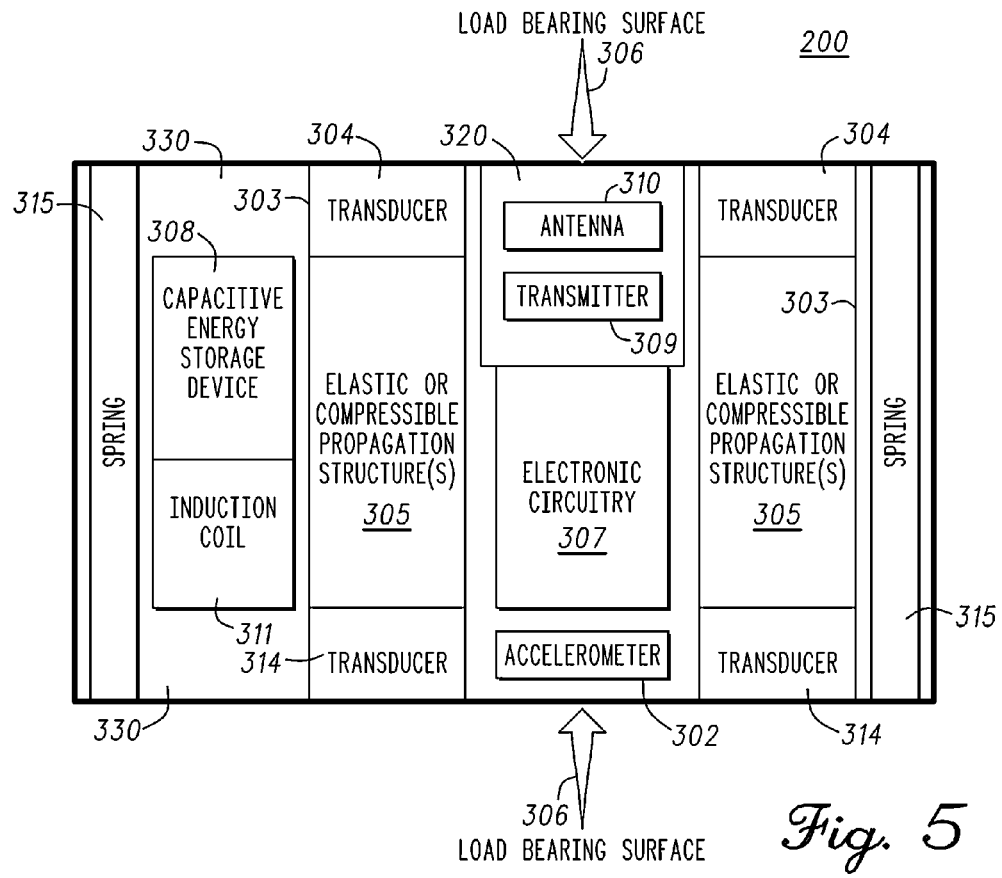
FIG. 5 is an exemplary block diagram of the components of the sensing module in accordance with an exemplary embodiment.

FIG. 5 is an exemplary block diagram of the components of the sensing module 200 in accordance with an exemplary embodiment. It should be noted that the sensing module could comprise more or less than the number of components shown. As illustrated, the sensing module includes one or more sensing assemblages 303, a transceiver 320, an energy storage 330, electronic circuitry 307, one or more mechanical supports 315 (e.g., springs), and an accelerometer 302. In the non-limiting example, an applied compressive force can be measured by the sensing module.

The sensing assemblage 303 can be positioned, engaged, attached, or affixed to the contact surfaces 306. Mechanical supports 315 serve to provide proper balancing of contact surfaces 306. In at least one exemplary embodiment, contact surfaces 306 are load-bearing surfaces. In general, the propagation structure 305 is subject to the parameter being measured. Surfaces 306 can move and tilt with changes in applied load; actions which can be transferred to the sensing assemblages 303 and measured by the electronic circuitry 307. The electronic circuitry 307 measures physical changes in the sensing assemblage 303 to determine parameters of interest, for example a level, distribution and direction of forces acting on the contact surfaces 306. In general, the sensing module is powered by the energy storage 330.

As one example, the sensing assemblage 303 can comprise an elastic or compressible propagation structure 305 between a transducer 304 and a transducer 314. In the current example, transducer 304 can be an ultrasound (or ultrasonic) resonator, and the elastic or compressible propagation structure 305 can be an ultrasound (or ultrasonic) waveguide (or waveguides). The electronic circuitry 307 is electrically coupled to the sensing assemblages 303 and translates changes in the length (or compression or extension) of the sensing assemblages 303 to parameters of interest, such as force. It measures a change in the length of the propagation structure 305 (e.g., waveguide) responsive to an applied force and converts this change into electrical signals which can be transmitted via the transceiver 320 to convey a level and a direction of the applied force. In other arrangements herein contemplated, the sensing assemblage 303 may require only a single transducer. In yet other arrangements, the sensing assemblage 303 can include piezoelectric, capacitive, optical or temperature sensors or transducers to measure the compression or displacement. It is not limited to ultrasonic transducers and waveguides.

The accelerometer 302 can measure acceleration and static gravitational pull. Accelerometer 302 can be single-axis and multi-axis accelerometer structures that detect magnitude and direction of the acceleration as a vector quantity. Accelerometer 302 can also be used to sense orientation, vibration, impact and shock. The electronic circuitry 307 in conjunction with the accelerometer 302 and sensing assemblies 303 can measure parameters of interest (e.g., distributions of load, force, pressure, displacement, movement, rotation, torque and acceleration) relative to orientations of the sensing module with respect to a reference point. In such an arrangement, spatial distributions of the measured parameters relative to a chosen frame of reference can be computed and presented for real-time display.

The transceiver 320 comprises a transmitter 309 and an antenna 310 to permit wireless operation and telemetry functions. In various embodiments, the antenna 310 can be configured by design as an integrated loop antenna. As will be explained ahead, the integrated loop antenna is configured at various layers and locations on the electronic substrate with electrical components and by way of electronic control circuitry to conduct efficiently at low power levels. Once initiated the transceiver 320 can broadcast the parameters of interest in real-time. The telemetry data can be received and decoded with various receivers, or with a custom receiver. The wireless operation can eliminate distortion of, or limitations on, measurements caused by the potential for physical interference by, or limitations imposed by, wiring and cables connecting the sensing module with a power source or with associated data collection, storage, display equipment, and data processing equipment.

The transceiver 320 receives power from the energy storage 330 and can operate at low power over various radio frequencies by way of efficient power management schemes, for example, incorporated within the electronic circuitry 307. As one example, the transceiver 320 can transmit data at selected frequencies in a chosen mode of emission by way of the antenna 310. The selected frequencies can include, but are not limited to, ISM bands recognized in International Telecommunication Union regions 1, 2 and 3. A chosen mode of emission can be, but is not limited to, Gaussian Frequency Shift Keying, (GFSK), Amplitude Shift Keying (ASK), Phase Shift Keying (PSK), Minimum Shift Keying (MSK), Frequency Modulation (FM), Amplitude Modulation (AM), or other versions of frequency or amplitude modulation (e.g., binary, coherent, quadrature, etc.).

The antenna 310 can be integrated with components of the sensing module to provide the radio frequency transmission. The substrate for the antenna 310 and electrical connections with the electronic circuitry 307 can further include a matching network. This level of integration of the antenna and electronics enables reductions in the size and cost of wireless equipment. Potential applications may include, but are not limited to any type of short-range handheld, wearable, or other portable communication equipment where compact antennas are commonly used. This includes disposable modules or devices as well as reusable modules or devices and modules or devices for long-term use.

The energy storage 330 provides power to electronic components of the sensing module. It can be charged by wired energy transfer, short-distance wireless energy transfer or a combination thereof. External power sources can include, but are not limited to, a battery or batteries, an alternating current power supply, a radio frequency receiver, an electromagnetic induction coil, a photoelectric cell or cells, a thermocouple or thermocouples, or an ultrasound transducer or transducers. By way of the energy storage 330, the sensing module can be operated with a single charge until the internal energy is drained. It can be recharged periodically to enable continuous operation. The energy storage 330 can utilize power management technologies such as replaceable batteries, supply regulation technologies, and charging system technologies for supplying energy to the components of the sensing module to facilitate wireless applications.

The energy storage 330 minimizes additional sources of energy radiation required to power the sensing module during measurement operations. In one embodiment, as illustrated, the energy storage 330 can include a capacitive energy storage device 308 and an induction coil 311. External source of charging power can be coupled wirelessly to the capacitive energy storage device 308 through the electromagnetic induction coil or coils 311 by way of inductive charging. The charging operation can be controlled by power management systems designed into, or with, the electronic circuitry 307. As one example, during operation of electronic circuitry 307, power can be transferred from capacitive energy storage device 308 by way of efficient step-up and step-down voltage conversion circuitry. This conserves operating power of circuit blocks at a minimum voltage level to support the required level of performance.

In one configuration, the energy storage 330 can further serve to communicate downlink data to the transceiver 320 during a recharging operation. For instance, downlink control data can be modulated onto the energy source signal and thereafter demodulated from the induction coil 311 by way of electronic control circuitry 307. This can serve as a more efficient way for receiving downlink data instead of configuring the transceiver 320 for both uplink and downlink operation. As one example, downlink data can include updated control parameters that the sensing module uses when making a measurement, such as external positional information, or for recalibration purposes, such as spring biasing. It can also be used to download a serial number or other identification data.

The electronic circuitry 307 manages and controls various operations of the components of the sensing module, such as sensing, power management, telemetry, and acceleration sensing. It can include analog circuits, digital circuits, integrated circuits, discrete components, or any combination thereof. In one arrangement, it can be partitioned among integrated circuits and discrete components to minimize power consumption without compromising performance. Partitioning functions between digital and analog circuit enhances design flexibility and facilitates minimizing power consumption without sacrificing functionality or performance. Accordingly, the electronic circuitry 307 can comprise one or more Application Specific Integrated Circuit (ASIC) chips, for example, specific to a core signal processing algorithm.

In another arrangement, the electronic circuitry can comprise a controller such as a programmable processor, a Digital Signal Processor (DSP), a microcontroller, or a microprocessor, with associated storage memory and logic. The controller can utilize computing technologies with associated storage memory such a Flash, ROM, RAM, SRAM, DRAM or other like technologies for controlling operations of the aforementioned components of the sensing module. In one arrangement, the storage memory may store one or more sets of instructions (e.g., software) embodying any one or more of the methodologies or functions described herein. The instructions may also reside, completely or at least partially, within other memory, and/or a processor during execution thereof by another processor or computer system.

The electronics assemblage also supports testability and calibration features that assure the quality, accuracy, and reliability of the completed wireless sensing module or device. A temporary bi-directional interconnect assures a high level of electrical observability and controllability of the electronics. The test interconnect also provides a high level of electrical observability of the sensing subsystem, including the transducers, waveguides, and mechanical spring or elastic assembly. Carriers or fixtures emulate the final enclosure of the completed wireless sensing module or device during manufacturing processing thus enabling capture of accurate calibration data for the calibrated parameters of the finished wireless sensing module or device. These calibration parameters are stored within the on-board memory integrated into the electronics assemblage.

Applications for sensing module 200 may include, but are not limited to, disposable modules or devices as well as reusable modules or devices and modules or devices for long-term use. In addition to non-medical applications, examples of a wide range of potential medical applications may include, but are not limited to, implantable devices, modules within implantable devices, intra-operative implants or modules within intra-operative implants or trial inserts, modules within inserted or ingested devices, modules within wearable devices, modules within handheld devices, modules within instruments, appliances, equipment, or accessories of all of these, or disposables within implants, trial inserts, inserted or ingested devices, wearable devices, handheld devices, instruments, appliances, equipment, or accessories to these devices, instruments, appliances, or equipment.

Figure 6:
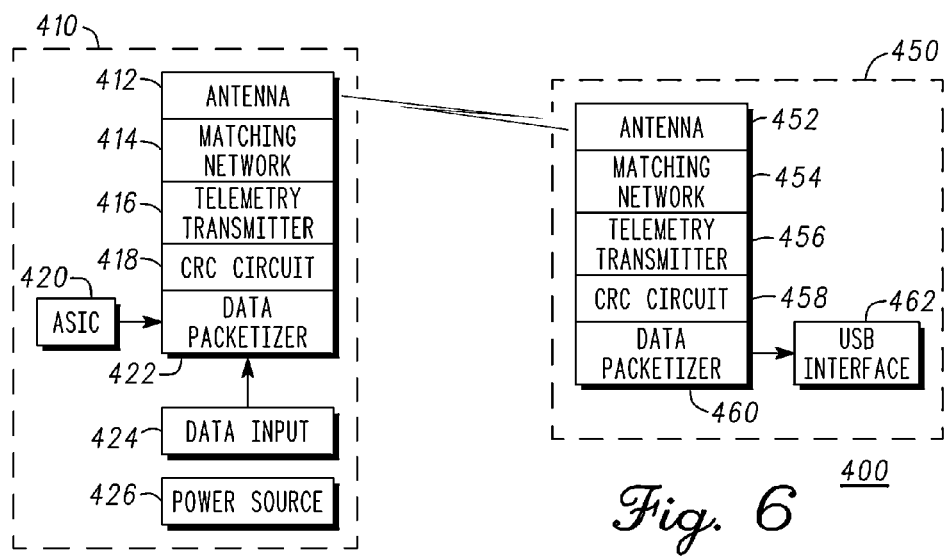
FIG. 6 is a diagram of an exemplary communications system for short-range telemetry according to one embodiment.

FIG. 6 is a diagram of an exemplary communications system 400 for short-range telemetry according to one embodiment. As illustrated, the exemplary communications system 400 comprises medical device communications components 410 of the sensing insert device 100 (see FIG. 1) and receiving system communications components 450 of the receiving system 110 (see FIG. 1). The medical device communications components 410 are inter-operatively coupled to include, but not limited to, the antenna 412, a matching network 414, the telemetry transceiver 416, a CRC circuit 418, a data packetizer 422, a data input 424, a power source 426, and an application specific integrated circuit (ASIC) 420. The medical device communications components 410 may include more or less than the number of components shown and are not limited to those shown or the order of the components.

The receiving station communications components 450 comprise an antenna 452, the matching network 454, the telemetry receiver 456, the CRC circuit 458, the data packetizer 460, and optionally a USB interface 462. Notably, other interface systems can be directly coupled to the data packetizer 460 for processing and rendering sensor data.

With respect to FIG. 1, in view of the communication components of FIG. 6, the sensing insert device 100 acquires sensor data by way of the data input to the ASIC 420. Referring briefly to FIG. 5, the ASIC 420 is operatively coupled to sensing assemblies 303. In one embodiment, a change in the parameter being measured by device 100 produces a change in a length of a compressible propagation structure 305. ASIC 420 controls the emission of energy waves into propagation structure 305 and the detection of propagated energy waves. ASIC 420 generates data related to transit time, frequency, or phase of propagated energy waves. The data corresponds to the length of propagation structure 305, which can be translated to the parameter of interest by way of a known function or relationship. Similarly, the data can comprise voltage or current measurements from a MEMS structure, piezo-resistive sensor, strain gauge, or other sensor type that is used to measure the parameter. The data packetizer 422 assembles the sensor data into packets; this includes sensor information received or processed by ASIC 420. The ASIC 420 can comprise specific modules for efficiently performing core signal processing functions of the medical device communications components 410. The ASIC 420 provides the further benefit of reducing the form factor of sensing insert device 100 to meet dimensional requirements for integration into temporary or permanent prosthetic components.

The CRC circuit 418 applies error code detection on the packet data. The cyclic redundancy check is based on an algorithm that computes a checksum for a data stream or packet of any length. These checksums can be used to detect interference or accidental alteration of data during transmission. Cyclic redundancy checks are especially good at detecting errors caused by electrical noise and therefore enable robust protection against improper processing of corrupted data in environments having high levels of electromagnetic activity. The telemetry transmitter 416 then transmits the CRC encoded data packet through the matching network 414 by way of the antenna 412. The matching networks 414 and 454 provide an impedance match for achieving optimal communication power efficiency.

The receiving system communications components 450 receive transmission sent by medical device communications components 410. In one embodiment, telemetry transmitter 416 is operated in conjunction with a dedicated telemetry receiver 456 that is constrained to receive a data stream broadcast on the specified frequencies in the specified mode of emission. The telemetry receiver 456 by way of the receiving station antenna 452 detects incoming transmissions at the specified frequencies. The antenna 452 can be a directional antenna that is directed to a directional antenna of components 410. Using at least one directional antenna can reduce data corruption while increasing data security by further limiting where the data is radiated. A matching network 454 couples to antenna 452 to provide an impedance match that efficiently transfers the signal from antenna 452 to telemetry receiver 456. Telemetry receiver 456 can reduce a carrier frequency in one or more steps and strip off the information or data sent by components 410. Telemetry receiver 456 couples to CRC circuit 458. CRC circuit 458 verifies the cyclic redundancy checksum for individual packets of data. CRC circuit 458 is coupled to data packetizer 460. Data packetizer 460 processes the individual packets of data. In general, the data that is verified by the CRC circuit 458 is decoded (e.g., unpacked) and forwarded to an external data processing device, such as an external computer, for subsequent processing, display, or storage or some combination of these.

The telemetry receiver 456 is designed and constructed to operate on very low power such as, but not limited to, the power available from the powered USB port 462, or a battery. In another embodiment, the telemetry receiver 456 is designed for use with a minimum of controllable functions to limit opportunities for inadvertent corruption or malicious tampering with received data. The telemetry receiver 456 can be designed and constructed to be compact, inexpensive, and easily manufactured with standard manufacturing processes while assuring consistently high levels of quality and reliability.

In one configuration, the communication system 400 operates in a transmit-only operation with a broadcasting range on the order of a few meters to provide high security and protection against any form of unauthorized or accidental query. The transmission range can be controlled by the transmitted signal strength, antenna selection, or a combination of both. A high repetition rate of transmission can be used in conjunction with the Cyclic Redundancy Check (CRC) bits embedded in the transmitted packets of data during data capture operations thereby enabling the receiving system 110 to discard corrupted data without materially affecting display of data or integrity of visual representation of data, including but not limited to measurements of load, force, pressure, displacement, flexion, attitude, and position within operating or static physical systems.

By limiting the operating range to distances on the order of a few meters the telemetry transmitter 416 can be operated at very low power in the appropriate emission mode or modes for the chosen operating frequencies without compromising the repetition rate of the transmission of data. This mode of operation also supports operation with compact antennas, such as an integrated loop antenna. The combination of low power and compact antennas enables the construction of, but is not limited to, highly compact telemetry transmitters that can be used for a wide range of non-medical and medical applications. Examples of potential medical applications may include, but are not limited to, implantable devices, modules within implantable devices, intra-operative implants or modules within intra-operative implants or trial inserts, modules within inserted or ingested devices, modules within wearable devices, modules within handheld devices, modules within instruments, appliances, equipment, or accessories of all of these, or disposables within implants, trial inserts, inserted or ingested devices, wearable devices, handheld devices, instruments, appliances, equipment, or accessories to these devices, instruments, appliances, or equipment.

The transmitter security as well as integrity of the transmitted data is assured by operating the telemetry system within predetermined conditions. The security of the transmitter cannot be compromised because it is operated in a transmit-only mode and there is no pathway to hack into medical device communications components 410. The integrity of the data is assured with the use of the CRC algorithm and the repetition rate of the measurements. The risk of unauthorized reception of the data is minimized by the limited broadcast range of the device. Even if unauthorized reception of the data packets should occur there are counter measures in place that further mitigate data access. A first measure is that the transmitted data packets contain only binary bits from a counter along with the CRC bits. A second measure is that no data is available or required to interpret the significance of the binary value broadcast at any time. A third measure that can be implemented is that no patient or device identification data is broadcast at any time.

The telemetry transmitter 416 can also operate in accordance with some FCC regulations. According to section 18.301 of the FCC regulations the ISM bands within the USA include 6.78, 13.56, 27.12, 30.68, 915, 2450, and 5800 MHz as well as 24.125, 61.25, 122.50, and 245 GHz. Globally other ISM bands, including 433 MHz, are defined by the International Telecommunications Union in some geographic locations. The list of prohibited frequency bands defined in 18.303 are "the following safety, search and rescue frequency bands is prohibited: 490-510 kHz, 2170-2194 kHz, 8354-8374 kHz, 121.4-121.6 MHz, 156.7-156.9 MHz, and 242.8-243.2 MHz." Section 18.305 stipulates the field strength and emission levels ISM equipment must not exceed when operated outside defined ISM bands. In summary, it may be concluded that ISM equipment may be operated worldwide within ISM bands as well as within most other frequency bands above 9 KHz given that the limits on field strengths and emission levels specified in section 18.305 are maintained by design or by active control. As an alternative, commercially available ISM transceivers, including commercially available integrated circuit ISM transceivers, may be designed to fulfill these field strengths and emission level requirements when used properly.

In one configuration, the telemetry transmitter 416 can also operate in unlicensed ISM bands or in unlicensed operation of low power equipment, wherein the ISM equipment (e.g., telemetry transmitter 416) may be operated on ANY frequency above 9 kHz except as indicated in Section 18.303 of the FCC code.

Wireless operation eliminates distortion of, or limitations on, measurements caused by the potential for physical interference by, or limitations imposed by, wiring and cables connecting the wireless sensing module or device with a power source or with data collection, storage, or display equipment. Power for the sensing components and electronic circuits is maintained within the wireless sensing module or device on an internal energy storage device. This energy storage device is charged with external power sources including, but not limited to, a battery or batteries, super capacitors, capacitors, an alternating current power supply, a radio frequency receiver, an electromagnetic induction coil, a photoelectric cell or cells, a thermocouple or thermocouples, or an ultrasound transducer or transducers. The wireless sensing module may be operated with a single charge until the internal energy source is drained or the energy source may be recharged periodically to enable continuous operation. The embedded power supply minimizes additional sources of energy radiation required to power the wireless sensing module or device during measurement operations. Telemetry functions are also integrated within the wireless sensing module or device. Once initiated the telemetry transmitter continuously broadcasts measurement data in real time. Telemetry data may be received and decoded with commercial receivers or with a simple, low cost custom receiver.

A method can be practiced with more or less than the number of steps shown and is not limited to the order shown. To describe the method, reference will be made to the components of FIG. 5, although it is understood that the method can be implemented in any other manner using other suitable components. Generally, method is directed to non-secure applications for one-way transmission communications, for example, where an implanted medical device or sensor transmits data to a receiving station (e.g., 110 see FIG. 1) but does not receive confirmation from the receiving station, although in various embodiments, the implanted medical device includes an integrated receiver for receiving confirmation and acknowledgement communications.

The method can start in a state wherein the sensing insert device 100 has been inserted and powered on, for example, within a knee prosthesis implant. The medical device can be powered on via manual intervention, for example, by the surgeon or technician implanting the medical device during a surgical procedure, or the device can turn on automatically after a duration of time or at certain time intervals, for example, 1 hour after manual activation, or every 10 seconds after power up, depending on an operating mode.

In a first step, the medical device acquires sensor data such as load information (e.g., force, location, duration, etc.) from the sensing module 200. The electronic circuitry 307 generates the load data by way of the sensing assemblies 303, for instance, by converting changes in length of ultrasonic propagation structures (waveguides) to force data. In a second step, the sensing module 200 evaluates data bounds on the load data. In a third step, sensing module 200 assigns priorities based on the data bounds. Sensor data outside a predetermined range or above a predefined threshold can be flagged with a priority or discarded. For example, sensor data that falls outside a safe range or exceeds a safe level (e.g., applied force level, angle of flexion, excessive rotation) is prioritized accordingly.

In a fourth step, the sensing module 200 generates a packet of data including the sensor data, priority, and any corresponding information. In a fifth step, the sensing module 200 determines its communications mode based on operating mode and priority level. The operating mode indicates whether the sensing module 200 is operating in a power saving mode (e.g., standby) or other power management mode and takes into account information such as remaining battery life and drain. In a sixth step, a Cyclic Redundancy Check (CRC) can be appended to the data packed. In other embodiments, more sophisticated forward error correction schemes (e.g., block coding, convolutional coding) can be applied along with secure encryption or key-exchange cryptographic protocols.

Figure 13:
FIG. 13 is an illustration of an exemplary data packet containing sensor data.

The cyclic redundancy check (CRC) is a non-secure form of message digest designed to detect accidental changes to raw computer data. The CRC step comprises calculating a short, fixed-length sequence, known as the CRC code, for each block of data and sends or stores them both together. When a block is read or received the receiving station 110 (FIG. 1) repeats the calculation; if the new CRC does not match the one sent (or in some cases, cancel it out) then the block contains a data error and the receiving station 110 may take corrective action such as rereading or requesting the block be sent again. Briefly, FIG. 13, illustrates an exemplary data packet 1300 containing sensor data (e.g., Fx, duration, location), a priority level (e.g., 1 to 10), and a CRC.

In a seventh step, the transceiver 320 then transmits the data packet based on the priority level and operating mode. For instance, a low priority data packet can be appended with previous low-priority data packets and then transmitted over a single communication channel as a data stream, or at staggered time intervals to conserve power (e.g., scheduled to transmit every 10 seconds). The bundled packet data can then be decoded at the receiving station 110 and thereafter processed accordingly. Alternatively, a high priority packet can be transmitted immediately instead of a delayed time or the scheduled transmit intervals. Depending on the communication mode (e.g., priority level, operating mode), the transceiver may transmit the same high priority packet multiple times in a redundant manner to guarantee receipt. This ensures that the data is received and processed at the receiving station 110 in the event an immediate course of action or response is necessary, for example, to ensure the patient's safety or to report a warning.

The sensor data can be transmitted at the selected frequencies in the chosen mode of emission by way of the antenna 310. In certain configurations, the antenna 310 is an integrated loop antenna designed into a substrate of the sensing module 200 for maximizing power efficiency. As an example the chosen frequencies can include, but are not limited to, ISM bands recognized in International Telecommunication Union regions 1, 2, and 3 and the chosen mode of emission may be, but is not limited to, Gaussian Frequency Shift Keying, (GFSK) or others version of frequency or amplitude shift keying or modulation.

The receiving station 110 (see FIG. 1) 110 receives packets of data broadcast in the specified mode of emission on the specified frequencies and verifies the cyclic redundancy check checksum for individual packets of data or bundled packet data. Data that cannot be verified may be discarded. Data that are verified are forward to an external data processing device, such as an external computer, for subsequent processing, display, or storage or combination thereof.

Figure 7:
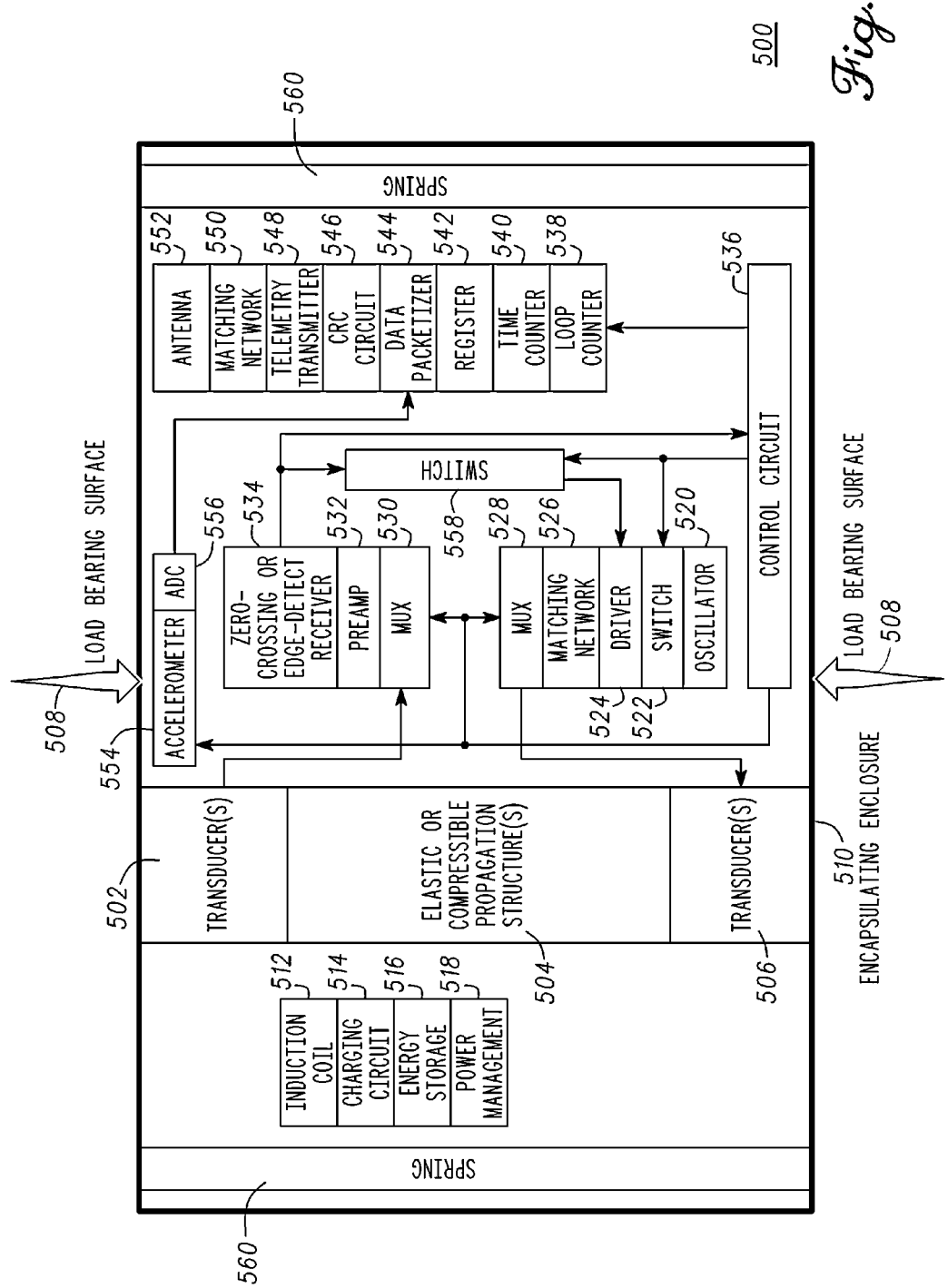
FIG. 7 is an illustration of a block model diagram of the sensing module in accordance with an exemplary embodiment.

FIG. 7 is an illustration of a block model diagram 500 of the sensing module 200 in accordance with an exemplary embodiment. In particular, the diagram 500 shows where certain components are replaced or supplemented with one or more Application Specific Integrated Circuits (ASICs). Referring briefly to FIG. 5, electronic circuitry 307 is coupled to the one or more sensing assemblages and includes circuitry that can control sensor operations. Electronic circuitry 307 includes multiple channels that can operate more than one device. Sensing module 200 is optimized to operate under severe power constraints. Electronic circuitry 307 includes power management circuitry that controls power up, power down, and minimizes power usage through the control of individual blocks. The architecture is designed to enable only blocks required for the current operation.

Referring back to FIG. 7, the ASIC provides significant benefit in reducing power requirements allowing the module 200 to be powered by a temporary power source such as a super capacitor or capacitor. The ASIC and super capacitor have a small form factor allowing module 200 to be integrated within a temporary or permanent prosthetic component. Module 200 incorporates one or more sensors comprising at least one transducer and a compressible media, the operation of which is disclosed in detail herein. As shown, a sensing assemblage comprises a transducer 502, compressible propagation structure 504, and a transducer 506. It should be noted that other sensors such as MEMS devices, strain gauges, and piezo-resistive sensors can be used with the ASIC. In particular, the ASIC incorporates A/D and D/A circuitry (not shown) to digitize current and voltage output from these types of sensing components. Transducers 502 and 506 operatively couple to compressible propagation structure 504. In a non-limiting example, transducer 506 to emits energy waves into compressible structure 504 while transducer 502 detects propagated energy waves. Compressible propagation structure 504 is coupled to a load bearing or contacting surface 508 and an encapsulating enclosure 510 of sensing module 200. A parameter to be measured is applied to either contacting surface 508, encapsulating enclosure 510, or both. In one embodiment, springs 560 couple to contacting surface 508 and encapsulating enclosure 510 to support compressible propagation structure 504. In particular, springs 560 prevent cantilevering of contacting surface 508, reduce hysteresis caused by material properties of compressible propagation structure 504, and improve sensor response time to changes in the applied parameter.

In one embodiment, a first ASIC includes a charging circuit 514 and power management circuitry 518. The power management circuitry 518 couples to the charging circuit, other blocks of the ASIC and external components/circuitry to minimize power consumption of the integrated circuit. The charging circuit 514 operatively couples to an induction coil 512 and energy storage 516. In a non-limiting example, induction coil 512 couples to an external coil that provides energy to charge energy storage 516. Induction coil 512 and the external coil are placed in proximity to each other thereby electro-magnetically coupling to one another. Induction coil 512 is coupled to energy storage 516. Charging circuit 514 controls the charging of energy storage 516. Charging circuit 514 can determine when charging is complete, monitor power available, and regulate a voltage provided to the operational circuitry. Charging circuit 514 can charge a battery in sensing module 200. Alternatively, a capacitor or super capacitor can be used to power the first ASIC for a time sufficient to acquire the desired measurements. A capacitor has the benefit of a long or indefinite shelf life and fast charge time. In either charging scenario, energy from the external coil is coupled to the induction coil 512. The energy from induction coil 512 is then stored in a medium such as a battery or capacitor.

Benefits of ultracapacitors, ultra capacitors, or super capacitors, or other form of capacitors as a power source instead or, or in conjunction with, other power sources or rechargeable technologies include, but are not limited to, enabling a high level of miniaturization as ultracapacitors, ultra capacitors, or super capacitors are smaller than smallest available battery for the same level of energy and power for many low power applications or applications that require power only intermittently or as a short-term backup for other power sources.

For applications that require power only intermittently, capacitors enable rapid recharge that is much faster than battery technologies and rechargeable chemistries regardless of their energy capacity. A charge time, from a completely uncharged state takes minutes because no chemical processes are involved in charging capacitors. This may be compared to charge times on the order of hours for many battery technologies that cannot be charged at a rate faster that one-half the energy storage capacity of the battery within one hour. In practice, many battery applications charge at a much slower rate. Many capacitors have the added benefit of almost indefinite lifetimes. There is no deterioration of a capacitor's storage capacity when uncharged, regardless of length of time at zero charge. Another benefit is that overcharging capacitors may pose less risk to electronics within an electronic module or device than overcharging batteries might pose. Furthermore, capacitors eliminate storage and disposal limitations of batteries with no risk of chemical leakage. In addition, capacitors can have a smaller form factor, are surface-mountable, and integrate well into the electronics assemblies and standard surface-mount electronic assembly processes.

Use capacitors to provide operating power for wireless devices, telemetry devices, or medical devices provides design, construction, and operating flexibility over a wide range of potential applications. Capacitors can be charged by connecting them to other power sources such as, but not limited to, a battery or batteries, an alternating current (AC) power supply, a radio frequency (RF) receiver, or an electromagnetic induction coil or coils, a photoelectric cell or cells, a thermocouple or thermocouples, capacitors, or an ultrasound transducer or transducers. For compact electronic modules or devices, ultracapacitors, super capacitors, or other form of capacitors provide many benefits over other rechargeable technologies.

The first ASIC further includes circuitry to operate and capture data from the sensing assemblages. A parameter to be measured is applied to compressible propagation structure 504. As an example of parameter measurement, a force, pressure, or load is applied across contacting surface 508 and encapsulating enclosure 510. The force, pressure, or load affects the length of the compressible propagation structure 504. The circuitry on the first ASIC forms a positive closed loop feedback circuit that maintains the emission, propagation, and detection of energy waves in the compressible propagation structure 504. The first ASIC operatively couples to transducers 502 and 506 to control the positive closed loop feedback circuit that is herein called a propagation tuned oscillator (PTO). The first ASIC measures a transit time, frequency, or phase of propagated energy waves. The measurement is used to determine the length of compressible propagation structure 504. The energy waves emitted into compressible propagation structure 504 can be continuous or pulsed. The energy waves can propagate by a direct path or be reflected.

The first ASIC comprises an oscillator 520, a switch 522, driver 524, matching network 526, MUX 528, and control circuit 536. The oscillator 520 is used as a reference clock for the ASIC and enables the PTO to begin emission of energy waves into the compressible propagation structure 504. Oscillator 520 in the first ASIC can be coupled to an external component such as a crystal oscillator to define and provide a stable frequency of operation. Switch 522 couples the oscillator 520 to MUX 528. Control circuit 536 operatively enables MUX 528 and switch 522 to couple oscillator 520 to driver 524 during a startup sequence. Driver 524 and matching network 526 couple to transducer 506. Driver 524 drives transducer 506 to emit an energy wave. Matching network 526 impedance matches driver 524 to the transducer 506 to reduce power consumption during energy wave emission.

In one embodiment, transducer 506 emits one or more energy waves into the compressible propagation structure 504 at a first location. Transducer 506 is located at a second location of compressible propagation structure 504. Transducer 506 detects propagated energy waves at the second location and generates a signal corresponding to the propagated energy waves. The first ASIC further comprises a MUX 530, pre-amplifier 532 (e.g. preamp 532) and a zero-crossing receiver or edge detect receiver. Zero-crossing receiver or edge-detect receiver comprise detect circuit 534. Control circuit 536 enables MUX 530 to couple transducer 502 to preamp 532. Preamp 532 amplifies a signal output by transducer 502 corresponding to a propagated energy wave. In a non-limiting example, the first ASIC comprises both a zero-crossing receiver and an edge detect receiver. More multiplexing circuitry in conjunction with control circuit 536 can be incorporated on the first ASIC to select between the circuits. Similarly, multiplexing circuitry can be used to couple and operate more than one sensor. The amplified signal from preamp 532 is coupled to detection circuit 534. Zero-crossing receiver is a detection circuit that identifies a propagated energy wave by sensing a transition of the signal. A requirement of detection can be that the signal has certain transition and magnitude characteristics. The edge-detect receiver detects a propagated energy wave by identifying a wave front of the propagated energy wave. The zero-crossing receiver or edge-detect receiver outputs a pulse in response to the detection of a propagated energy wave.

Positive closed loop feedback is applied upon detection of an energy wave after the startup sequence. Control circuit 536 decouples oscillator 520 from driver 524 through switch 522 and MUX 528. Control circuit 536 operatively enables switch 558 and MUX 528 to couple detection circuit 534 to driver 524. A pulse generated by detection circuit 534 initiates the emission of a new energy wave into compressible propagation structure 504. The pulse from detection circuit 534 is provided to driver 524. The positive closed loop feedback of the circuitry maintains the emission, propagation, and detection of energy waves in propagation structure 504.

The first ASIC further comprises a loop counter 538, time counter 540, register 542, and ADC 556. Loop counter 538, time counter 540, and register 542 are operatively coupled to control circuit 536 to generate a precise measurement of the transit time, frequency, or phase of propagated energy waves during a measurement sequence. In one embodiment, a measurement comprises a predetermined number of energy waves propagating through the compressible propagation structure 504. The predetermined number is set in the loop counter 538. The loop counter 538 is decremented by each pulse output by detection circuit 534 that corresponds to a detected propagated energy wave. The positive closed loop feedback is broken when counter 538 decrements to zero thereby stopping the measurement. Time counter 540 measures a total propagation time of the predetermined number of propagated energy waves set in loop counter 538. The measured total propagation time divided by the predetermined number of propagated energy waves is a measured transit time of an energy wave. The measured transit time can be precisely converted to a length of compressible propagation structure 504 under a stable condition of the applied parameter on the sensing assemblage. The applied parameter value can be calculated by known relationship between the length of compressible propagation structure 504 and the parameter. A result of the measurement is stored in register 542 when loop counter 538 decrements to zero. More than one measurement can be performed and stored. In one embodiment, the precision can be increased by raising the number of propagated energy waves being measured in loop counter 538.

In the example, energy waves are propagated from transducer 506 to transducer 5. Alternatively, control circuit 536 can direct the propagation of energy waves from transducer 502 to transducer 506 whereby transducer 502 emits energy waves and transducer 506 detects propagated energy waves. An analog to digital converter (ADC) 556 is shown coupled to an accelerometer 554. ADC 556 is a circuit on the first ASIC. It can be used to digitize an output from a circuit such as accelerometer 554. Accelerometer 554 can be used to detect and measure when sensing module 200 is in motion. Data from accelerometer 554 can be used to correct the measured result to account for module 200 acceleration. ADC 556 can also be used to provide measurement data from other sensor types by providing a digitized output corresponding to voltage or current magnitude.

A second ASIC can comprise CRC circuit 546, telemetry transmitter 548, and matching network 508. The CRC circuit 546 applies error code detection on the packet data such as data stored in register 542. The cyclic redundancy check computes a checksum for a data stream or packet of any length. The checksums are used to detect interference or accidental alteration of data during transmission. Transmitter 548 is coupled to CRC 546 and sends the data wirelessly. Matching network 550 couples telemetry transmitter 512 to antenna 552 to provide an impedance match to efficiently transfer the signal to the antenna 552. As disclosed above, the integration of the telemetry transmitter and sensor modules enables construction of a wide range of sizes of the sensing module 200. This facilitates capturing data, measuring parameters of interest and digitizing that data, and subsequently communicating that data to external equipment with minimal disturbance to the operation of the body, instrument, appliance, vehicle, equipment, or physical system for a wide range of applications. Moreover, the level of accuracy and resolution achieved by the total integration of communication components, transducers, waveguides, and oscillators to control the operating frequency of the ultrasound transducers enables the compact, self-contained measurement module construction. In a further embodiment, the circuitry on the first and second ASICs can be combined on a single ASIC to further reduce form factor, power, and cost.

Figure 8:
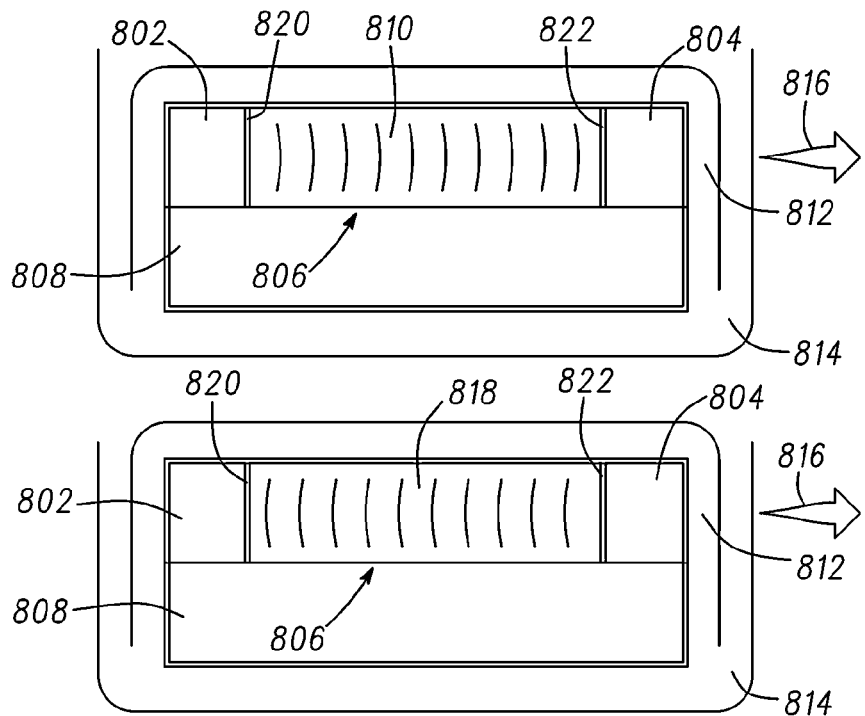
FIG. 8 is an exemplary assemblage that illustrates propagation of ultrasound waves within the waveguide in the bi-directional mode of operation of this assemblage in accordance with one embodiment.

FIG. 8 is an exemplary assemblage 800 that illustrates propagation of ultrasound waves 810 within the waveguide 806 in the bi-directional mode of operation of this assemblage. In this mode, the selection of the roles of the two individual ultrasound resonators (802, 804) or transducers affixed to interfacing material 820 and 822, if required, are periodically reversed. In the bi-directional mode the transit time of ultrasound waves propagating in either direction within the waveguide 806 can be measured. This can enable adjustment for Doppler effects in applications where the sensing module 808 is operating while in motion 816. Furthermore, this mode of operation helps assure accurate measurement of the applied load, force, pressure, or displacement by capturing data for computing adjustments to offset this external motion 816. An advantage is provided in situations wherein the body, instrument, appliance, vehicle, equipment, or other physical system 814, is itself operating or moving during sensing of load, pressure, or displacement. Similarly, the capability can also correct in situation where the body, instrument, appliance, vehicle, equipment, or other physical system, is causing the portion 812 of the body, instrument, appliance, vehicle, equipment, or other physical system being measured to be in motion 816 during sensing of load, force, pressure, or displacement. Other adjustments to the measurement for physical changes to system 814 are contemplated and can be compensated for in a similar fashion. For example, temperature of system 814 can be measured and a lookup table or equation having a relationship of temperature versus transit time can be used to normalize measurements. Differential measurement techniques can also be used to cancel many types of common factors as is known in the art.

The use of waveguide 806 enables the construction of low cost sensing modules and devices over a wide range of sizes, including highly compact sensing modules, disposable modules for bio-medical applications, and devices, using standard components and manufacturing processes. The flexibility to construct sensing modules and devices with very high levels of measurement accuracy, repeatability, and resolution that can scale over a wide range of sizes enables sensing modules and devices to the tailored to fit and collect data on the physical parameter or parameters of interest for a wide range of medical and non-medical applications.

Referring back to FIG. 2, although not explicitly illustrated, it should be noted that the load insert sensing device 100 and associated internal components move in accordance with motion of the femur 108 as shown. The bi-directional operating mode of the waveguide mitigates the Doppler effects resulting from the motion. As previously indicated, incorporating data from the accelerometer 121 with data from the other components of the sensing module 200 helps assure accurate measurement of the applied load, force, pressure, displacement, density, localized temperature, or viscosity by enabling computation of adjustments to offset this external motion.

For example, sensing modules or devices may be placed on or within, or attached or affixed to or within, a wide range of physical systems including, but not limited to instruments, appliances, vehicles, equipments, or other physical systems as well as animal and human bodies, for sensing the parameter or parameters of interest in real time without disturbing the operation of the body, instrument, appliance, vehicle, equipment, or physical system.

In addition to non-medical applications, examples of a wide range of potential medical applications may include, but are not limited to, implantable devices, modules within implantable devices, modules or devices within intra-operative implants or trial inserts, modules within inserted or ingested devices, modules within wearable devices, modules within handheld devices, modules within instruments, appliances, equipment, or accessories of all of these, or disposables within implants, trial inserts, inserted or ingested devices, wearable devices, handheld devices, instruments, appliances, equipment, or accessories to these devices, instruments, appliances, or equipment. Many physiological parameters within animal or human bodies may be measured including, but not limited to, loading within individual joints, bone density, movement, various parameters of interstitial fluids including, but not limited to, viscosity, pressure, and localized temperature with applications throughout the vascular, lymph, respiratory, and digestive systems, as well as within or affecting muscles, bones, joints, and soft tissue areas. For example, orthopedic applications may include, but are not limited to, load bearing prosthetic components, or provisional or trial prosthetic components for, but not limited to, surgical procedures for knees, hips, shoulders, elbows, wrists, ankles, and spines; any other orthopedic or musculoskeletal implant, or any combination of these.

Figure 9:
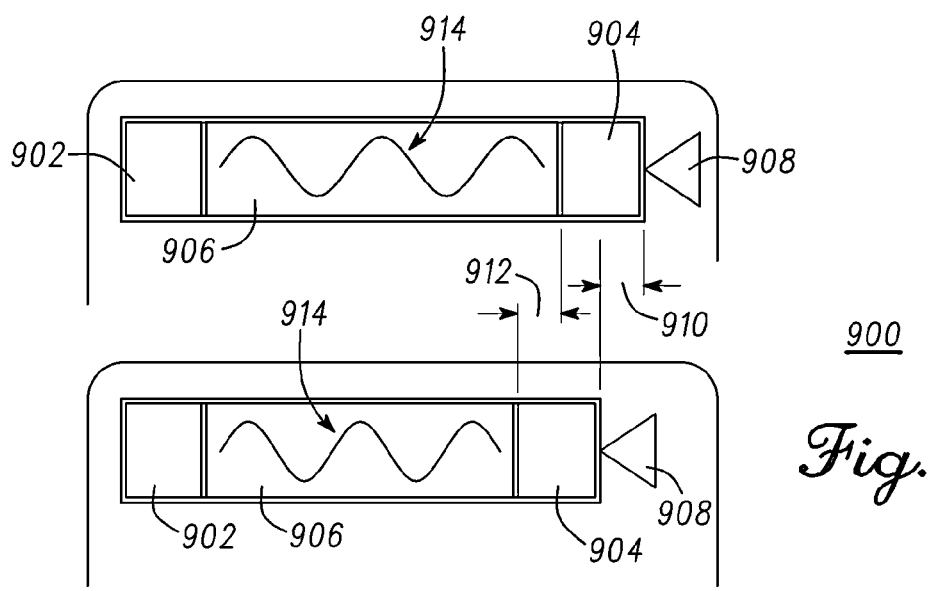
FIG. 9 is an exemplary cross-sectional view of an ultrasound waveguide to illustrate changes in the propagation of ultrasound waves with changes in the length of the waveguide in accordance with one embodiment.

FIG. 9 is an exemplary cross-sectional view of a sensor element 900 to illustrate changes in the propagation of ultrasound waves 914 with changes in the length of a waveguide 906. In general, the measurement of a parameter is achieved by relating displacement to the parameter. In one embodiment, the displacement required over the entire measurement range is measured in microns. For example, an external force 908 compresses waveguide 906 thereby changing the length of waveguide 906. Sensing circuitry (not shown) measures propagation characteristics of ultrasonic signals in the waveguide 906 to determine the change in the length of the waveguide 906. These changes in length change in direct proportion to the parameters of interest thus enabling the conversion of changes in the parameter or parameters of interest into electrical signals.

As previously discussed, external forces applied to the sensing module 200 compress the waveguide(s) thereby changing the length of the waveguide(s). The sensing module 200 measures propagation characteristics of ultrasonic signals in the waveguide(s) to determine the change in the length of the waveguide(s). These changes in length change in direct proportion to the parameters of interest thus enabling the conversion of changes in the parameter or parameters of interest into load (or force) information.

As illustrated, external force 908 compresses waveguide 906 and pushes the transducers 902 and 904 closer to one another by a distance 910. This changes the length of waveguide 906 by distance 912 of the waveguide propagation path between transducers 902 and 904. Depending on the operating mode, the sensing circuitry measures the change in length of the waveguide 906 by analyzing characteristics of the propagation of ultrasound waves within the waveguide.

One interpretation of FIG. 9 illustrates waves emitting from transducer 902 at one end of waveguide 906 and propagating to transducer 904 at the other end of the waveguide 906. The interpretation includes the effect of movement of waveguide 906 and thus the velocity of waves propagating within waveguide 906 (without changing shape or width of individual waves) and therefore the transit time between transducers 902 and 904 at each end of the waveguide. The interpretation further includes the opposite effect on waves propagating in the opposite direction and is evaluated to estimate the velocity of the waveguide and remove it by averaging the transit time of waves propagating in both directions.

Changes in the parameter or parameters of interest are measured by measuring changes in the transit time of energy pulses or waves within the propagating medium. Closed loop measurement of changes in the parameter or parameters of interest is achieved by modulating the repetition rate of energy pulses or the frequency of energy waves as a function of the propagation characteristics of the elastic energy propagating structure.

In a continuous wave mode of operation, a phase detector (not shown) evaluates the frequency and changes in the frequency of resonant ultrasonic waves in the waveguide 906. As will be described below, positive feedback closed-loop circuit operation in continuous wave (CW) mode adjusts the frequency of ultrasonic waves 914 in the waveguide 906 to maintain a same number or integer number of periods of ultrasonic waves in the waveguide 906. The CW operation persists as long as the rate of change of the length of the waveguide is not so rapid that changes of more than a quarter wavelength occur before the frequency of the propagation tuned oscillator (PTO) can respond. This restriction exemplifies one advantageous difference between the performance of a PTO and a Phase Locked Loop (PLL). Assuming the transducers are producing ultrasonic waves, for example, at 2.4 MHz, the wavelength in air, assuming a velocity of 343 microns per microsecond, is about 143 μ, although the wavelength within a waveguide may be longer than in unrestricted air.

In a pulse mode of operation, the phase detector measures a time of flight (TOF) between when an ultrasonic pulse is transmitted by transducer 902 and received at transducer 904. The time of flight determines the length of the waveguide propagating path, and accordingly reveals the change in length of the waveguide 906. In another arrangement, differential time of flight measurements (or phase differences) can be used to determine the change in length of the waveguide 906. A pulse consists of a pulse of one or more waves. The waves may have equal amplitude and frequency (square wave pulse) or they may have different amplitudes, for example, decaying amplitude (trapezoidal pulse) or some other complex waveform. The PTO is holding the phase of the leading edge of the pulses propagating through the waveguide constant. In pulse mode operation the PTO detects the leading edge of with an edge-detect receiver rather than a zero-crossing or transition as detected by a zero-crossing receiver used in CW mode.

It should be noted that ultrasound energy pulses or waves, the emission of ultrasound pulses or waves by ultrasound resonators or transducers, transmitted through ultrasound waveguides, and detected by ultrasound resonators or transducers are used merely as examples of energy pulses, waves, and propagation structures and media. Other embodiments herein contemplated can utilize other wave forms, such as, light.

Figure 10:
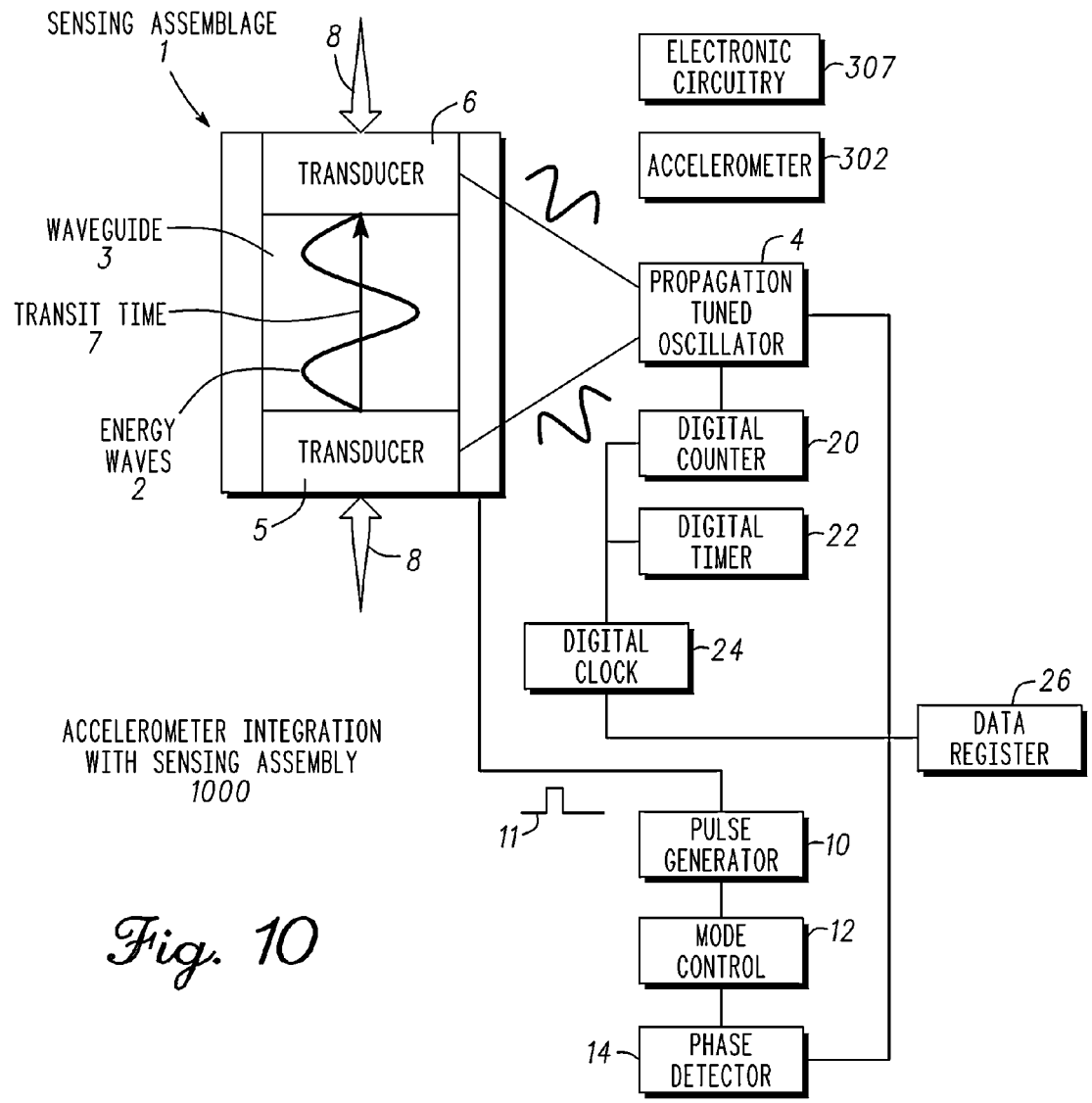
FIG. 10 is an exemplary block diagram of a propagation tuned oscillator (PTO) to maintain positive closed-loop feedback in accordance with an exemplary embodiment.

FIG. 10 is an exemplary block diagram 1000 of a propagation tuned oscillator (PTO) 4 to maintain positive closed-loop feedback in accordance with an exemplary embodiment. The measurement system includes a sensing assemblage 1 and propagation tuned oscillator (PTO) 4 that detects energy waves 2 in one or more waveguides 3 of the sensing assemblage 1. In one embodiment, energy waves 2 are ultrasound waves. A pulse 11 is generated in response to the detection of energy waves 2 to initiate a propagation of a new energy wave in waveguide 3. It should be noted that ultrasound energy pulses or waves, the emission of ultrasound pulses or waves by ultrasound resonators or transducers, transmitted through ultrasound waveguides, and detected by ultrasound resonators or transducers are used merely as examples of energy pulses, waves, and propagation structures and media. Other embodiments herein contemplated can utilize other wave forms, such as, light.

Recall that the sensing insert device 100 when in motion measures forces on the sensing assemblies by evaluating propagation times of energy waves within the waveguides in conjunction with the accelerometer data. The propagation tuned oscillator (PTO) 4 measures a transit time of ultrasound waves 2 within the waveguide 3 in a closed-loop configuration. The digital counter 20 determines the physical change in the length of the waveguide. Referring to FIG. 5, the one or more accelerometers 302 determines the changes along x, y and z dimensions. The electronic circuitry 307 in view of the accelerometer data from accelerometer 302 and the physical changes in length of the sensing assemblage 1 determines the applied loading (or forces).

The sensing assemblage 1 comprises transducer 5, transducer 6, and a waveguide 3 (or energy propagating structure). In a non-limiting example, sensing assemblage 1 is affixed to load bearing or contacting surfaces 8. External forces applied to the contacting surfaces 8 compress the waveguide 3 and change the length of the waveguide 3. Under compression, transducers 5 and 6 will also be moved closer together. The change in distance affects the transit time 7 of energy waves 2 transmitted and received between transducers 5 and 6. The propagation tuned oscillator 4 in response to these physical changes will detect each energy wave sooner (e.g. shorter transit time) and initiate the propagation of new energy waves associated with the shorter transit time. As will be explained below, this is accomplished by way of PTO 4 in conjunction with the pulse generator 10, the mode control 12, and the phase detector 14.

Notably, changes in the waveguide 3 (energy propagating structure or structures) alter the propagation properties of the medium of propagation (e.g. transit time 7). The energy wave can be a continuous wave or a pulsed energy wave. A pulsed energy wave approach reduces power dissipation allowing for a temporary power source such as a battery or capacitor to power the system during the course of operation. In at least one exemplary embodiment, a continuous wave energy wave or a pulsed energy wave is provided by transducer 5 to a first surface of waveguide 3. Transducer 5 generates energy waves 2 that are coupled into waveguide 3. In a non-limiting example, transducer 5 is a piezo-electric device capable of transmitting and receiving acoustic signals in the ultrasonic frequency range.

Transducer 6 is coupled to a second surface of waveguide 3 to receive the propagated pulsed signal and generates a corresponding electrical signal. The electrical signal output by transducer 6 is coupled to phase detector 14. In general, phase detector 14 compares the timing of a selected point on the waveform of the detected energy wave with respect to the timing of the same point on the waveform of other propagated energy waves. In a first embodiment, phase detector 14 can be a zero-crossing receiver. In a second embodiment, phase detector 14 can be an edge-detect receiver. In the example where sensing assemblage 1 is compressed, the detection of the propagated energy waves 2 occurs earlier (due to the length/distance reduction of waveguide 3) than a signal prior to external forces being applied to contacting surfaces. Pulse generator 10 generates a new pulse in response to detection of the propagated energy waves 2 by phase detector 14. The new pulse is provided to transducer 5 to initiate a new energy wave sequence. Thus, each energy wave sequence is an individual event of energy wave propagation, energy wave detection, and energy wave emission that maintains energy waves 2 propagating in waveguide 3.

The transit time 7 of a propagated energy wave is the time it takes an energy wave to propagate from the first surface of waveguide 3 to the second surface. There is delay associated with each circuit described above. Typically, the total delay of the circuitry is significantly less than the propagation time of an energy wave through waveguide 3. In addition, under equilibrium conditions variations in circuit delay are minimal. Multiple pulse to pulse timings can be used to generate an average time period when change in external forces occur relatively slowly in relation to the pulsed signal propagation time such as in a physiologic or mechanical system. The digital counter 20 in conjunction with electronic components counts the number of propagated energy waves to determine a corresponding change in the length of the waveguide 3. These changes in length change in direct proportion to the external force thus enabling the conversion of changes in parameter or parameters of interest into electrical signals.

The block diagram 1000 further includes counting and timing circuitry. More specifically, the timing, counting, and clock circuitry comprises a digital counter 20, a digital timer 22, a digital clock 24, and a data register 26. The digital clock 24 provides a clock signal to digital counter 20 and digital timer 22 during a measurement sequence. The digital counter 20 is coupled to the propagation tuned oscillator 4. Digital timer 22 is coupled to data register 26. Digital timer 20, digital timer, 22, digital clock 24 and data register 26 capture transit time 7 of energy waves 2 emitted by ultrasound resonator or transducer 5, propagated through waveguide 3, and detected by or ultrasound resonator or transducer 5 or 6 depending on the mode of the measurement of the physical parameters of interest applied to surfaces 8. The operation of the timing and counting circuitry is disclosed in more detail hereinbelow.

The measurement data can be analyzed to achieve accurate, repeatable, high precision and high resolution measurements. This method enables the setting of the level of precision or resolution of captured data to optimize trade-offs between measurement resolution versus frequency, including the bandwidth of the sensing and data processing operations, thus enabling a sensing module or device to operate at its optimal operating point without compromising resolution of the measurements. This is achieved by the accumulation of multiple cycles of excitation and transit time instead of averaging transit time of multiple individual excitation and transit cycles. The result is accurate, repeatable, high precision and high resolution measurements of parameters of interest in physical systems.

In at least one exemplary embodiment, propagation tuned oscillator 4 in conjunction with one or more sensing assemblages 1 are used to take measurements on a muscular-skeletal system. In a non-limiting example, sensing assemblage 1 is placed between a femoral prosthetic component and tibial prosthetic component to provide measured load information that aids in the installation of an artificial knee joint. Sensing assemblage 1 can also be a permanent component or a muscular-skeletal joint or artificial muscular-skeletal joint to monitor joint function. The measurements can be made in extension and in flexion. In the example, assemblage 1 is used to measure the condyle loading to determine if it falls within a predetermined range and location. Based on the measurement, the surgeon can select the thickness of the insert such that the measured loading and incidence with the final insert in place will fall within the predetermined range. Soft tissue tensioning can be used by a surgeon to further optimize the force or pressure. Similarly, two assemblages 1 can be used to measure both condyles simultaneously or multiplexed. The difference in loading (e.g. balance) between condyles can be measured. Soft tissue tensioning can be used to reduce the force on the condyle having the higher measured loading to reduce the measured pressure difference between condyles.

One method of operation holds the number of energy waves propagating through waveguide 3 as a constant integer number. A time period of an energy wave corresponds to energy wave periodicity. A stable time period is one in which the time period changes very little over a number of energy waves. This occurs when conditions that affect sensing assemblage 1 stay consistent or constant. Holding the number of energy waves propagating through waveguide 3 to an integer number is a constraint that forces a change in the time between pulses when the length of waveguide 3 changes. The resulting change in time period of each energy wave corresponds to a change in aggregate energy wave time period that is captured using digital counter 20 as a measurement of changes in external forces or conditions applied to contacting surfaces 8.

A further method of operation according to one embodiment is described hereinbelow for energy waves 2 propagating from transducer 5 and received by transducer 6. In at least one exemplary embodiment, energy waves 2 is an ultrasonic energy wave. Transducers 5 and 6 are piezo-electric resonator transducers. Although not described, wave propagation can occur in the opposite direction being initiated by transducer 6 and received by transducer 5. Furthermore, detecting ultrasound resonator transducer 6 can be a separate ultrasound resonator as shown or transducer 5 can be used solely depending on the selected mode of propagation (e.g. reflective sensing). Changes in external forces or conditions applied to contacting surfaces 8 affect the propagation characteristics of waveguide 3 and alter transit time 7. As mentioned previously, propagation tuned oscillator 4 holds constant an integer number of energy waves 2 propagating through waveguide 3 (e.g. an integer number of pulsed energy wave time periods) thereby controlling the repetition rate. As noted above, once PTO 4 stabilizes, the digital counter 20 digitizes the repetition rate of pulsed energy waves, for example, by way of edge-detection, as will be explained hereinbelow in more detail.

In an alternate embodiment, the repetition rate of pulsed energy waves 2 emitted by transducer 5 can be controlled by pulse generator 10. The operation remains similar where the parameter to be measured corresponds to the measurement of the transit time 7 of pulsed energy waves 2 within waveguide 3. It should be noted that an individual ultrasonic pulse can comprise one or more energy waves with a damping wave shape. The energy wave shape is determined by the electrical and mechanical parameters of pulse generator 10, interface material or materials, where required, and ultrasound resonator or transducer 5. The frequency of the energy waves within individual pulses is determined by the response of the emitting ultrasound resonator 4 to excitation by an electrical pulse 11. The mode of the propagation of the pulsed energy waves 2 through waveguide 3 is controlled by mode control circuitry 12 (e.g., reflectance or uni-directional). The detecting ultrasound resonator or transducer may either be a separate ultrasound resonator or transducer 6 or the emitting resonator or transducer 5 depending on the selected mode of propagation (reflectance or unidirectional).

In general, accurate measurement of physical parameters is achieved at an equilibrium point having the property that an integer number of pulses are propagating through the energy propagating structure at any point in time. Measurement of changes in the "time-of-flight" or transit time of ultrasound energy waves within a waveguide of known length can be achieved by modulating the repetition rate of the ultrasound energy waves as a function of changes in distance or velocity through the medium of propagation, or a combination of changes in distance and velocity, caused by changes in the parameter or parameters of interest.

It should be noted that ultrasound energy pulses or waves, the emission of ultrasound pulses or waves by ultrasound resonators or transducers, transmitted through ultrasound waveguides, and detected by ultrasound resonators or transducers are used merely as examples of energy pulses, waves, and propagation structures and media. Other embodiments herein contemplated can utilize other wave forms, such as, light. Furthermore, the velocity of ultrasound waves within a medium may be higher than in air. With the present dimensions of the initial embodiment of a propagation tuned oscillator the waveguide is approximately three wavelengths long at the frequency of operation.

Measurement by propagation tuned oscillator 4 and sensing assemblage 1 enables high sensitivity and high signal-to-noise ratio. The time-based measurements are largely insensitive to most sources of error that may influence voltage or current driven sensing methods and devices. The resulting changes in the transit time of operation correspond to frequency, which can be measured rapidly, and with high resolution. This achieves the required measurement accuracy and precision thus capturing changes in the physical parameters of interest and enabling analysis of their dynamic and static behavior.

These measurements may be implemented with an integrated wireless sensing module or device having an encapsulating structure that supports sensors and load bearing or contacting surfaces and an electronic assemblage that integrates a power supply, sensing elements, energy transducer or transducers and elastic energy propagating structure or structures, biasing spring or springs or other form of elastic members, an accelerometer, antennas and electronic circuitry that processes measurement data as well as controls all operations of ultrasound generation, propagation, and detection and wireless communications. The electronics assemblage also supports testability and calibration features that assure the quality, accuracy, and reliability of the completed wireless sensing module or device.

In general, measurement of the changes in the physical length of individual waveguides can be made in several modes. Each assemblage of one or two ultrasound resonators or transducers combined with a waveguide can be controlled to operate in six different modes. This includes two wave shape modes: continuous wave or pulsed waves, and three propagation modes: reflectance, unidirectional, and bi-directional propagation of the ultrasound wave. In all modes of operation the changes in transit time within the ultrasound waveguides change the operating frequency of the propagation tuned oscillator 4 or oscillators. These changes in the frequency of oscillation of the propagation tuned oscillator or oscillators can be measured rapidly and with high resolution. This achieves the required measurement accuracy and precision thus enabling the capture of changes in the physical parameters of interest and enabling analysis of the dynamic and static behavior of the physical system or body.

The level of accuracy and resolution achieved by the integration of energy transducers and an energy propagating structure or structures coupled with the electronic components of the propagation tuned oscillator enables the construction of, but is not limited to, compact ultra low power modules or devices for monitoring or measuring the parameters of interest. The flexibility to construct sensing modules or devices over a wide range of sizes enables sensing modules to be tailored to fit a wide range of applications such that the sensing module or device may be engaged with, or placed, attached, or affixed to, on, or within a body, instrument, appliance, vehicle, equipment, or other physical system and monitor or collect data on physical parameters of interest without disturbing the operation of the body, instrument, appliance, vehicle, equipment, or physical system.

Figure 11:
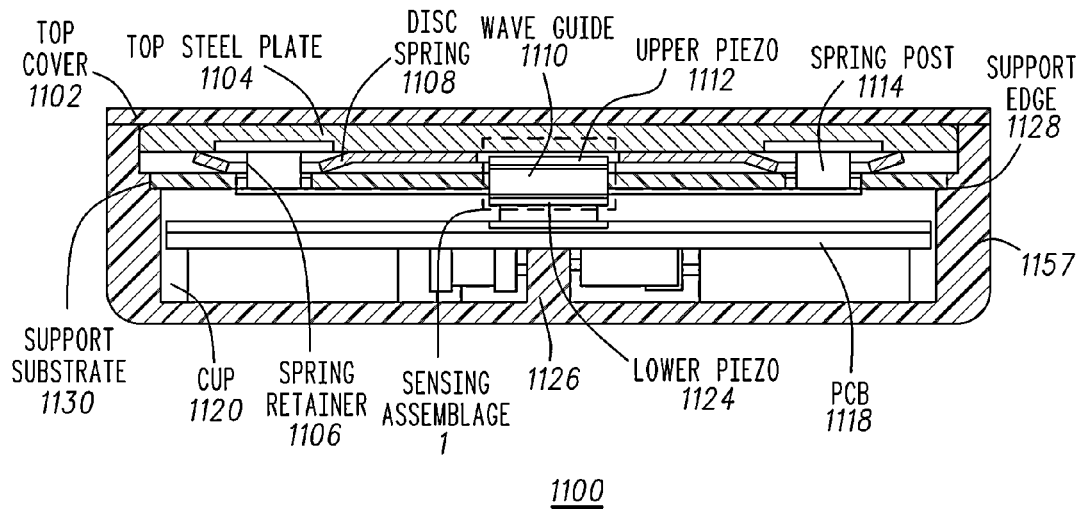
FIG. 11 is a cross-sectional view of a layout architecture of the sensing module in accordance with an exemplary embodiment.

FIG. 11 is a cross-sectional view of a layout architecture of the sensing module 200 in accordance with an exemplary embodiment. The blocks are operatively coupled within the encapsulated enclosure of the sensing module 200 and together form an encapsulated force sensor 1100. It comprises a top steel plate 1104 coupled to a lower printed circuit board (PCB) 1118 by way of spring retainer 1106, disc spring 1108, and spring post 1114. The force sensor 1100 is biased with springs, an elastic support structure or other means to accurately maintain a required distance between the load bearing or contact surfaces such as top cover 1102 and to minimize hysteresis due to material properties of waveguide 1110.

The encapsulating force sensor 1100 supports and protects the specialized mechanical and electronic components from external physical, mechanical, chemical, and electrical, and electromagnetic intrusion that might compromise sensing or communication operations of the module or device. The encapsulating force sensor 1100 also supports internal mechanical and electronic components and minimizes adverse physical, mechanical, electrical, and ultrasonic interactions that might compromise sensing or communication operations of the module or device. Top cover 1102 and unitary main body 1157 form the encapsulating enclosure. Unitary main body 1157 is a metal, plastic, or polymer body having sufficient strength and rigidity to withstand forces, pressures, and loads of the muscular-skeletal system. In particular, the sidewalls or bottom surface do not deform under normal operating conditions. For example, the unitary main body 1157 can be formed of polycarbonate or other biocompatible material. Moreover, unitary main body 1157 can be molded in a manufacturing process that allows detailed features to be repeatably and reliably manufactured.

The physical layout architecture of sensor 1100 has the one or more sensing assemblages overlying the electronic circuitry. A force, pressure, or load is applied to a surface of sensor 1100. The surface of sensor 1100 corresponds to top steel plate 1104. Steel plate 1104 moves in response to a force, pressure, or load. The steel plate 1104 can support the movement while maintaining a seal with unitary main body 1157 that isolates an interior of the enclosure. In general, a sensing assemblage is coupled between steel plate 1104 and a substrate 1130. Substrate 1130 is a rigid non-moveable substrate that is supported by the sidewalls of unitary main body 1157. A periphery of substrate 1130 is in contact with and supported by a support feature 1128 formed in the sidewalls of unitary main body 1157. Substrate 1130 does not flex under loading. The sensing assemblage translates a displacement due to the force, pressure, or load applied to steel plate 1104 to a signal.

The signal is processed by electronic circuitry in the enclosure to generate data corresponding to the force, pressure, or load value. As shown, the sensing assemblage comprises upper piezo 1112, waveguide 1110, and lower piezo 1124. Upper piezo 1112 and lower piezo 1124 are ultrasonic piezoelectric transducers.

Electronic circuitry to power, control, interface, operate, measure, and send sensor data is interconnected together on a printed circuit board (PCB) 1118. One or more cups 1120 are formed in unitary main body 1157. In one embodiment, the components mounted on PCB 1118 reside within cups 1120. One or more structures 1126 support and fix the position of the PCB 1118. The components on PCB 1118 are suspended in the cups 1120 and do not have contact with unitary main body 1157 thereby preventing interconnect stress that could result in long-term reliability issues. The PCB 1118 is mechanically isolated from substrate 1130. Thus, any force, pressure, or loading on substrate 1130 is not applied to PCB 1118. Flexible interconnect is used to connect from the electronic circuitry on PCB 1118 to upper piezo 1112 and lower piezo 1124.

In one embodiment, more than one sensing assemblage couples to predetermined locations of the steel plate 1104. Each sensing assemblage can measure a parameter applied to steel plate 1104. In combination, the sensing assemblages can determine a location or region where the parameter is applied to the surface. For example, the magnitude and position of the loading on the contacting surface of sensing module 200 applied by femur 102 and tibia 108 to sensing module 200 can be measured and displayed as shown in FIG. 2. In a non-limiting example, three sensing assemblages can be spaced on a periphery of steel plate 1104. In the example, each sensing assemblage will measure a force applied to steel plate 1104. The location of the applied force is closest to the sensing assemblage detecting the highest force magnitude. Conversely, the sensing assemblage detecting the weakest force magnitude is farthest from the applied force. The measured force magnitudes in combination with the predetermined locations where the sensing assemblages couple to steel plate 1104 can be used to determine a location where the parameter is applied.

The housing electrically insulates the internal electronic, sensing, and communication components. The encapsulating force sensor 1100 eliminates parasitic paths that might conduct ultrasonic energy and compromise excitation and detection of ultrasound waves within the sensing assemblages during sensing operations. A temporary bi-directional electrical interconnect assures a high level of electrical observation and controllability of the electronic assembly within the encapsulating force sensor 1100. The temporary interconnect also provides a high level of electrical observation of the sensing subsystem, including the transducers, waveguides, and mechanical spring or elastic assembly.

Ultrasound waveguide 1110 is coupled to the top cover 1102. A force applied to the top cover 1102 compresses waveguide 1110. Lower piezo 1124 and upper piezo 1112 are piezo-electric transducers respectively coupled to waveguide 1110 at a first and second location. Waveguide 1110 is a compressible propagation medium for ultrasonic energy waves. The transducers emit energy waves and detect propagated energy waves in waveguide 1110. Electronic circuitry is coupled to lower piezo 1124 and upper piezo 1112 to measure transit time, frequency, or phase of the propagated energy waves. The transit time, frequency, or phase of energy waves propagating between the first and second locations of waveguide 1110 can be precisely measured and therefore the length of the ultrasound waveguide 1110. The length of waveguide 1110 is calculated by a known function relating material properties of the waveguide 1110 to the parameter being measured. In the example, a force, pressure, or load is calculated from the measured length of waveguide 1110.

The encapsulated force sensor 1100 can accurately and repeatably measure one pound changes in load with changes in length of a waveguide comprising 2.5 microns. The maximum change in the present implementation is specified at less than 5.0 microns. This assures that the size of the sensing module 200 throughout all measurements remains within the required dimension (e.g., distance) of the insert between the load bearing surfaces of the prosthetic components.

An exemplary level of control of the compression or displacement of the waveguides 1110 with changes in load, force, pressure, or displacement is achieved by positioning the spring or springs 1108, elastic support structure, or other means of elastic support, including the waveguides 1110 themselves, between the load bearing contact surfaces to minimize any tendency of the load bearing contact surfaces to cantilever. Cantilevering can compromise the accuracy of the inclination of the load bearing contact surface whenever load, force, pressure, or displacement is applied to any point near a periphery of the load bearing contact surfaces. In one embodiment, springs 1108 are disc springs. The spring 1108 is held in a predetermined location by spring post 1114 and spring retainer 1104.

The walls of the unitary main body 1157 include a small gap to enable the steel plate 1104 to move. The hermetic seal is also flexible to allow the steel plate 1104 of the force sensor 1104 to slide up and down, like a piston, for distances on the order of a hundred microns without compromising integrity of the seal. The hermetic seal completes manufacturing, sterilization, and packaging processes without compromising ability to meet regulatory requirements for hermeticity. The level of hermeticity is sufficient to assure functionality and biocompatibility over the lifetime of the device. Implant devices with total implant time less than 24 hours may have less stringent regulatory requirements for hermeticity. Unbiased electrical circuitry is less susceptible to damage from moisture. The electronics in one embodiment are only powered during actual usage. In another embodiment, the encapsulated force sensor 1100 employs low duty cycles to serve as a measurement-on-demand device to efficiently perform at low total operating time when the electronics are powered on.

The encapsulating force sensor 1100 has a compact size permitting it to fit for example within a trial insert, final insert, prosthetic component, tool, equipment, or implant structure to measure the level and incidence of the load on subsequent implanted prosthetic devices. It can be constructed using standard components and manufacturing processes. Manufacturing carriers or fixtures can be designed to emulate the final encapsulating enclosure of the sensing module 200. Calibration data can be obtained during the manufacturing processing thus enabling capture of accurate calibration data. These calibration parameters can be stored within the memory circuits integrated into the electronics assemblage of the sensing module 200. Testability and calibration further assures the quality and reliability of the encapsulated enclosure.

Examples of a wide range of potential medical applications can include, but are not limited to, implantable devices, modules within implantable devices, intra-operative implants or modules within intra-operative implants or trial inserts, modules within inserted or ingested devices, modules within wearable devices, modules within handheld devices, modules within instruments, appliances, equipment, or accessories of all of these, or disposables within implants, trial inserts, inserted or ingested devices, wearable devices, handheld devices, instruments, appliances, equipment, or accessories to these devices, instruments, appliances, or equipment.

Figure 12:
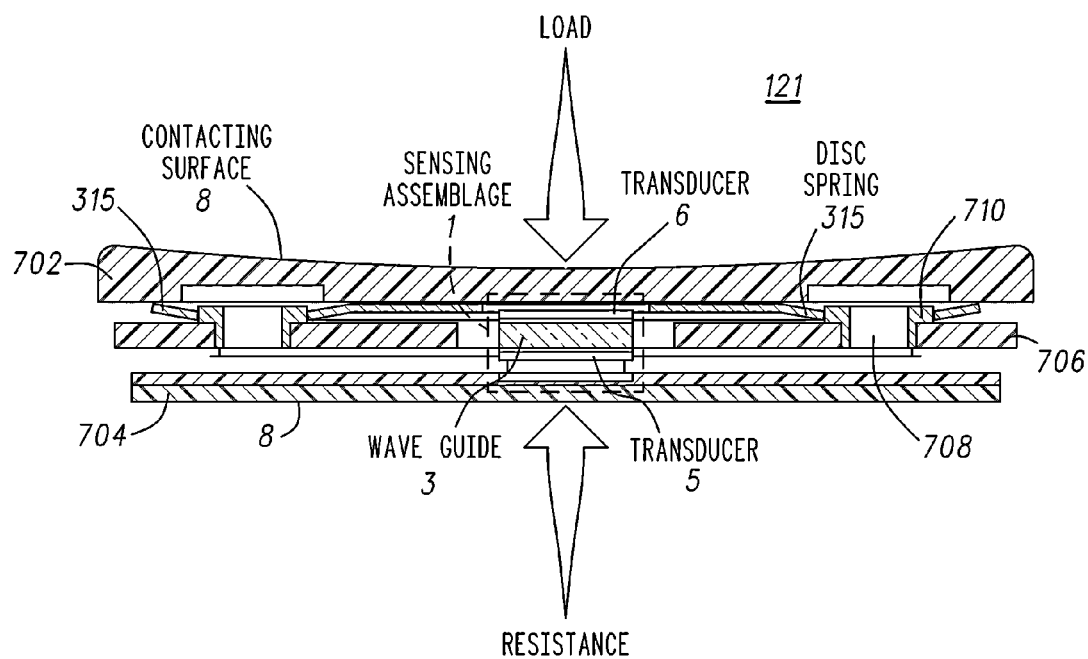
FIG. 12 is a simplified cross-sectional view of an embodiment of the load sensing platform in accordance with an exemplary embodiment.

FIG. 12 is a simplified cross-sectional view of an embodiment of the load sensing platform 121 in accordance with an exemplary embodiment. The load sensing platform 121 is placed, engaged, attached, or affixed to or within a physical system with a portion of the system contacting the load bearing or contacting surfaces of the load sensing platform 121. As disclosed in FIG. 1 the load sensing platform 121 can be used intra-operatively to measure parameters of the muscular-skeletal system during joint replacement surgery. In the example, the load bearing platform 121 is placed in a joint of the muscular-skeletal system to measure force, pressure, or load and the location where the force, pressure, or load is applied. The lower load bearing surface 8 contacts the tibial component 106 of the artificial knee. The upper load bearing surface 8 contacts the femoral component 104 of the artificial knee. Not shown are the muscles, ligaments, and tendons of the muscular-skeletal system that apply a compressive force, pressure, or load on the surfaces 8 of the load sensing platform 121. The load sensing platform 121 has a form factor that allows integration in tools, equipment, and implants. The load sensing platform 121 is bio-compatible and can be placed in an implant or attached to the muscular-skeletal system to provide long term monitoring capability of natural structures or artificial components.

A compact sensing platform is miniaturized to be placed on or within a body, instrument, appliance, vehicle, equipment, or other physical system without disturbing the operation of the body, instrument, appliance, vehicle, equipment, or physical system. This facilitates contacting the sources of load, force, pressure, displacement, density, viscosity, or localized temperature to be measured. The non-limiting example of load sensing platform 121 can include circuitry disclosed in FIG. 5. Two or more springs or other means of elastic support 315 support the load bearing or contacting surfaces 8. One or more assemblages each comprised of one or two ultrasound resonators or transducers are coupled between load bearing surfaces 8.

As shown, a single sensing assemblage 1 is centrally located in load sensing platform 121. Sensing assemblage 1 is a stack comprising the upper transducer 6, the lower transducer 5, and the waveguide 3. In one embodiment, the waveguide 3 is cylindrical in shape having a first end and a second end. Transducers 5 and 6 respectively overlie the first and second ends of waveguide 3. An interface material can be used to attach and enhance acoustical coupling between a transducer and waveguide. The stack is positioned in contact with, attached, or coupled to the load bearing or contacting surfaces 8. Electrical interconnect such as a flex interconnect couples to terminals of transducers 5 and 6. The flex interconnect (not shown) electrically connects transducers 5 and 6 to electronic circuitry 307 of the sensing module 200.

The upper load bearing surface 8 is a surface of an upper substrate 702. An interior surface of the upper substrate 702 couples to transducer 6. Similarly, the lower load bearing surface 8 is a surface of a lower substrate 704. An interior surface of the lower substrate couples to the transducer 5. A load, force, or pressure applied across load bearing surfaces 8 can compress or lengthen waveguide 3. This arrangement facilitates translating changes in the parameter or parameters of interest into changes in the length or compression of the waveguide or waveguides 3 and converting these changes in the length or compression of the waveguide 3 or waveguides into electrical signals by way of transducers 5 or 6 thus enabling sensing assemblage 1 to sense changes in the physical parameters of interest with minimal disturbance to the operation of the external body, instrument, appliance, vehicle, equipment, or physical system. To achieve the required level of miniaturization, the length of the ultrasound waveguides 3 is on the order of 10 millimeters in length. The measurable resolution of compression or displacement of waveguide is on the order of sub-microns.

One or more springs 315 or other means of elastic support, support the load bearing or contacting surfaces 8. The one or more springs control a compression of load sensing platform 121. For example, waveguide 3 can comprise a polymer material suitable for energy wave propagation. In one embodiment, the polymer material changes dimension when a parameter to be measured is applied to waveguide 3. A relationship is known between the polymer material and a measured dimension. Changes in dimension are measured and the parameter calculated by way of the known relationship. The polymer material can exhibit mechanical hysteresis whereby the material in-elastically responds to changes in the applied parameter. In the example, the length of waveguide 3 responds to the force, pressure, or load applied across contacting surfaces 8. Moreover, the polymer material may not rebound in a timely fashion as the force, pressure or load changes. Springs 315 aid in the transition as waveguide 3 responds to different levels of compression. Springs 315 bring the load sensing platform 121 to an accurate and repeatable quiescent state or condition. Springs further prevent the cantilevering of load bearing surfaces 8 that can reduce an accuracy of measurement. Cantilevering becomes more prevalent as forces, pressures, and loads are applied towards the periphery of a contact area of load bearing surfaces 8.

In one embodiment, the springs 315 that support load bearing surfaces 8 are disc springs or a wave springs. Disc springs are capable of maintaining waveguide 3 at a precise length. The compression of the waveguide 3 is very accurate over the measurement range. The compression of the disc springs can be monotonic over the range of applied levels of force, pressure, or load. In one embodiment, the surfaces of the disc springs are polished to assure smooth compression with changes in force applied to contact surfaces 8. A further benefit of the disk springs is that they eliminate or minimize cantilevering of the load supporting substrate that can compromise the accuracy due to the inclination of load bearing surfaces 8. In the illustration, two springs 315 are shown that are located on the periphery of load sensing platform 121. Although not shown, other springs 315 may reside in the load sensing platform 121 at other predetermined locations. Typically, the contact area where the parameter is applied to load bearing surfaces 8 is within an area bounded by springs 315.

In one embodiment, a substrate 706 is resides between upper substrate 702 and lower substrate 704. Sensing assemblage 1 couples through an opening in substrate 706 to couple to the interior surfaces of substrates 702 and 704 to measure a force, pressure, or load applied across load bearing surfaces 8. In the example, substrate 702 moves as a force, pressure, or load is applied while substrate 704 remains in a fixed position. Thus, a force, pressure, or load applied to contacting surface 8 changes a distance between substrates 702 and 704 and therefore the length of waveguide 3. Substrates 704 and 706 are planar to one another separated by a predetermined spacing. Substrates 704 and 706 remain in the fixed relation to one another under loading.

Springs 315 are placed between an upper surface of substrate 706 and the interior surface of substrate 702. As disclosed in the example, springs 315 are disc springs. The disc springs are concave in shape. The disc spring is formed having a centrally located circular opening. The surface of springs 315 proximally located to the circular opening contacts the upper surface of substrate 706. The surface of springs 315 proximally located to the outer edge of springs 315 contacts the interior surface of substrate 702. A force applied across the load bearing surface 8 of load sensing platform 121 will compress springs 315 and waveguide 3. The amount of compression of waveguide 3 over a measurable range can be very small but will provide precision accuracy of the parameter. For example, waveguide 3 may be compressed less than a millimeter for a force measurement ranging from 5 to 100 lbs. In the example, the length of waveguide 3 is precisely measured using acoustic energy wave propagation. The measured length is then converted to the force, pressure, or load. The springs 315 support movement of the waveguide 3 upon a change in force, pressure, or loading. For example, springs 315 repeatably return the load sensing platform 121 to a precise quiescent state upon releasing an applied force. The characteristics of springs 315 are known over the measurement range of load sensing platform 121. The calculated measured value of the parameter can include compensation due to springs 315.

Spring 315 are in a fixed location in load sensing platform 121. The disc springs are located on the periphery of the load sensing platform 121. Spring posts 708 and spring retainers 710 are used to align and fix springs 315 in each predetermined location. Spring post 708 aligns substrate 702 to substrate 706. Spring post 708 and spring retainer 710 aligns to corresponding openings in substrate 706. In one embodiment, a cap of post 708 fits into a corresponding cavity of the interior surface of substrate 702. Spring retainer 710 is a sleeve that overlies post 708. Post 708 and spring retainer 710 couples through a corresponding opening in substrate 706. Spring retainer 710 has a lip that overlies and contacts the upper surface of substrate 706. The spring post 708 and spring retainer 710 couple through the opening in the disc spring. The edge of the opening rests against the edge of the lip of retainer 710 thereby retaining and holding spring 315 in the predetermined location. Spring 315 can move vertically allowing waveguide 3 to change length due to the parameter being applied to contact surfaces 8.

In one embodiment, load sensing platform 121 can locate a position where the parameter is applied on a load bearing surface. Locating the position can be achieved by using more than one sensing assemblages 1. In one embodiment, three sensing assemblages 1 couple to load bearing or contacting surface 8 at three predetermined locations. The parameter is measured by each sensing assemblages 1. The magnitudes of each measurement and the differences between measurements of the sensing assemblages 1 are compared. For example, the location of the applied parameter is closer to the sensing assemblage that generates the highest reading. Conversely, the location of the applied parameter will be furthest from the sensing assemblage that generates the lowest reading. The exact location can be determined by comparison of the measured values of each sensing assemblage in conjunction with knowledge of the predetermined locations where each assemblage contacts load bearing or contacting surface 8.

Figure 14:
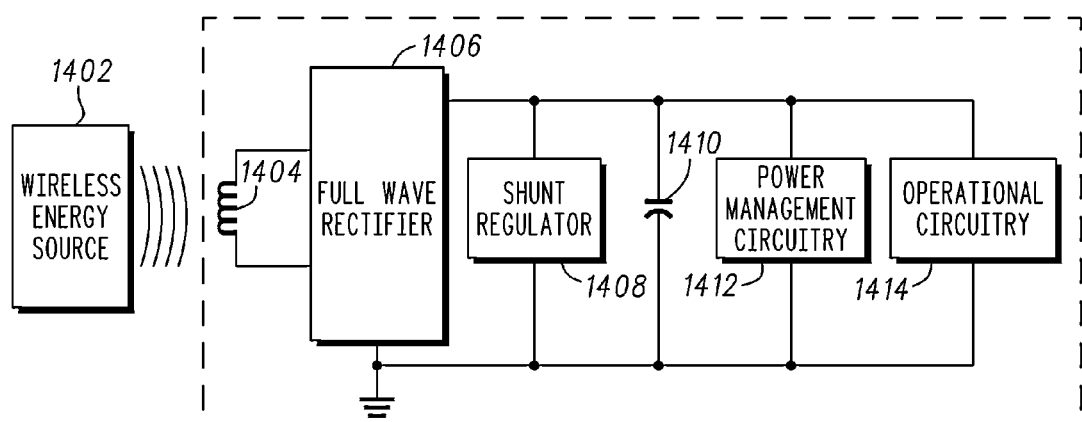
FIG. 14 is an exemplary block diagram schematic of a compact low-power energy source integrated into an exemplary electronic assembly of the sensing module in accordance with one embodiment.

FIG. 14 is an exemplary block diagram schematic of a compact low-power energy source 1400 integrated into an exemplary electronic assembly of the sensing module 200 in accordance with one embodiment. The schematic illustrates one embodiment of the capacitive energy storage 1400 having an induction coupling to an external power source 1402 to transfer energy to a super capacitor or capacitor as an energy storage device that provides operating power for sensing module 200. The compact low-power energy source 1400 can comprise an induction coil 1404, a rectifier 1406, a regulator 1408, a capacitive energy storage device 1410, a power management circuit 1412, and operational circuitry 1414. The latter circuits can be analog or discrete components, assembled in part or whole with other electronic circuitry, custom designed as an ASIC, or any combination thereof. In one embodiment, the operational circuitry can include circuitry to operate and produce measurement data from sensing assemblages, demodulation circuitry for a wireless receive path, communication circuitry, and secure encoding circuitry.

The external energy source 1402 can be coupled to a battery or batteries or an alternating current power supply. For example, external energy source 1402 can be an external hand-held device with its own battery that wirelessly transfers charge from the battery of the hand-held device to the energy source 1400 of the sensing device. The surgeon or technician can hold the hand-held device in close proximity to the sensing device prior to or during orthopedic surgery to provide sufficient charge to operate the device during the procedure. The sensing device as a long-term implant can be charged by the patient at his or her own convenience to initiate a measurement process that provides information on the implant status. In other embodiments, the sensing module 200 being powered by charge from external energy source 1402 can communicate a signal to indicate a recharging operation is necessary, for example, when in the proximity of a charging device.

External energy source 1402 can be coupled wirelessly to capacitive energy storage device 1410 through electromagnetic induction coil or coils 1404, rectifier 1406 and regulator 1408. The charging operation is controlled by power management circuitry 1412. During operation of operating circuitry 1414, power is transferred from capacitive energy storage device 1410 by power management circuitry 1412 that includes, but is not limited to, efficient step-up and step-down voltage converter circuitry that conserves operating power of circuit blocks at the minimum voltage levels that support the required level of performance. Clock frequencies are also optimized for performance, power, and size to assure digital circuit blocks operate at the optimum clock rates that support the required level of performance. Circuit components are partitioned among integrated circuits and discrete components to minimize power consumption without compromising performance. Partitioning functions between digital and analog circuit also enhances design flexibility and facilitates minimizing power consumption without sacrificing functionality or performance.

A method of powering and operation of the sensing module is disclosed below. The method can be practiced with more or less than the number of steps shown and is not limited to the order shown. To describe the method, reference will be made to the components of other figures described hereinabove although it is understood that the method can be implemented in any other manner using other suitable components. The sensing module 200 described in FIG. 5 including capacitive energy storage capability and highly efficient, low power operating performance can be used to illustrate the operating principles of the method. The method is initiated when the external power source 1402 begins transmitting power within range of the induction coil or coils 1404 of the sensing module 200. In a second step, the induction coils 1404 are coupled to the electromagnetic waves such that the electromagnetic waves are sensed. The induction coil or coils 1404 are energized by the power transmissions from external power source 1402. In a third step, the coupled electromagnetic waves create an AC power signal in induction coil or coils 1404. In a fourth step, the rectifier 1406 rectifies the AC power signal to produce a rectified power signal. In one embodiment, a voltage level across induction coil or coils 1404 rises to a level that a rectified signal is generated by full-wave rectifier 1406. In a fifth step, the rectified power signal is used to charge or provide energy to the capacitive energy storage device 1410, which holds the charge. In a non-limiting example, the energy storage device 1410 is a super capacitor or capacitor having a small form factor with enough storage capability to power the sensing module 200 for a predetermined period of time. For example, a total knee reconstruction operation takes approximately one to two hours. Capacitive energy storage device 1410 would store sufficient charge to power the sensing module 200 to provide measurements for this length of time. Integrating most of the circuitry on one or two low-power ASICs greatly reduces power consumption of the system making this possible. In a sixth step, the voltage regulator 1408 ensures that the capacitive energy storage device 1410 is charged to, and maintains a voltage level that is greater than the required operating voltage of the sensing module 200. In a seventh step, the power management circuitry 1412 monitors the level of charge on capacitive energy storage device 1410 to determine if the voltage exceeds a threshold. The threshold can correspond to a shunt threshold established by the regulator 1408. The operating electronics circuitry 1414 is enabled when it is determined in that an adequate level of charge has been stored to power the sensing module 200 for at least the predetermined time period.

In an eighth step, the power management circuitry 1412 disconnects the energy storage device 1410 from the charging circuitry (1404, 1406, and 1408) when the coupling with external power source 1402 is removed or terminated. Power management circuitry 1412 continues to monitor the level of charge on capacitive energy storage device 1410. The power management circuitry 1412 powers down the sensing module 200 including the operational circuitry 1414 when the charge or voltage level falls below a predetermined threshold. The power management circuitry 1412 subsequently discharges remaining charge on the energy storage device 1410 to prevent unreliable, intermittent, or erratic operation of the operational circuitry 1414.

Under nominal conditions, a charge time from zero charge to fully charged is approximately 3 minutes. In one embodiment, the maximum charge time is specified to be no greater than 7 minutes. The charging time of a capacitor powered system is a major improvement over the two hours or more required to fully charge a battery from zero charge regardless of battery capacity. The capacitive energy storage device 1410 can include capacitors with solid dielectrics that have longer lifetimes than batteries, can be left uncharged, and will not degrade regardless of length of time at a zero charge. In one arrangement, the wireless charging operation can be performed by electromagnetic induction before removal of any sterile packaging. The capacitive energy storage device 1410 is applicable for powering chronic active implantable devices where data collection is discrete point-of-time measurements rather than continuous, fulltime data collection and storage.

The compact low-power energy source can be used as a backup power source for sensing module 200 should the primary power source be terminated. A method performed by the compact low-power energy source as a backup power source is disclosed below. The method can be practiced with more or less than the number of steps shown and is not limited to the order shown. To describe the method, reference will be made to the components of FIGS. 1, 5 and 14, although it is understood that the method can be implemented in any other manner using other suitable components. The medical sensing device 100 described in FIG. 1 including capacitive energy storage capability and highly efficient, low power operating performance can be used to illustrate the operating principles of method as a back-up power source. Broadly stated, the method is directed to charging the sensing insert device 100 by way of a wired connection instead of wireless induction charging.

In a first step, the induction coil 1404 is electrically decoupled. In a second step, the rectifier 1406 and the regulator 1408 are disabled. At this juncture, the method enters a state where capacitive energy storage device 1410 is decoupled from the wireless charging circuits; that is, the power transmission components inductor 1404, rectifier 1406, and regulator 1408 are disabled. As one example, an electrical switching operation disengages the connection upon the power management circuitry 1412 detecting a direct line charge on the capacitive energy storage device 1410. In another arrangement, the power management circuitry 1412 further checks whether the induction coils are energized at the time of the applied line charge, thereby indicating that the energy is being delivered via a wired connection instead, since no induction activity by an external power source 1402 is detected.

In a second step, the wired energy source starts and charges capacitive energy storage device 1410. The wired energy source maintains capacitive energy storage device 1410 at full charge under normal operating conditions through direct electrical coupling. Power management circuitry 1412 monitors the level of charge on capacitive energy storage device 1410. If at a third step, power from wired energy source is interrupted, power management circuitry 1412 isolates the capacitive energy storage device 1410 from the wired energy source. As one example, a power interruption occurs when an individual manually disconnects the wired power source from the sensing module 200. This could also occur in response to an energy spike or power drop in the wired energy source. As another example, a power interruption could occur upon the power management circuitry 1412 detecting the presence of an external power source 1402 attempting to charge the sensing module 200 and thereby competing with the wired energy source.

In a fourth step, the power management circuitry 1412 can commence to supply the energy stored on the capacitive energy storage device 1410 to operating circuitry 1414 and associated electronics for normal operation. In a fifth step, power management circuitry 1412 monitors the level of charge on capacitive energy storage device 1410. In a sixth step, the power management circuitry 1412 will allow the continued supply of energy to the operating circuitry 1414 as long as the voltage on capacitor 1410 exceeds a voltage threshold. In a seventh step, the power management circuitry 1412 powers down the electronic assembly when the charge or voltage level falls below the predetermined charge of voltage threshold. The threshold is chosen to provide sufficient time to power down the operational circuitry 1414 in an orderly fashion.

If the wired energy source is restored, power management circuitry 1412 resumes the direct connection of power between the wired energy source and operational circuitry 1414. Power management circuitry 1412 also resumes the coupling of power between the wired energy source and capacitive energy storage device 1410 and resumes maintaining it at full charge.

A method is disclosed for wireless modulation telemetry in accordance with one embodiment. The method can be practiced with more or less than the number of steps shown and is not limited to the order shown. To describe the method, reference will be made to the components of FIGS. 1, 5 and 14, although it is understood that the method can be implemented in any other manner using other suitable components.

In a first step, the external wireless energy source 125 acquires input data. As one example, the user can manually enter the input data via a touchscreen or a user interface menu on the external wireless energy source 125. In another arrangement, the input data in response to a user directive can be communicatively uploaded to the external wireless energy source 125, for example, by USB or via a wi-fi connection. The input data can be information such as a serial number, a registration code, biasing parameters (e.g., spring constants, load balancing), updated parameters, version control information, security code information, data log tags, operational control information, or any other data. More specifically, data and instructions to be transmitted to the sensing insert device 100 is input into a data input port 128 of external wireless energy source 125.

As one example, referring back briefly to FIG. 1, the receiver station 110 can query a serial number from the sensing insert device 100 for updating medical records and inventory. Sensing insert device 100 includes the sensing module 200. As another example, the external wireless energy source 125 can download an operation code for adjusting a bias level of one of the springs in the sensing assemblies 303, or establishing an operating mode (e.g., standby, debug, flash). Following the acquisition of input data, the external wireless energy source 125 can be placed in the proximity of the load insert sensing device 100. At this point, operation of an external charging device or wireless energy source 1402 is initiated and contact is established with insert sensing device 100.

In a second step, the external wireless energy source 125 proceeds with secure encoding of the input data. As one example, the external wireless energy source 125 by way of a processor embeds cyclic redundancy check (CRC) bits into a data communication packet representing the input data. The CRC is computed and included in the transmission of each data packet. The cyclic redundancy check is based on an algorithm that computes a checksum for a data stream or packets of any length. These checksums can be used to detect interference or accidental alteration of data during transmission. Cyclic redundancy checks are good at detecting errors caused by electrical or electromagnetic noise and therefore enable robust protection against improper processing of corrupted data encoded in energy streams having communication of instructions and data as a secondary function.

In a third step, the external wireless energy source 125 modulates the input data onto a TX (transmit) power signal. For instance, the modulation circuit 127 modulates the power signal as a carrier signal and conveys the input data by adjusting at least one of an amplitude, phase, or frequency of the power signal. In the case of wireless energy transfer by resonant induction, the external wireless energy source 125 can modulate the resonant frequency over a small bandwidth to convey the input data in a power efficient manner. In yet another arrangement, timing intervals between energy emissions can be used to convey input data. In a fourth step, the external wireless energy source 125 transmits the TX power signal to the sensing insert device 100.

In a fifth step, the sensing insert device 100 senses the electromagnetic energy waves on the induction coils. In a sixth step, a RX power signal is generated from the received electromagnetic waves. This RX power signal comprises a power signal to provide charge to power to the sensing insert device 100 and a communication signal. As previously discussed, the compact low-power energy source 1400 by way of the induction coils 1404, rectifier 1406, and regulator 1408 sense and convert electromagnetic waves to a rectified voltage signal that is then used to charge a super capacitor or capacitor. In one configuration, the external wireless energy source 125 and the compact low-power energy source 1400 employ resonant inductive coupling to provide power efficient transmission over short distances (e.g., less than 20 cm). As an example, the inductors (coils) in conjunction with closely spaced capacitor plates are tuned to a mutual resonant frequency to minimize power loss. The external wireless energy source 125 modulates the power signal around the resonant frequency to transmit power efficiently while simultaneously conveying the communication signal.

In a seventh step, the sensing insert device 100 demodulates the communication signal from the RX power signal. The demodulation extracts the information or data from the modulated carrier wave. The demodulation circuit can be in one of the rectifier 1406, regulator 1408, power management circuitry 1412, or operational circuitry 1412. In an eight step, the sensing insert device 100 securely decodes and validates the information or data. In one embodiment, a cyclic redundancy check checksum is performed to verify the data was not corrupted or received incorrectly. The data is forwarded to control and processing circuitry 307. In the example, electronic circuitry 307 is on an ASIC integrated circuit with the communication blocks to perform the demodulation, CRC, encoding/decoding, and data validation. As an example, the circuitry can include envelope detectors, phase detectors, oscillators, multipliers, adders, filters, and logic operators.

The sensing insert device 100 can then proceed to use the decoded down-link data, for example, to control at least one operation, as shown in a ninth step. As an example, the control operation can place the sensing insert device 100 in a particular operation mode, such as, stand-by or low-power. As another example, the control operation can download a serial number to a local memory on the sensing insert device 100. The serial number can later be transmitted upon request to a communicatively coupled receiver station 110.

Methods are disclosed hereinbelow for power conservation in accordance with one or more embodiments. The methods can be practiced with more or less than the number of steps shown and is not limited to the order shown. To describe the method, reference will be made to the components of FIGS. 1, 5 and 14, although it is understood that the method can be implemented in any other manner using other suitable components. In general, a sensing module 200 is coupled to the muscular-skeletal system. The sensing module 200 is used intra-operatively to measure one or more parameters of the muscular-skeletal system to aid in the installation of prosthetic components. In the example disclosed above, the sensing module 200 is placed in a trial insert that dimensionally is substantially equal to the dimensions of a final insert. The trial insert is used in conjunction with other final or permanent prosthetic components to determine fit, function, and allowing modification to fine tune the installation before the final insert is inserted. Similarly, one or more of the final prosthetic components can include sensing module 200. The disclosed example has the sensing module 200 in the final insert. The sensing modules 200 in the final prosthetic components can measure different parameters than the trial insert. For example, pain, infection, joint kinematics, and bearing surface wear are post-operative parameters of interest.

In both the intra-operative and post-operative examples, the sensing module 200 has a form factor that is dimensionally smaller than a prosthetic component. In one embodiment, wired connections for power and communication are not used. In an intra-operative environment, wired connections can get in way of the procedure and limit surgical access. Internal implanted prosthetics such as knee, hip, spine, shoulder, and other joint implants cannot be wired unless terminals protrude through the skin. This is typically not desirable nor an effective long-term solution. The sensing module 200 can incorporate a battery as a temporary power source. As disclosed above, the battery poses the logistical problems of shelf life, installation, charging, and biological hazard. An alternative solution to a battery is using a super or ultra capacitor to power the sensing module 200. The capacitor has the benefits of form factor, long life, and fast charging time in a solid-state device.

The one limitation of a capacitor is the tradeoff of form factor and charge storage. A super or ultra capacitor having a form factor equal to or smaller than a watch battery or other small battery will typically have less energy capability than the battery. In an intra-operative procedure, such as a total knee reconstruction, the sensing module 200 has to deliver precision measurements throughout the surgery. A typical implant operation can last from one hour to several hours. Similarly, the sensing module 200 in a final prosthetic component would need to last a sufficient time to run through one or more measurements of one or more parameters. In both intra-operative and post-operative measurements, the measured parameter data would be sent wirelessly to the surgeon, patient, or healthcare provider. The measured data can be sent in real-time for display or delayed to be reviewed or analyzed at an appropriate time. In general, powering the sensing module 200 with a capacitor would not be a viable solution using off the shelf electronic components or sensors. A capacitor meeting the form factor requirements would not store sufficient charge to sustain device operation for a required operational period of time.

Sensing module 200 comprises a compact low-power energy source 1400 that includes the capacitor 1410 that powers the device during a measurement process. The capacitor 1410 is able to sustain operation of sensing module 200 by incorporating power management circuitry 1412 having one or more power conservation modes and an application specific integrated circuit (ASIC). The circuitry of sensing module 200 comprises operational circuitry 1414, charging circuitry, and power management circuitry 1412. The operational circuitry 1414 operates one or more sensing assemblages, controls measurement sequences, processes sensing assemblage data, and transmits information. The power management circuitry 1412 operatively couples to circuitry of compact low-power energy source 1400 and operational circuitry 1414 to controllably manage power efficiency of the system thereby enabling the use of the capacitor 1410 to power sensing module 200 for intra-operative and post-operative muscular-skeletal parameter measurements.

In one embodiment, the circuitry of sensing module 200 comprises at least one ASIC. The ASIC comprises the majority of the electronic system. The ASIC is architected to operate at low power and provide functionality to perform sensor measurements. In particular, the ASIC includes power management circuitry 1412, operational circuitry 1414, portions of compact low-energy source 1400, and can include wireless communication circuitry. The ASIC comprises complementary metallic oxide semiconductor (CMOS) circuitry that is low voltage and low leakage. The voltage operation is typically 5 volts or less. Voltage operation of analog circuitry can be higher. Digital circuitry can be operated at lower voltages such as 1-3 volts to further reduce power consumption. The ASIC provides a benefit of reduced form factor and low-power operation.

The ASIC is further configured in a block architecture. In particular, the operational circuitry 1414 is partitioned in a manner whereby functional blocks can be controlled by the power management circuitry 1412. A partitioned block, typically performs a function that is independent or not reliant on other blocks being operated and thereby can be turned on or off dependent on need to minimize power consumption. In particular, the power management circuitry 1412 can disable or delay operation of one or more functional blocks to reduce power consumption. In one embodiment, the power management circuitry 1412 makes these decisions based on monitoring the charge or voltage on the capacitor. The amount of charge or voltage can be used to determine when a block is enabled. Partitioning circuit components between structures within the integrated circuit and discrete components enhances design flexibility and minimizes power consumption without compromising performance. Partitioning functions between analog and digital circuitry also enhances design flexibility and facilitate minimizing power consumption without sacrificing functionality or performance.

In a first step, a highly efficient step-up or step-down voltage converter is implemented in the compact low-power energy source 1400. The step-up or step-down voltage converter circuitry enables essentially "lossless" translation of voltage levels. Further conservation of charge is achieved through selection of operating voltages and frequencies that meet device performance specifications. In a second step, reduction in power dissipation is achieved by operating circuitry at minimum frequencies and voltage. The clocking circuitry can be a significant source of power dissipation. Clock drivers can be optimized to efficiently drive a predetermined load. A clock tree or distributed clocking network can be used. The clock tree distribution is optimized in conjunction with the clock drivers to minimize delay and maintain timing at and between distributed nodes providing clock signals. In a third step, the clocked circuitry and the clock frequencies are optimized for power and sized to assure digital circuit blocks are each operated at the optimum clock frequency to achieve required performance with minimum power consumption.

Disclosed below are further exemplary embodiments to reduce power consumption of sensing module 200 that utilizes a temporary power source. The power management circuitry 1412 places the sensing module 200 in one or more power conservation modes depending on a current power status as disclosed below. In general, the ASIC can have multiple input and output channels. Each channel can have a dedicated function. For example, input channels can be used to couple to multiple sensors to measure different parameters of the muscular-skeletal system such as temperature, load, or pH. In a fourth step, the input-output channels are operated such that a single output channel or a single input channel is enabled at any point in time. Thus, the inputs or outputs are enabled sequentially or in sequence and are not operated in parallel to improve power efficiency. In a fifth step, a single input circuit and a single output circuit is used. This eliminates parallel input or output operation. The single input and single output circuit are multiplexed to the input-output channels. Typically, measurements of the muscular-skeletal system are not time constrained allowing sequential operation of the input-outputs to reduce peak power consumption. Furthermore, integrating only the single input circuit and the single output driver reduces the surface area of the integrated circuit as well as the amount of active circuitry thereby minimizing parasitic leakage paths.

In a sixth step, the architected design of the ASIC includes matching such that the input-output channels matches the input and output requirements of external signals. In the example, specific knowledge of the component characteristics is required to provide the match. In one embodiment, impedance matching produces an efficient energy transfer into and out of the ASIC thereby conserving power. For example, power efficient matching networks are used for coupling to telemetry, sensors, or transducers. The matching is accomplished with appropriate design of the outputs, drivers, and control circuitry within the ASIC that couple to off-board components and devices. In a seventh step, off-board sensors and transducers are also operated at optimum frequencies and drive voltages and currents to achieve the required performance of the wireless module or device at the minimum level of power consumption. Similarly, in an eighth step, operation of all circuit blocks, charging circuitry, and telemetry circuitry are each optimized for minimum total power consumption to achieve required performance levels. This includes, but is not limited to, timing of off and on states. This is coordinated to minimize power drain by optimizing timing and duty cycles of all individual circuit blocks including power drain when powered off plus power consumption to restart each circuit block versus standby power consumption of the separate circuit blocks.

The integration of design methods for ultra low power consumption achieves outstanding performance with minimum power drain. This enables highly performing wireless modules or devices powered by a capacitive energy storage device including, but not limited to, ultracapacitors, ultra capacitors, super-caps, super capacitors, or other capacitors. Furthermore, the power management circuitry 1412 can operate in one or more power conservations modes. In a first power conservation mode, the power management circuitry 1412 can turn off, disable, decouple, or disconnect circuitry not being used to conserve power. In a second power conservation mode, the power management circuitry 1412 decouples or turns off the compact low-power energy source 1400 thereby operating on power from capacitor 1410 when power management circuitry 1410 detects that wireless energy source 1402 cannot adequately provide energy or the wireless connection is unstable. In a third power conservation mode, the power management circuitry 1412 reduces a frequency of operation of one or more blocks in the ASIC to reduce operating power. In a fourth power conservation mode, the power management circuitry 1412 disables clock drivers of a clock tree coupled to circuitry not being used. In a fifth power conservation mode, the power management circuitry 1412 can place the operational circuitry in a sleep mode when the circuit is idle for a predetermined time. In a sixth power conservation mode, the power management circuitry 1412 allows parameter measurements to be taken and stored in memory. This can occur when the capacitor 1410 falls below a predetermined threshold. The parameter measurement data is delayed until to an appropriate time to conserve power. In a seventh power conservation mode, only a single input or single output of the ASIC is operated at any time. Finally, an orderly shutdown occurs to preserve parameter measurement data when the power management circuitry 1412 detects that the capacitor falls below a predetermined threshold. In general, the sensing module 200 can be powered by the capacitor 1410 as a result of the power conservation modes and power optimization thereby taking measurements for the duration of a total knee reconstruction. Benefits of the use of capacitors as a power source instead of, or in conjunction with, other power sources or rechargeable technologies include, but are not limited to, enabling a high level of miniaturization, solid state with no chemistries, almost infinite storage lifetime, storage with zero charge, quick charge times, and wireless charging.

Figure 15:
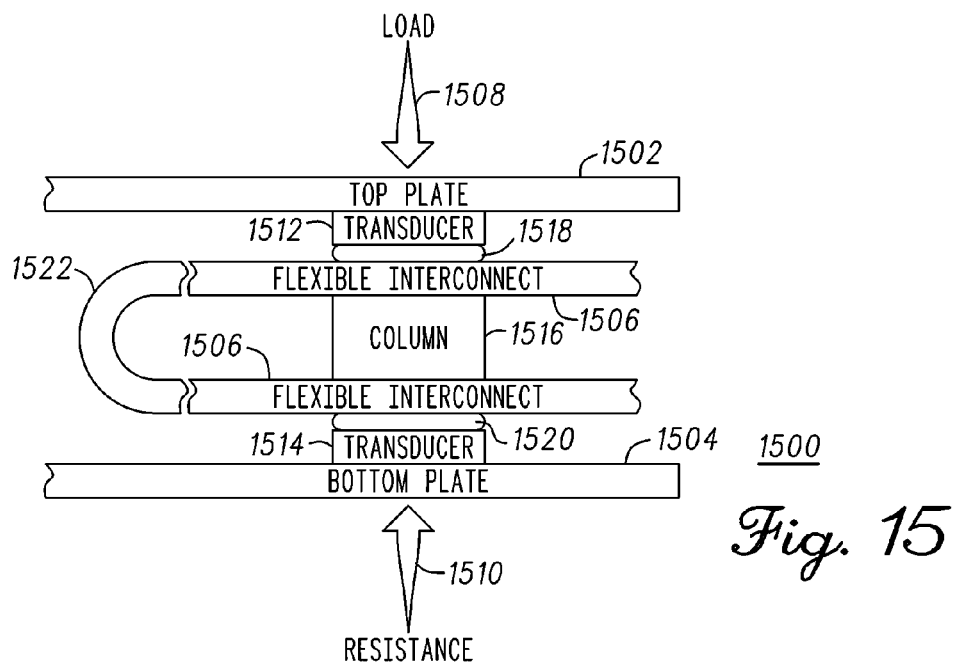
FIG. 15 is a partial cross-section schematic side view of a sensing platform including multiple constructed levels comprising electronic substrates with electronic components mounted thereon in accordance with an exemplary embodiment.

FIG. 15 is a partial cross-section schematic side view of a sensing platform 1500 including multiple constructed levels comprising electronic substrates with electronic components mounted thereon in accordance with an exemplary embodiment. In the non-limiting example, the sensing platform is used to measure a force, pressure, or load. It is a schematic image of components that fit together to make up an assemblage of transducers, interface materials, electrical interconnect, elastic columns, and mechanical structure using multiple electrical substrates.

A sensing assemblage comprises energy propagation medium 1516, transducer 1512, and transducer 1514. Energy propagation medium 1516 is positioned between transducer 1512 and 1514. In a non-limiting example, energy propagation medium 1516 is shaped as a column. Transducers 1512 and 1514 emit and detect energy waves that propagate through energy propagation medium 1516. Electronic circuitry coupled to transducers 1512 and 1514 detect changes and measure the transit time, frequency, or phase of the propagated energy waves by controlling the timing and duration. In the example, the transit time, frequency, or phase relates to a force, pressure, or load applied across a top plate 1502 and a bottom plate 1504. Typically, the bottom plate 1504 provides a resistance 1510 and the load 1508 is applied to the top plate 1502. In general, plates 1502 and 1504 provide mechanical support and can provide electrical interconnect to a transducer.

Flexible interconnect 1506 assures integrity of interconnect while allowing top plate 1502 to move when load 1508 is applied to the surface. The elastic strength of energy propagation medium 1516 contributes to supporting top plate 1502. The energy propagation medium further maintains a spacing between plates 1502 and 1504. Under a zero force or quiescent condition the distance between plates 1502 and 1504 are a predetermined distance. The sensing platform 1500 will repeatably return to this predetermined distance under a zero force or quiescent condition. The distance between plates 1502 and 1504 change as a function of the load 1508 applied to the top plate 1502. Flexible interconnect 1506 provides reliable electrical interconnect to the transducers 1512 and 1514 without restricting the compression or expansion of energy propagation medium 1516 or compromising the integrity of the quantification of the externally applied force, pressure, or load 1508.

In one embodiment, the transducer 1512 contacts an interior surface of top plate 1502. Similarly, the transducer 1514 contacts an interior surface of bottom plate 1504. Transducers 1512 and 1514 are positioned at a predetermined location on the interior surfaces of top plate 1502 and bottom plate 1504. The top plate 1502 and the bottom plate 1504 can comprise an electrically conductive material that can respectively be used as an interconnect to a terminal of transducer 1512 and transducer 1514. The flexible interconnect 1506 is routed to make electrical contact with transducers 1512 and 1514. The upper transducer 1512 or piezoelectric component has a conductive interface material or materials where required, solder or conductive adhesive, for electrical connection with flexible interconnect 1506. The lower transducer 1514 or piezoelectric component has a conductive interface material or materials where required, comprising solder or conductive adhesive 1520 for electrical connection with a second fold or portion of flexible interconnect 1506. Note, that the flexible interconnect includes a bend, fold, or arc 1522 to provide interconnect to different locations in the sensing assemblage. In the example, the sensing assemblage forms a stack comprising top plate 1502, transducer 1512, a first level of flexible interconnect 1506, energy propagation medium 1516, a second level of flexible interconnect 1506, transducer 1514, and bottom plate 1504. In this configuration, an energy wave couples through the flexible interconnect 1506. Moreover, the load 1508 is also applied through the flexible interconnect 1506 as part of the sensing assemblage. Under load 1508, the energy propagation medium is the only component of the stack that changes length.

Figure 16:
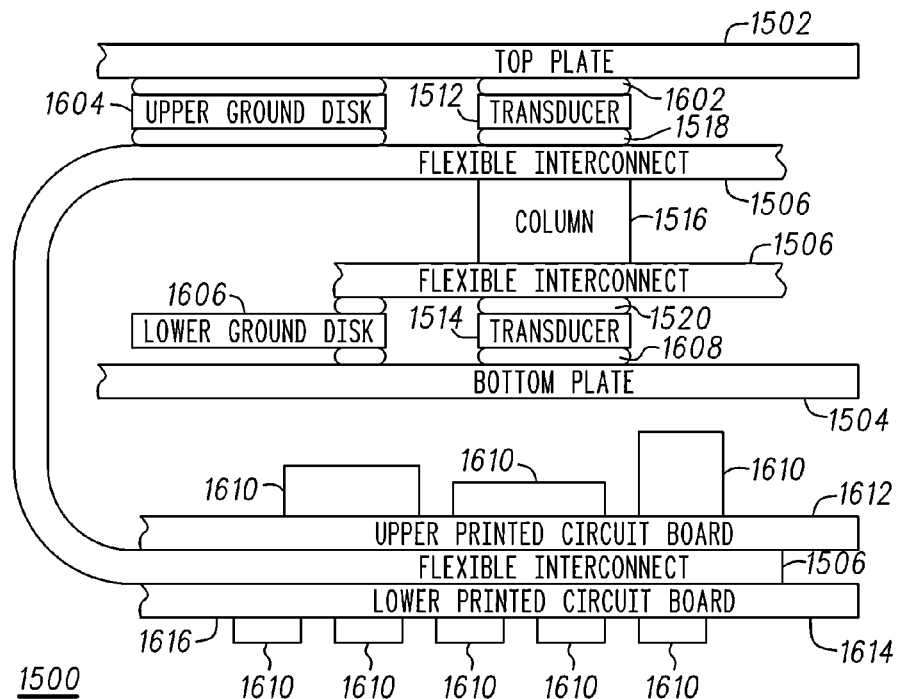
FIG. 16 is a partial cross-section schematic side view of the sensing platform including multiple constructed levels comprising electronic substrates with electronic components mounted thereon in accordance with an exemplary embodiment.

FIG. 16 is a partial cross-section schematic side view of the sensing platform 1500 including multiple constructed levels comprising electronic substrates with electronic components mounted thereon in accordance with an exemplary embodiment. The sensing platform 1500 has, in addition to the sensing assemblage or assemblages, printed circuit boards 1612 and 1616. Printed circuit boards 1612 and 1616 are populated with electronic components 1610. Electronic components 1610 comprise power source circuitry, power management circuitry, telemetry, and operational circuitry for performing parameter measurements. Electronic components 1610 are interconnected by interconnect formed on or within printed circuit boards 1612 and 1616. Electronic components 1610 are coupled to the sensing assemblage by flexible interconnect 1506.

In the embodiment, the sensing assemblage is between top plate 1502 and bottom plate 1504. The example sensing assemblage includes an upper transducer 1512 positioned in contact with top plate 1502 and a first side of energy propagation medium 1516. Similarly, the lower transducer 1514 is positioned in contact with bottom plate 1504 and a second side of energy propagation medium 1516. This can include conductive interface material or materials where required, solder or conductive adhesive 1602 and 1518 respectively for electrical interconnect with top plate 1502 and electrical contact with flexible interconnect 1506. The lower transducer 1514 has conductive interface material or materials where required, solder or conductive adhesive 1608 and 1520 respectively for electrical interconnect with bottom plate 1504 and with flexible interconnect 1506. Solder or conductive adhesive 1608 physically and electrically connect the components. An upper ground disk 1604 provides electrical connection between top plate 1502 and flexible interconnect 1506. The lower ground disk 1606 provides electrical connection between bottom plate 1504 and flexible interconnect 1506. An electrical circuit comprising electronic components 1610 and the sensing assemblages is completed by flexible interconnect 1506 that enables electronic components 1610 to operatively control transducers 1512 and 1514 to emit and detect energy waves into and propagating through energy propagation medium 1516.

The electronic components 1610 underlie bottom plate 1504. In one embodiment, bottom plate 1504 is a rigid substrate that isolates electronic components 1610 from any of the force, pressure, or load applied to the sensing platform. Having the one or more sensing assemblages overlying components 1610 provides a compact profile that allows a sensing module to have a form factor that can be fitted into a prosthetic component for the muscular-skeletal system. At least one printed circuit board is used to connect the electronic components 1610. In one embodiment, two printed circuit boards are implemented comprising a lower electronic circuit board 1616 and an upper electronic circuit board 1612. The flexible interconnect 1506 is routed to make electrical contact with the sensing assemblage, upper printed circuit board 1612 and lower printed wiring board 1616. The flexible interconnect 1506 is placed between and electrically connected to printed circuit boards 1612 and 1616 at predetermined locations. As mentioned previously, the sensing module can include transmit and receive capability. The sensing module can further include an antenna for the wireless communication. In one embodiment, an integrated antenna 1614 is formed on the lower printed circuit board 1616. As shown, the sensing module includes a stack of five or more layers of interconnect. The flexible interconnect 1506 comprises three levels of interconnect in the stack.

Figure 17:
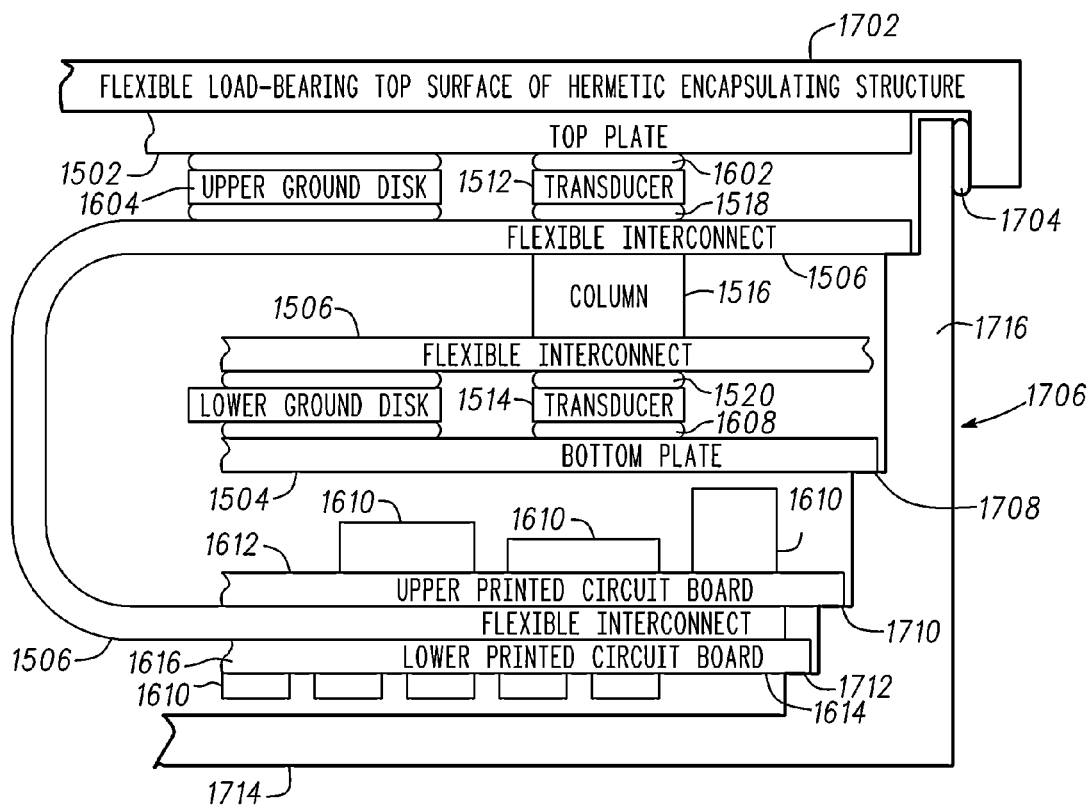
FIG. 17 is a partial cross-section schematic side view of a sensing module including multiple constructed levels comprising electronic substrates with electronic components mounted thereon in accordance with an exemplary embodiment.

FIG. 17 is a partial cross-section schematic side view of a sensing module 1700 including multiple constructed levels comprising electronic substrates with electronic components mounted thereon in accordance with an exemplary embodiment. In particular, the sensing module 1700 includes a housing 1706 and a cap 1702. The housing 1706 and cap 1702 form an encapsulating enclosure. The encapsulated enclosure houses sensing assemblages, electronic components, electrical interconnect, and mechanical structure using multiple electrical substrates and encapsulating structure as disclosed herein above. In one embodiment, the encapsulating enclosure is hermetically sealed.

The housing 1706 comprises sidewalls 1716 and a bottom surface 1714. Housing 1706 is made of a rigid material such as polycarbonate that can support the force, pressure, or load applied to the sensing module 1700 without flexing and is biocompatible. The interior of sidewalls 1716 include support features or ledges to suspend components at a predetermined height within housing 1706. Ledges 1708, 1710, and 1712 respectively support and retain bottom plate 1504, printed circuit board 1612, and printed circuit board 1616. The structures can be attached to the ledges by mechanical fastener, adhesive, or other attaching methodology. In one embodiment, the electronic components 1610 on printed circuit board 1616 face the bottom surface 1714 of housing 1706. The electronic components 1610 mounted on printed circuit board 1612 face the bottom plate 1504. The electronic components can be selected for each printed circuit board to minimize the combined height thereby reducing the form factor of sensing module 1700.

In one embodiment, an exterior surface of top plate 1502 extends above an upper surface of sidewalls 1716. The cap 1702 overlies top plate 1502 and the upper surface of sidewalls 1716. Cap 1702 includes a lip that extends over an exterior surface of sidewalls 1716. An adhesive 1704 is placed between the sidewall 1716 and the lip of cap 1702 to attach and seal the encapsulating enclosure. Thus, the sensing assemblage and electronic components 1610 are isolated from an external environment. In the example, a force, pressure, or load is applied to the exterior surface of cap 1702. The force, pressure, or load changes a length of energy propagation medium 1516. The change in length over the measurement range can be small. For example, energy propagation medium can change less than 5 millimeters to measure a range of 0 to 100 lbs of force. In other embodiments, the change in length can be substantially less than 5 millimeters depending on the material used for energy propagation medium 1516. The length change corresponds to the movement of cap 1702 and top plate 1502. Thus, cap 1702 and top plate 1502 are moveable structures in relation to housing 1706. The adhesive 1704 is chosen to allow this movement. For example, a silicone can be used as the adhesive, which is flexible and allows movement. The silicone will also seal the encapsulating enclosure. Alternatively, an o-ring can be used in place of adhesive 1706 as a mechanical solution that allows sealed movement. The transit time, frequency, or phase of propagated energy waves through medium 1516 is captured by electronic components 1610. The transit time, frequency, or phase can be converted to a length of energy propagation medium 1516, which is then related to the force, pressure, or load.

A method of electronic assembly is disclosed hereinbelow. The method can be practiced with more or less than the number of steps shown and is not limited to the order shown. To describe the method, reference will be made to the components of FIG. 17, although it is understood that the method can be implemented in any other manner using other suitable components. In a first step, the conductive interface material or materials are positioned in contact with or affixed to planar or conformal surfaces of each piezoelectric resonator or transducer. In a second step, the sensing assemblage or assemblages, having piezoelectric resonators or transducers 1512 and 1514 and are connected by conductive material or materials such as solder, conductive adhesive, conductive pre-forms, or conductive tape 1518, 1520, 1602, 1608 to flexible interconnect 1506, top plate 1502, bottom plate 1504, electronic components 1610, upper printed circuit board 1612 and lower printed circuit board 1616 thereby enabling electrical connection and mechanical robustness. Other conductive attaching techniques can be used such as attaching components with double-sided conductive tape or conductive epoxy. Adhesive tape that conducts electricity in the transverse direction only is another example of a conductive adhesive. Magnesium is an example of a potential interface material.

In a first variation, the flexible interconnect 1506 is routed to provide additional electrical interconnect to both faces of the transducers thus eliminating the requirement for multiple upper transducers or piezoelectric components to share a common electrical connection. Likewise, the requirement for multiple lower transducers or piezoelectric components sharing a common electrical connection can be eliminated by routing flexible interconnects to provide electrical contact to both faces of these components. This would require additional folds or segments of flexible interconnect. In a second variation, cap 1702 has an external surface that is non-planar or has a conformal surface. The integration of the non-planar or conformal surface or surfaces within the structure of the encapsulating enclosure 304 does not compromise the protective, hermetic, or mechanical support provided by the enclosure 304. In a third variation, an elastic support between top and bottom plates 1502 and 1504 is provided. The elastic support opposes the force, load, or pressure applied to the sensing module 1700. The elastic support provides greater flexibility in selecting the maximum force, pressure, or load 1508 that is quantified. In a fourth variation, the transducer 1512 in the sensing assemblage is replaced with a reflective surface or body and all signals propagating within the energy propagation medium is emitted and detected by transducer 1514. Using the reflective surface also eliminates top ground disk 1604. In a fifth variation, the sensing assemblage is a MEMS, piezo-resistive, mechanical, or strain gauge device coupled to flexible interconnect 1506.

Figure 18:
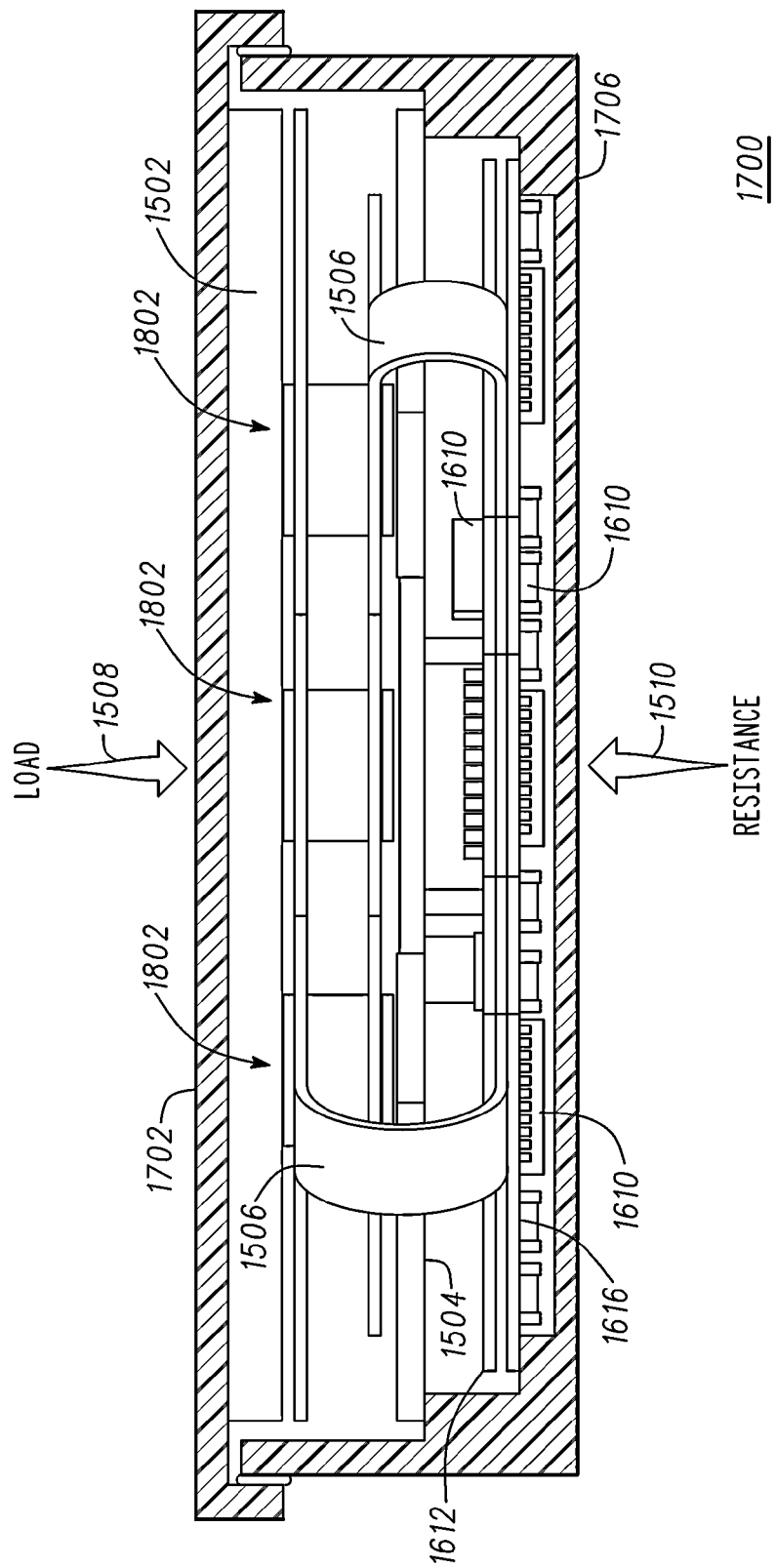
FIG. 18 is a cross-sectional view of the sensing module having a small form factor in accordance with an exemplary embodiment.

FIG. 18 is a cross-sectional view of the sensing module 1700 having a small form factor in accordance with an exemplary embodiment. In the example, the external pressure or load can be reliably detected and quantified by the interconnected sensing assemblages and electronic components without direct physical contact. Sensing assemblages 1802 comprises one or more transducers and a compressible propagation medium. Detail of the sensing assemblages 1802 is not visible in this view. Electronic components 1610 are affixed to the upper side of the upper printed circuit board 1612 and the lower side of the printed circuit board 1616 for mechanical support and electrical interconnect. The flexible interconnect 1506 couples the individual transducers 1512 and 1514 to the electrical components 1610 on the printed wiring boards 1612 and 1616 thus enabling complete electrical circuits for electrically stimulating and detecting electrical signals modulated by the energy propagating medium between transducers through the associated column. In particular, the illustrations shows two folds of the flexible interconnect 1506 that extend in an arc to two different levels of flexible interconnect running through the sensing assemblages 1802 that in one embodiment is part of the multi-layer interconnect stack.

The encapsulated sensing module or device 1700, as illustrated, comprises the cap 1702 of housing 1706 that encloses the electronic assemblage comprising sensing assemblages, interconnect, and electronic components. The top plate 1502 transfers flexor with changes in load 1508 of the load-bearing surface of the cap 1702 to the sensing elements of the sensing assemblages 1802. Mechanical support for electrical and mechanical components within the encapsulated sensing module 1700 is provided by features, ledges, and structures designed into the walls of the housing 1706.

Figure 19:
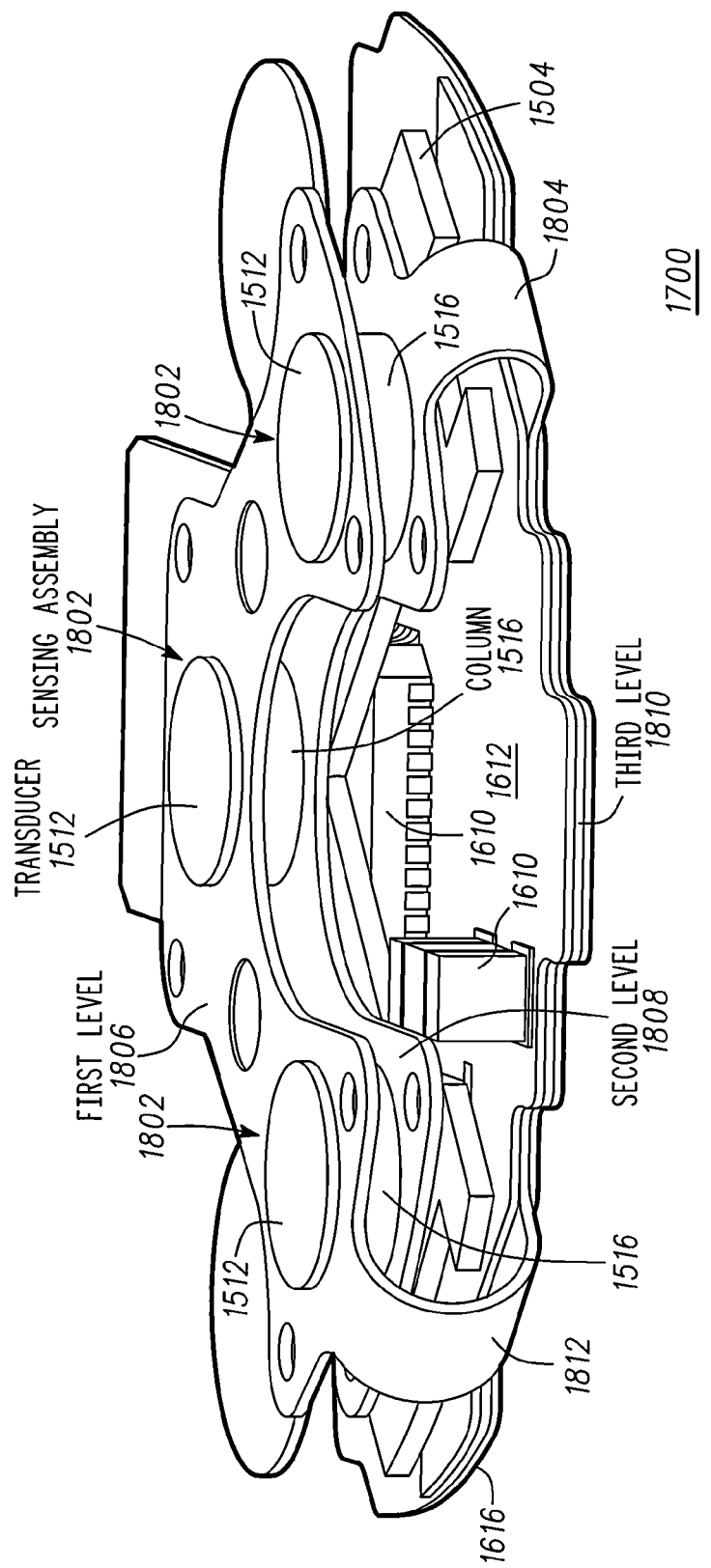
FIG. 19 is a perspective view of the interconnect stack of the sensing module in accordance with an exemplary embodiment.

FIG. 19 is a perspective view of the interconnect stack of the sensing module 1700 in accordance with an exemplary embodiment. In the embodiment, three assemblages 1802 couple to predetermined positions of the top plate 1502 (not shown). Multiple sensing assemblages 1802 are used to measure the force, pressure, or load and to identify where on the top plate 1502 (not shown) the parameter was applied. The location where the parameter is applied is determined by the magnitudes measured by each sensing assemblage 1802, the differential between the measurements, and the location where each sensing assemblage couples to top plate 1502 (not shown). The sensing module 1700 illustrates flexible interconnect supporting electronic components within the sensing assemblage or assemblages 1802. A single flexible interconnect comprises three levels of interconnection in the interconnect stack. A first level 1806 of the flexible interconnect is shown coupling between the transducers 1512 and corresponding energy propagation medium 1516. The first level of flexible interconnect 1806 includes a fold, bend, or arc 1812 that connects to a third level 1810 of the flexible interconnect. A second level 1808 of the flexible interconnect is shown coupling between energy propagation medium 1516 and the lower transducer 1514 (not shown). The second level 1808 of the flexible interconnect includes an arc 1804 that connects to the third level 1810 of the flexible interconnect. Note that both the first level 1806 and the second level 1808 includes interconnect that respectively connects to the three transducers 1512 and 1514. The third level 1810 of the flexible interconnect 1506 is between and connected to printed circuit boards 1612 and 1616. The printed circuit boards 1612 and 1616 include operational circuitry that couple to the sensing assemblages 1802 to generate parameter measurements from each sensing assemblage 1802. The upper and lower printed circuit, boards 1612 and 1616, flexible interconnect 1506, electronic components 1610, and bottom plate 1504 illustrate the spatial and mechanical relationships among the electrical substrates. The bottom plate 1504 is between the sensing assemblages 1802 and the electronic components 1610. It should be noted that in the embodiment, the flexible interconnect is part of the transmission path of the sensing assemblage. Energy waves transmit through the flexible interconnect into the energy propagation medium 1516. Similarly, propagated energy waves exiting the energy propagation medium 1516 transmit through the flexible interconnect to be detected by a transducer.

Figure 20:
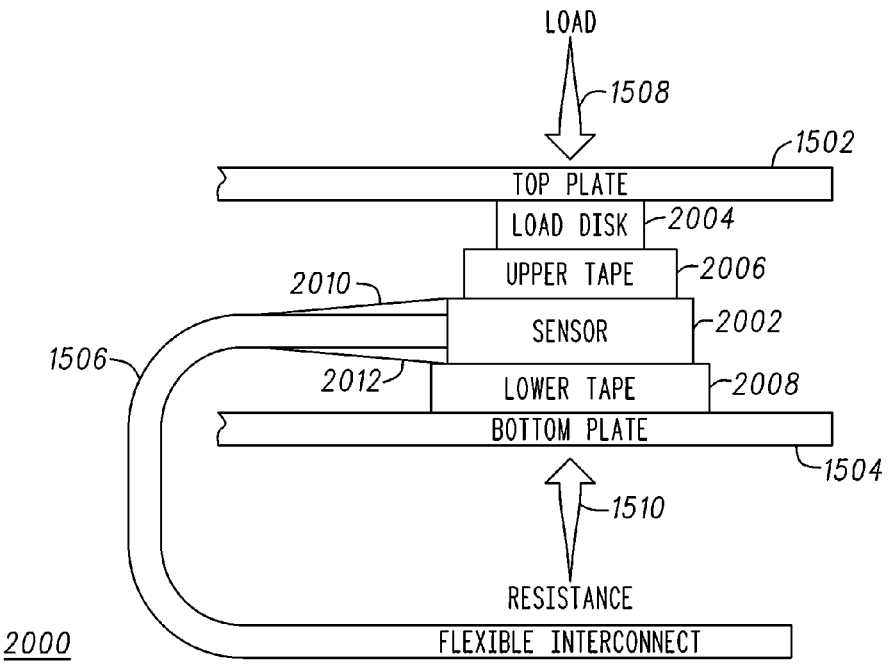
FIG. 20 is a partial cross-section schematic side view of a sensing platform including multiple constructed levels comprising electronic substrates with electronic components mounted thereon in accordance with an exemplary embodiment.

FIG. 20 is a partial cross-section schematic side view of a sensing platform 2000 including multiple constructed levels comprising electronic substrates with electronic components mounted thereon in accordance with an exemplary embodiment. It is a schematic image of components that fit together to comprise an integrated assembly having a sensor 2002 attached to flexible electrical interconnect 1506 and supported by top plate 1502 and bottom plate 1504 within an encapsulating enclosure as described hereinabove. The sensor 2002 replaces the sensing assemblage comprising transducer 1512, energy propagation medium 1516, and transducer 1514 shown in FIG. 15. In the embodiment, a thin film piezo-resistive sensor is used as sensor 2002 to measure the applied force, pressure, or load 1508. Piezo-resistive pressure sensors typically comprise a layer of pressure sensitive ink sandwiched between two conductive layers. The combination of conductive layers and pressure sensitive ink is encapsulated in a flat package with leads typically extending from a sidewall of the sensor. Sensor 2002 can have a thin form factor that reduces a height of the sensing module. Furthermore, piezo-resistive sensor 2002 is shaped in a manner that allows interconnect stacking. The sensor 2002 has a low level of conductance under a quiescent condition when no force, pressure, or load being applied to the piezo-resistive film. The quiescent condition can also be at a predetermined force, pressure, or load depending on the application. Applying a force, pressure, or load to the piezo-resistive film applies pressure to the ink layer. In the embodiment, the force, pressure, or load applied to top plate 1502 compresses the sensor 2002. The pressure on the ink increases the conductance as conductive particles are forced in contact or in proximity to each other. The more tightly they are compressed, the lower the resistance of sensor 2002. Conversely, as pressure is removed, the resistance of sensor 2002 returns to its quiescent state. The sensing platform 2000 can include an elastic structure (not shown) that returns the top plate to a precise position in relation to bottom plate 1504 after the force, pressure, or load is removed.

In one embodiment, the piezo-resistive sensing assemblage is a stack that comprises a load disk 2004, adhesive layer 2006, sensor 2002, and an adhesive layer 2008. The load disk 2004 is a spacer or column that is non-compressible or inelastic. The load disk 2004 can have a major surface that evenly distributes the force, pressure, or load across the major surface sensor 2002. The major surface of the load disk 2004 has a predetermined area for contacting the sensor 2002. Adhesive layer 2006 is non-conductive tape, adhesive, or other securing means that attaches load disk 2004 to sensor 2002. In the embodiment, the load disc 2004 is positioned respectively between top plate 1502 and bottom plate 1504. Adhesive layer 2008 is non-conductive tape, adhesive, or other securing means that attaches sensor 2002 to bottom plate 1504. Top plate 1502 transmits the level of force, pressure, or load 1508 externally applied to the top surface (not shown) of the encapsulated enclosure (not shown). The load disk 2004 then couples load 1508 from top plate 1502 to sensor 2002. The bottom plate 1504 is rigidly supported, through the mechanical structure of the encapsulating enclosure to maintain resistance 1510 to movement thereby enabling accurate quantification of the externally applied force, pressure, or load 1508.

In one embodiment, sensor 2002 has interconnect 2010 and 2012 that extends form the sidewall of the device. Interconnect 2010 and 2012 is connected to flexible interconnect 1506. Alternatively, sensor 2002 can have electrical contact terminals on either or both major surfaces that receive loading. In this embodiment, flexible interconnect 1506 would be part of the sensing assemblage stack between upper tape 2006, lower tape 2008, and sensor 2002 to make one or more connections. Moreover, the flexible interconnect 1506 would receive loading 1508 as part of the sensing assemblage. Current flow through upper interconnect 2010, sensor 2002, and lower interconnect 2012 is modulated by changes in force, pressure, or load 1508. This current flow is carried through traces on the surface of flexible interconnect 1506 to electronic circuitry (not shown) within the sensing module. Flexible interconnect 1506 provides reliable electrical interconnect to the one or more piezo-resistive sensing assemblages without restricting the transmission or compromising the integrity of the force, pressure, or load 1508 applied to the sensing module. In general, thin film piezo-resistive pressure sensors have benefits of simplicity, cost, power, form factor when compared to other sensing technologies. Interfacing with sensor 2002 and interpreting measurement data can reduce both mechanical and circuitry requirements thereby providing further benefit.

Figure 21:
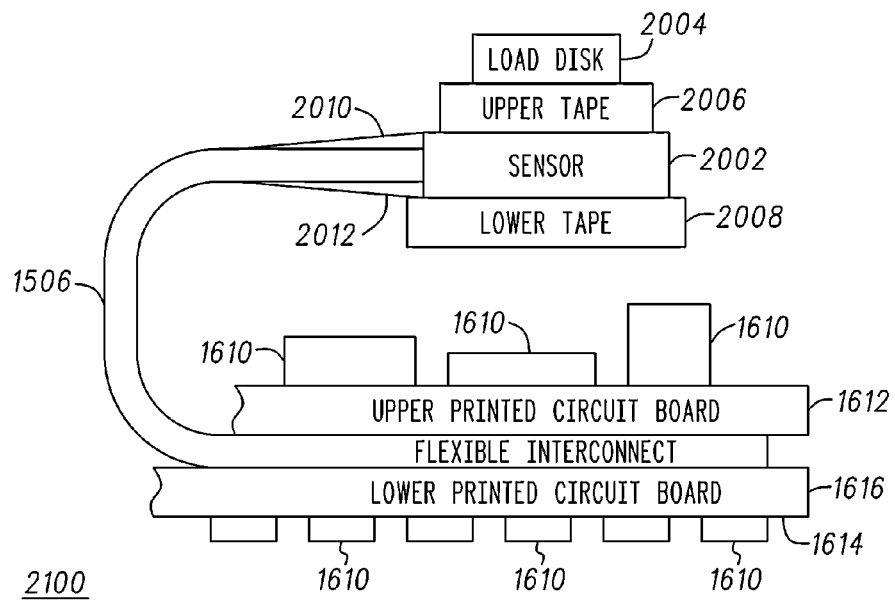
FIG. 21 is a partial cross-section schematic side view of the sensing platform including multiple constructed levels comprising electronic substrates with electronic components mounted thereon in accordance with an exemplary embodiment.

FIG. 21 is a partial cross-section schematic side view of the sensing platform 2000 including multiple constructed levels comprising electronic substrates with electronic components mounted thereon in accordance with an exemplary embodiment. The sensing platform 2000 has, in addition to the sensing assemblage or assemblages, printed circuit boards 1612 and 1616. Printed circuit boards 1612 and 1616 are populated with electronic components 1610. Electronic components 1610 comprise power source circuitry, power management circuitry, telemetry, and operational circuitry for performing parameter measurements. Electronic components 1610 are coupled to the sensing assemblage by flexible interconnect 1506. In one embodiment, using sensor 2002 in the sensing assemblage requires four layers of electrical interconnect.

The electronic components 1610 underlie bottom plate 1504 (not shown). In one embodiment, bottom plate 1504 is a rigid substrate that isolates electronic components 1610 from any of the force, pressure, or load applied to the sensing platform. Having the one or more sensing assemblages overlying components 1610 provides a compact profile that allows a sensing module to have a form factor that can be fitted into a prosthetic component for the muscular-skeletal system. At least one printed circuit board is used to connect the electronic components 1610. In one embodiment, two printed circuit boards are implemented comprising a lower electronic circuit board 1616 and an upper electronic circuit board 1612. The flexible interconnect 1506 is routed to make electrical contact with the sensing assemblage, upper printed circuit board 1612 and lower printed wiring board 1616. The electronic components 1610 detect and digitize changes in levels of the conductance of thin film piezo-resistive sensor 2002. The measured value of conductance can be converted to a force, pressure, or load value. The flexible interconnect 1506 is placed between and electrically connected to printed circuit boards 1612 and 1616 at predetermined locations. As mentioned previously, the sensing module can include transmit and receive capability. The sensing module can further include an antenna 1614 for the wireless communication. In one embodiment, the antenna 1614 is formed on the lower printed circuit board 1616. The antenna is a conductive trace on the printed circuit board 1616 formed in loop around the periphery. As shown, the sensing module includes a stack of four layers of interconnect. The flexible interconnect 1506 comprises has connections at two levels of interconnect in the stack.

Figure 22:
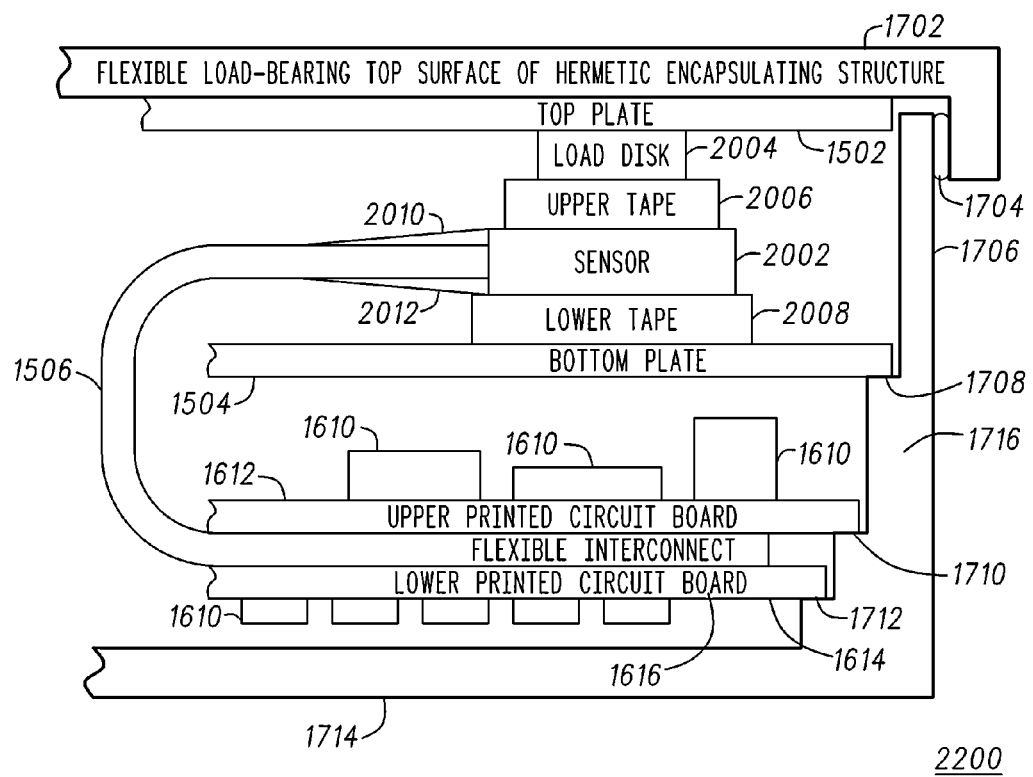
FIG. 22 is a partial cross-section schematic side view of a sensing module including multiple constructed levels comprising electronic substrates with electronic components mounted thereon in accordance with an exemplary embodiment.

FIG. 22 is a partial cross-section schematic side view of a sensing module 2200 including multiple constructed levels comprising electronic substrates with electronic components mounted thereon in accordance with an exemplary embodiment. In particular, the sensing module 2200 includes a housing 1706 and a cap 1702. The housing 1706 and cap 1702 form an encapsulating enclosure. The encapsulated enclosure houses sensing assemblages, electronic components, electrical interconnect, and mechanical structure using multiple electrical substrates and encapsulating structure as disclosed herein above. In one embodiment, the encapsulating enclosure is hermetically sealed.

The housing 1706 comprises sidewalls 1716 and a bottom surface 1714. Housing 1706 is made of a rigid material such as polycarbonate that can support the force, pressure, or load applied to the sensing module 1700 without flexing and is biocompatible. The interior of sidewalls 1716 include support features or ledges to suspend components at a predetermined height within housing 1706. Ledges 1708, 1710, and 1712 respectively support and retain bottom plate 1504, printed circuit board 1612, and printed circuit board 1616. In addition, support structures can be coupled from the bottom surface of housing 1706 for further support or as an option to the ledges. The structures can be attached to the ledges by mechanical fastener, adhesive, or other attaching methodology. In one embodiment, the electronic components 1610 on printed circuit board 1616 face the bottom surface 1714 of housing 1706. The electronic components 1610 mounted on printed circuit board 1612 face the bottom plate 1504. The electronic components can be selected for each printed circuit board to minimize the combined height thereby reducing the form factor of sensing module 1700.

In one embodiment, an exterior surface of top plate 1502 extends above an upper surface of sidewalls 1716. The cap 1702 overlies top plate 1502 and the upper surface of sidewalls 1716. Cap 1702 includes a lip that extends over an exterior surface of sidewalls 1716. An adhesive 1704 is placed between the sidewall 1716 and the lip of cap 1702 to attach and seal the encapsulating enclosure. Thus, the sensing assemblage and electronic components 1610 are isolated from an external environment. In the example, a force, pressure, or load is applied to the exterior surface of cap 1702. The force, pressure, or load is applied through top plate 1502 and load disk 2004 to sensor 2002. The housing 1706 and bottom plate 1504 provide a resistance against the force, pressure, or load thereby compressing the sensor 2002. The applied force, pressure, or load to the piezo-resistive film of sensor 2002 results in a corresponding change in resistance of the film. The electronic components 1610 couple to sensor 2002 through flexible interconnect 1506 forming a sensing circuit that detects a change in current or voltage as a result of a resistance change in the piezo-resistive material. The measured current or voltage directly corresponds to the force, pressure, or load. The measurement can be stored in memory or transmitted. It should be noted that the applied force, pressure or load causes movement of cap 1702 and top plate 1502. Thus, both are moveable structures in relation to housing 1706. The adhesive 1704 is chosen to allow this movement. For example, a silicone can be used as the adhesive, which is flexible and allows movement. The silicone will also seal the encapsulating enclosure. An o-ring could also be used in place of adhesive 1706 as a mechanical solution.

Figure 23:
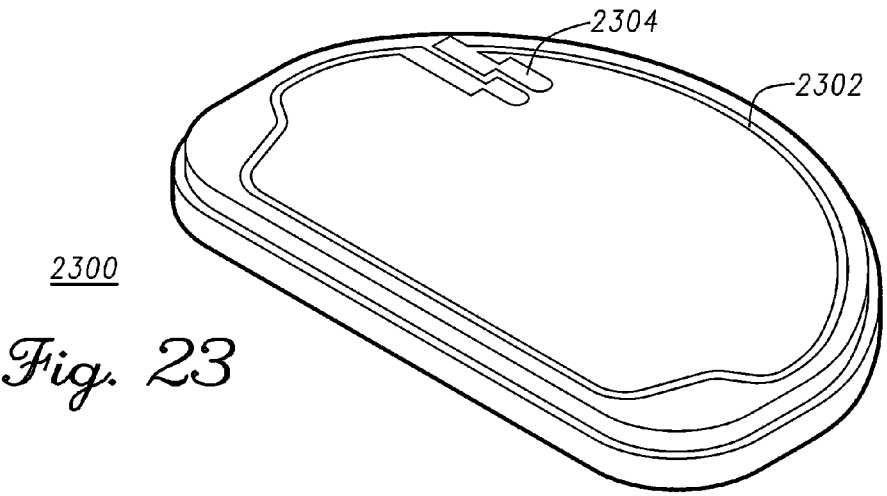
FIG. 23 is a perspective view of an exemplary loop antenna in accordance with one embodiment.

FIG. 23 is a perspective view 2300 of an exemplary loop antenna 2302 in accordance with one embodiment. As shown, the loop antenna 2302 is integrated along a periphery of the medical device to maximize the antenna trace length and exposure. In such an arrangement, the loop antenna 2302 radiates energy outwards along the circumference of the sensing module thereby enabling low-power operation when used in conjunction with a receiver placed in the vicinity of the sensing module. For instance, in the context of a load sensing insert device 100 used in knee implant surgery, the outer periphery is closest to the outside of the knee where a receiver device can be placed on the skin to scan the sensing module 200 for communication data. In this illustration, the loop antenna 2302 forms one or more loops along the outermost periphery of the encapsulated sensing module 200 as permitted by the encapsulated printed circuit board or electronic packaging substrate. A port 2304 includes two terminals that serve to couple the loop antenna 2302 to electronic components of the sensing module 200, such as the transceiver 320. The port 2304 can also couple external to the sensing module 200. The port 2304 couples to communication circuitry within the sensing module 200 and an antenna. In one embodiment, a matching network can be placed between transceiver 320 and antenna 2302 to improve efficiency. In an alternative embodiment, the loop antenna 2302 is formed on a flexible interconnect instead of a printed circuit board within the sensing module 200. The flexible interconnect couples the antenna 2302 to the communication circuitry and can include a bend that positions the loop antenna 2302 appropriately within the sensing module for transmission of data.

In another embodiment, the loop antenna 2302 is electrically coupled to the insert dock 202. The insert dock 202 is larger than sensing module 200 and has a larger peripheral area. A longer conducting antenna loop is formed in, on, or around the insert dock 202 for radio frequency communication. As an example, the insert dock 202 includes electrical wiring to serve as the loop antenna 2302. A hermetically sealed communications port resides on sensing module 200. As mentioned, the port 2304 couples to the communication circuitry and can be external to the sensing module 200. In one embodiment, port 2304 couples to the matching network. The external communication port on sensing module 200 connects to a corresponding port on the insert dock when inserted. The port or terminals on insert dock 202 connect to the antenna loop in or on the insert dock 202. In yet another arrangement, the insert dock 202 can comprise metal for being a conductor of radio communications.

Figure 24:
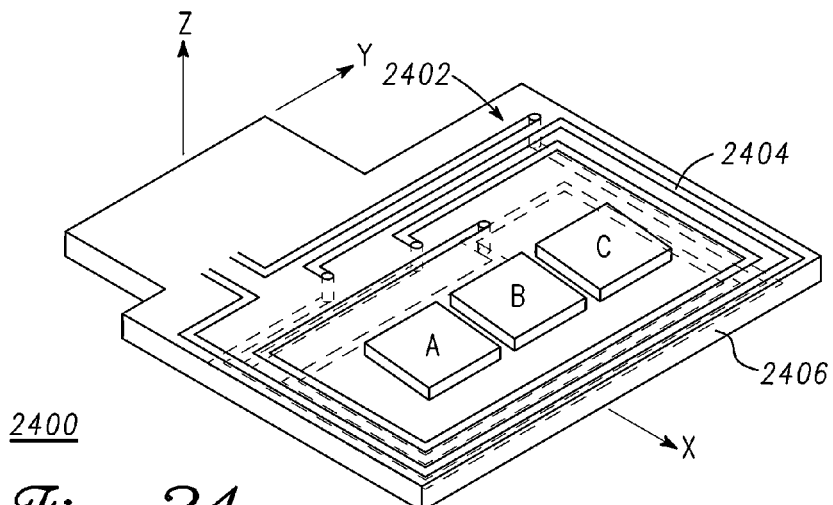
FIG. 24 is a perspective view of an integrated loop antenna according to another embodiment.

FIG. 24 is a perspective view 2400 of an integrated loop antenna 2402 according to another embodiment. As illustrated, the integrated loop antenna 2402 is integrated into a substrate of a printed circuit board 2406 of the sensing insert device 100. Other embodiments are not limited to the illustrated loop, or similarly shaped or functioning integrated loop antennas. As shown, the integrated loop antenna 2402 comprises circuit traces 2404 on a top (or bottom) layer of the substrate of the circuit board 2406. The traces 2404 act as a portion of the radiating and receiving body of the integrated loop antenna 2402. The circuit board 2406 can comprise multiple interconnect layers that can be formed as part of the radiating and receiving body, counterpoise, reflectors, or other structural components of the antenna 2402. The circuit traces 2404 can be etched to navigate around other electrical components and even the edge of the circuit board in certain embodiments.

Printed circuit technology supports the creation of many shapes of conductors and conducting surfaces on each layer of a multi-layer circuit board or flexible substrate. These conductors and conducting surfaces may be arranged and interconnected to function as radiating or receiving, reflection, and other surfaces of an integrated antenna. The conductors and conducting surfaces on each individual layer of the substrate may be interconnected in a variety of configurations. Conductors and conducting surfaces on each layer of the substrate may also be connected with conductors and conducting surfaces on other layers in a variety of configurations. This provides flexibility to design and integrate many forms of antennas with different radiation patterns, polarizations, frequency ranges, levels of Q, and impedance characteristics.

The circuit board 2406 comprises a matching network A, a radio frequency output stage B, and optional receiver circuit C. These block diagram components are functionally related to the transceiver 320 and electronic circuitry 307 of FIG. 5. The block models can comprise analog components, digital components, discrete components, integrated circuit components or any combination thereof. As shown, the circuitry is mounted on circuit board 2406. The matching network A provides impedance matching to an external receiver communications network to provide optimal power efficiency. The radio frequency output stage B drives the matching network A. The radio frequency output stage B amplifies and transmits communication signals to an external receiver. In the example, the communication signal will carry information that includes parameter measurement data such as load and balance measurements. The receiver circuit C is an optional component that can be integrated by way of switching (e.g., a Transmit-Receive (TR) switch) to receive data communications from an external transmitter, for example, to download a serial number.

The integration of the antenna 2402 into a rigid or flexible substrate for electronic circuits enables highly compact Radio Frequency (RF) modules, devices, instruments, or equipment with adequate radiating efficiency to operate at low power levels in many short-range applications. Integrated antennas have adequate receiving sensitivity for many of these applications as well. In one embodiment, the transmit power in conjunction with the loop antenna 2402 can be designed to limit the transmission distance. For example, it can restrict communication transmission to a distance corresponding to an operating room, doctor's office, or patient home thereby preventing or deterring others from receiving the measurement data. In one embodiment, the sensing module 200 is in an implant that would underlie tissue and portions of the muscular-skeletal system. In the embodiment, a portable receiver would be placed near the implant to receive or transmit information to the sensing module. These wireless modules, devices, instruments, or equipment may be constructed using high volume, low cost, standard manufacturing processes thus producing high quality, high reliability, deeply miniaturized radio frequency transmitter or receiver modules, devices, instruments, or equipment.

Integration of the antenna 2402 within the electronic assembly enables the construction of compact wireless equipment. In addition to a wide range of short-range handheld, wearable, or other portable communication equipment, many applications may also include data measurement, collection, and communication modules, devices, or equipment for a wide range of applications. Additional potential applications may include, but are not limited to, a wide range of medical applications. Potential medical applications may include, but are not limited to, intra-operative medical devices, trial inserts, and implants, other short-term medical devices, including devices that are inserted or ingested, other implanted medical devices, wearable medical devices, handheld devices, disposable medical devices or modules, medical instruments, medical equipment, accessories for medical instruments and equipment, and disposables associated with medical instruments, equipment, accessories.

Figure 25:
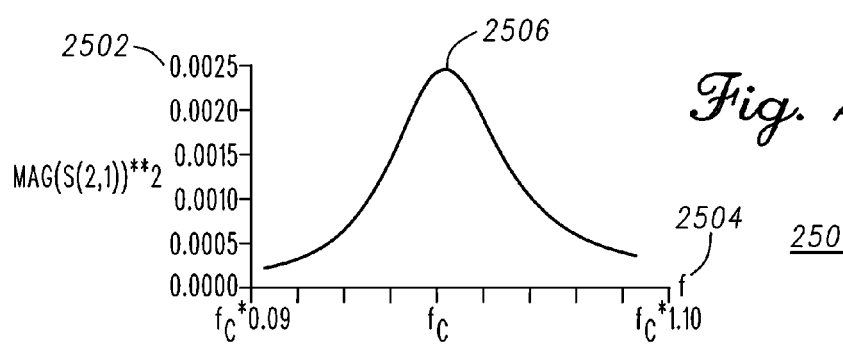
FIG. 25 Illustrates by way of example a plot of normalized radiated field strength versus frequency performance of an example loop antenna integrated into a flexible substrate of the electronic circuit board.

FIG. 25 Illustrates by way of example, a plot 2500 of normalized radiated field strength 2502 versus frequency 2504 performance of an example loop antenna integrated into a rigid or flexible substrate of the electronic circuit board. The plot 2500 illustrates radiation efficiency of the antenna and matching network from a circuit analysis. By way of electronic circuitry 307, the loop antenna can be configured to produce a frequency of maximum power output 2506. The electronic circuitry can further shape the peak (or radiation pattern) via a tuning mechanism to narrow (broaden) the peak and the relative Q level of the antenna. As one example, the electronic circuitry can emit a beacon signal over a broad frequency span, and upon receiving a ping for a particular communication channel, self-configure to narrow the peak to receive further communications under optimal power communication settings.

Figure 26:
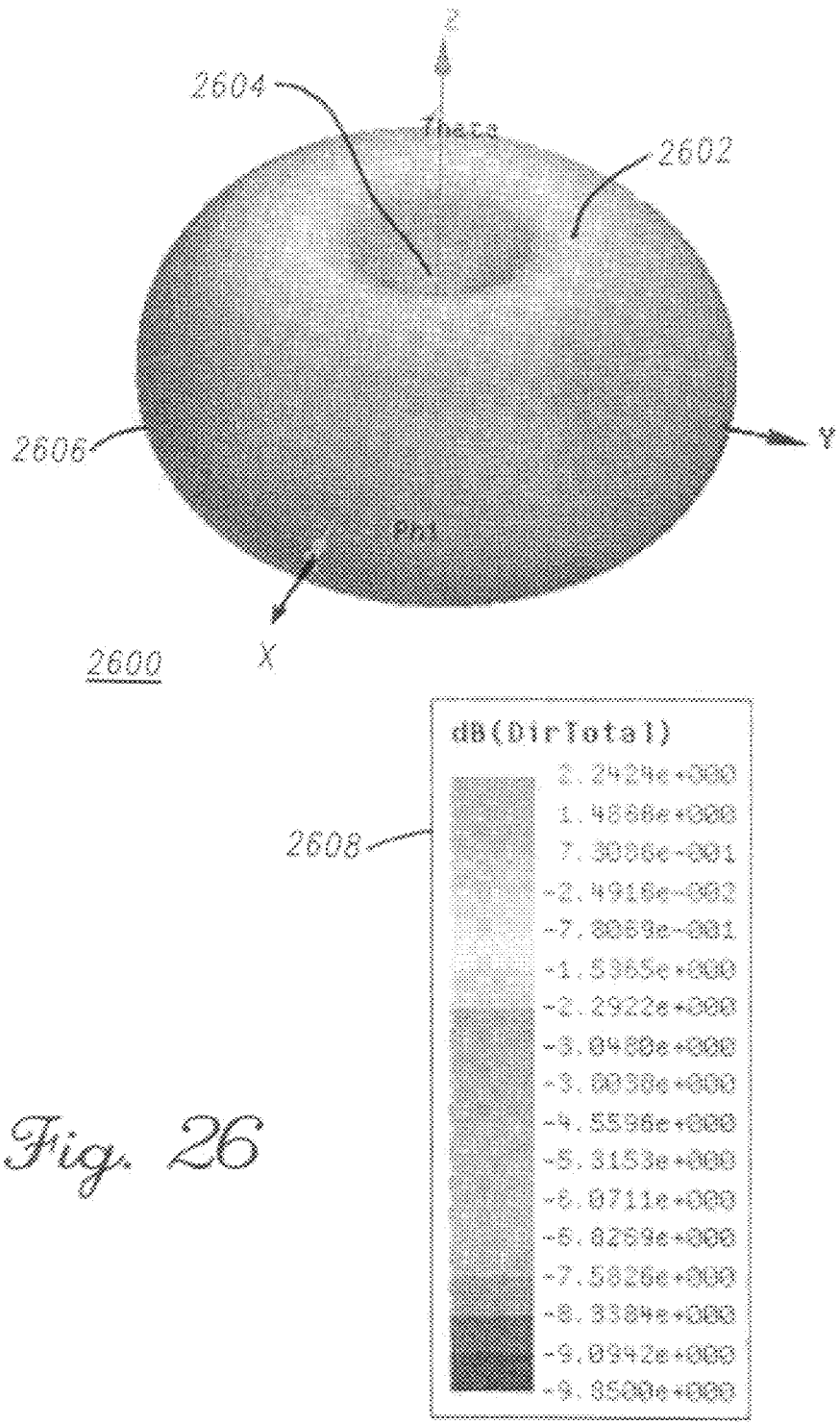
FIG. 26 Illustrates a radiation pattern of the loop antenna integrated into a flexible substrate of an electronic circuit in accordance with an exemplary embodiment.

FIG. 26 Illustrates a radiation pattern of the loop antenna integrated into a flexible substrate of an electronic circuit in accordance with an exemplary embodiment. The axes of the null points are readily visible and indicate that direction performance of reception and transmission can be well suited to applications where directional communications minimize the potential for inference. For instance, in the current antenna layout pattern, wherein the loop antenna is along an outer periphery, a radiation pattern is generated in a shape that propagates away from the implant site and in a direction, which facilitates acceptable signal to noise ratio (SNR). As shown, the null radiation lobes 2604 of the antenna pattern 2602 can be seen at positions where it may be less practical to place the receiver (e.g., along the femur or tibial axis), and that higher radiation lobes (or patterns) 2606 of the antenna pattern 2602 are along the outside periphery of the implant and are closest to the patient skin surface where a receiver can be placed. In other embodiments, the loop antenna can be physically configured, and in conjunction with control circuitry, to indicate a strong directional pattern of preferred reception and transmission thus making one particular instance of an integrated loop antenna well suited to applications that require omni-directional communications.

Figure 27:
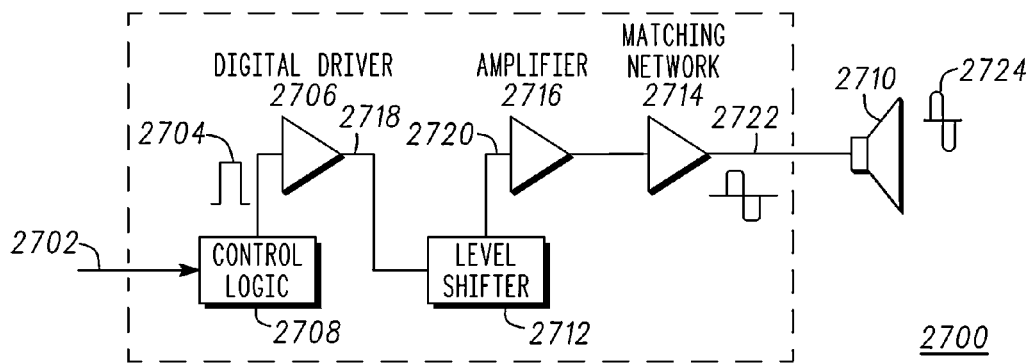
FIG. 27 illustrates a low power consumption integrated transducer driver circuit in accordance with an exemplary embodiment.

FIG. 27 illustrates a low power consumption integrated transducer driver circuit 2700 in accordance with an exemplary embodiment. In a first embodiment, driver circuit 2700 efficiently drives a transducer to generate time and frequency specific energy waves and pulses. It includes digital logic to generate drive signals according to the transducer characteristics and operational modes to achieve highly accurate control, timing, and duration of the generated energy waves and pulses. In one arrangement, the output driver is coupled to an ultrasonic sensing assembly to efficiently generate continuous ultrasonic waves or ultrasonic pulses that propagate through a propagation medium. The driver circuit includes a level shifter 2712 to raise or lower voltage levels of output pulses to voltage levels required to efficiently drive an energy emitting resonator or transducer given the characteristics of the resonator or transducer, the frequency and duration of the output waves, and the shape of the output pulse. It includes an impedance matching network 2714 to translate the digital output pulse into a required wave shape for efficiently and compactly driving the transducer. This configuration provides the benefit for battery or temporarily powered sensing systems to drive the energy emitting resonators or transducers with much less power consumption than a Digital to Analog Converter (DAC) based design.

In a second embodiment, the driver circuit 2700 is incorporated within a propagation tuned oscillator (PTO) to maintain positive closed-loop feedback. The PTO can operate in continuous wave mode, pulse-loop mode, pulse-echo mode, or controlled combination thereof. The driver circuit 2700 is electrically integrated with the PTO by multiplexing input and output circuitry, including off-board components of an impedance matching network, to achieve ultra low-power and small compact size. In this arrangement, off-board energy emitting resonators or transducers are operated at optimum frequencies and drive voltages and currents to achieve optimal performance at a minimum level of power consumption.

The drive circuit 2700 can singly drive multiple energy emitting resonators or transducers to achieve this level of performance; that is, only one driver circuit can be shared. Appropriate duty cycles and multiplexing timing for optimum frequencies of the energy emitting resonators or transducers are selected to conserve both power and space without compromising performance. This enables, but is not limited to, the design and construction of compact measurement modules or devices with thickness on the order of a few millimeters.

In one embodiment, low power consumption transducer driver circuit 2700 comprises control logic 2708, a digital driver 2706, level shifter 2712, an amplifier 2716, and matching network 2714. The driver circuit 2700 can be implemented in discrete analog components, digital components, an application integrated circuit, or a combination thereof. In a low power application, transducer driver circuit 2700 is integrated with other circuitry of the propagation tuned oscillator. Briefly, the transducer driver circuit 2700 accurately controls emissions of energy waves or pulses, and parameters thereof, including, but not limited to, transit time, phase, or frequency of the energy waves or pulses. A brief description of the method of operation is as follows.

An input 2702 receives a signal to emit an energy wave. Input 2702 couples to control logic 2708. Control logic 2708 controls the timing and frequency of stimulation of an energy transducer 2710. A digital pulse 2704 from digital control logic 2708 is provided to an input of driver 2706. In an energy pulse mode, digital control logic 2708 also controls the duration of the stimulation. One or more pulses from an output 2718 of driver 2706 are coupled to level shifting circuitry 2712. Level shifting circuitry 2712 adjusts the output voltage of driver 2706 to efficiently drive energy transducer 2710. One or more level shifted pulses are provided at an output 2720 of level shifter 2712 to amplifier 2716. Amplifier 2716 amplifies the signal at output 2720, which is provided, to an input of matching network 2714. Matching network 2714 matches the electrical characteristics of the energy transducer 2710. The output signal 2722 from the matching network 2714 enables energy transducer 2710 to emit an energy wave. Matching network 2714 converts the output pulse from amplifier 2716 to the required wave shape, frequency and phase. Transducer 2710 emits energy waves 2724 into the medium upon excitation by the signal output from matching network 2714.

As discussed above, the electronic components are operatively coupled as blocks of integrated circuits. As will be shown ahead, this integrated arrangement performs its specific functions efficiently with a minimum number of components. A portion of the efficiency is achieved because the circuit components are partitioned between structures within an integrated circuit and discrete components, as well as innovative partitioning of analog and digital functions, to achieve the required performance with a minimum number of components and minimum power consumption.

Briefly, an input of digital driver 2706 is driven by digital control logic 2708, which ultimately controls the timing and frequency of the resulting output signal 2722. As will be shown ahead, the output signal 2722 drives an energy transducer 2710 to output an energy wave or energy pulse. The drive circuit 2700 is optimally configured to generate the output signal 2722 according to the transducer characteristics (e.g., frequency, stiffness, Q, ringing, inductance, ringing, decay, feedback) and in certain cases the operating mode (e.g., continuous, pulse-loop, and pulse echo). For example, in pulse-loop mode, digital control logic 2708 also controls the duration of the transducer 2710 stimulation. Level shifter 2712 adjusts the output voltage of driver output 2706 to efficiently drive energy transducer 2710. More specifically, the level shifter 2712 raises or lowers voltage levels of output pulses to the voltages required to efficiently drive the energy emitting resonator or transducer 2710 given the characteristics of the resonator or transducer 2710, the frequency and duration of the output waves, and the shape of the output pulse. Matching network 2714 matches the electrical characteristics of the energy transducer 2710 and converts the output pulse 2722 to the required wave shape, frequency and phase. The generated digital output waveform 2722 or pulse may have a moderately sharp leading edge.

With regard to the integrated transducer driver 2700, efficient use of power and conservation of charge is required for ultra low power operation. Energy emitting resonators or transducers 2710 can be stimulated with a sine wave or other form of continuous wave to efficiently emit energy waves of the required frequency, phase, and duration. Partitioning circuit components between structures within the integrated circuit and discrete components enhances design flexibility and minimize power consumption without compromising performance. Therefore, the driver circuit 2700 and matched network 2714 together efficiently convert the input pulse 2704 to an energy wave 2724 of the required frequency, phase, and duration, which is specific to operation of transducer 2710.

The output of the driver amplifier 2716 is coupled with the impedance matching network 2714, such as, but not limited to, a pi network. This pi network can include a discrete inductor or inductors and a discrete capacitor or capacitors to translate the digital output pulse into the required wave shape efficiently and compactly. In one arrangement, the phase and time delay through the pi network are constant. The pi network may also include resistance as well as the discrete inductance and capacitance components. The resistance element is included in the analysis and comprises parasitic resistances within the integrated components and interconnects of the circuit. They are included in the analysis and design of the pi network to assure matching the electrical drive requirements of the energy emitting device.

The impedance matching network 2714 generates a waveform 2722 that is optimized for emitting resonator or transducer 2710. The network 2714 drives the energy emitting resonators or transducers 2710 efficiently thereby reducing power consumption. In particular, the power consumption is substantially less than using an equivalent Digital to Analog Converter (DAC) based design. The integration of miniature, surface mountable, inductors and capacitors enables highly compact driver circuit and minimizes the total number of electronic components. In a hybrid approach, off-chip and return to on-chip, may have size penalty but can be integrated to save power and reduce design complexity.

Figure 28:
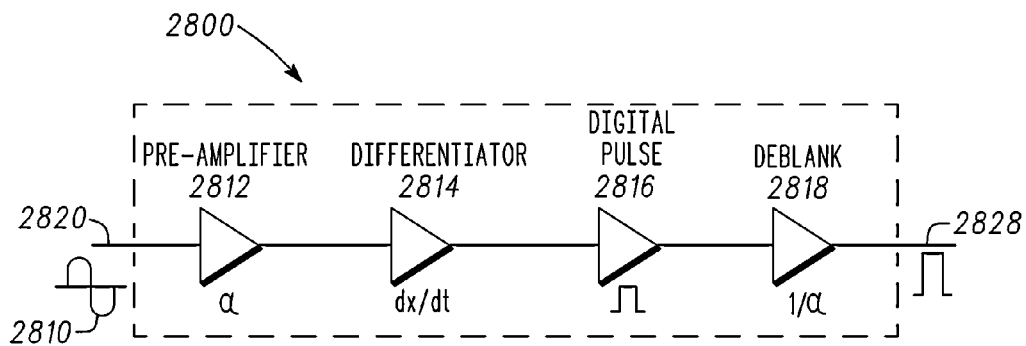
FIG. 28 illustrates a block diagram of an edge-detect receiver circuit in accordance with an exemplary embodiment.

FIG. 28 illustrates a block diagram of an edge-detect receiver circuit 2800 in accordance with an exemplary embodiment. In a first embodiment, edge-detect receiver 2800 is provided to detect wave fronts of energy waves. This enables capturing of parameters including, but not limited to, transit time, phase, or frequency of the energy waves. Circuitry of the integrated edge-detect receiver 2800 provides rapid on-set detection and quickly responds to the arrival of an energy wave. It reliably triggers thereafter a digital output pulse at a same point on the initial wave front of each captured energy wave or pulsed energy wave. The digital pulse can be optimally configured to output with minimal and constant delay. The edge-detect receiver 2800 can isolate and precisely detect the specified point on the initial energy wave or the wave front in the presence of interference and distortion signals thereby overcoming problems commonly associated with detecting one of multiply generated complex signals in energy propagating mediums. The edge-detect receiver 2800 performs these functions accurately over a wide range of amplitudes including very low level energy pulses.

In a second embodiment, the edge-detect receiver 2800 is incorporated within a propagation tuned oscillator (PTO) to maintain positive closed-loop feedback when operating in a continuous wave, pulse or pulse-echo mode. The edge-detect receiver 2800 can be integrated with other circuitry of the PTO by multiplexing input and output circuitry to achieve ultra low-power and small compact size. Integration of the circuitry of the PTO with the edge-detect receiver provides the benefit of increasing sensitivity to low-level signals.

The block diagram illustrates one embodiment of a low power edge-detect receiver circuit 2800 with superior performance at low signal levels. The edge-detect receiver 2800 comprises a preamplifier 2812, a differentiator 2814, a digital pulse circuit 2816 and a deblank circuit 2818. The edge-detect receiver circuit 2800 can be implemented in discrete analog components, digital components or combination thereof. In one embodiment, edge-detect receiver 2800 is integrated into an ASIC as part of a sensor system described hereinbelow. The edge-detect receiver circuit 2800 practices measurement methods that detect energy pulses or pulsed energy waves at specified locations and under specified conditions to enable capturing parameters including, but not limited to, transit time, phase, frequency, or amplitude of energy pulses. A brief description of the method of operation is as follows. In a non-limiting example, a pre-amplifier triggers a comparator circuit responsive to small changes in the slope of an input signal. The comparator and other edge-detect circuitry responds rapidly with minimum delay. Detection of small changes in the input signal assures rapid detection of the arrival of a pulse of energy waves. The minimum phase design reduces extraneous delay thereby introducing less variation into the measurement of the transit time, phase, frequency, or amplitude of the incoming energy pulses.

An input 2820 of edge-detect receiver 2800 is coupled to pre-amplifier 2812. As an example, the incoming wave 2810 to the edge-detect receiver circuit 2800 can be received from an electrical connection, antenna, or transducer. The incoming wave 2810 is amplified by pre-amplifier 2812, which assures adequate sensitivity to small signals. Differentiator circuitry 2814 monitors the output of pre-amplifier 2812 and triggers digital pulse circuitry 2816 whenever a signal change corresponding to an energy wave is detected. For example, a signal change that identifies the energy wave is the initial wave front or the leading edge of the energy wave. In one arrangement, differentiator 2814 detects current flow, and more specifically changes in the slope of the energy wave 2810 by detecting small changes in current flow instead of measuring changes in voltage level to achieve rapid detection of slope. Alternatively, differentiator 2814 can be implemented to trigger on changes in voltage. Together, preamplifier 2812 and differentiator 2814 monitor the quiescent input currents for the arrival of wave front of energy wave(s) 2810. Preamplifier 2812 and differentiator 2814 detect the arrival of low level energy waves as well as large magnitude energy waves. This detection methodology achieves superior performance for very low level signals. Differentiator circuitry 2814 triggers digital pulse circuitry 2816 whenever current flow driven by the initial signal ramp of the incoming wave 2810 is detected. The digital pulse is coupled to deblank circuit 2818 that desensitizes pre-amplifier 2812. For example, the desensitization of pre-amplifier 2812 can comprise a reduction in gain, decoupling of input 2820 from energy wave 2810, or changing the frequency response. The deblank circuit 2818 also disregards voltage or current levels for a specified or predetermined duration of time to effectively skip over the interference sections or distorted portions of the energy wave 2810. In general, energy wave 2810 can comprise more than one change in slope and is typically a damped wave form if the energy wave is pulsed. Additional signals or waves of the pulsed energy wave on the input 2820 of pre-amplifier 2812 are not processed during the preset blanking period. In this example, the digital output pulse 2828 can then be coupled to signal processing circuitry as explained hereinbelow. In one embodiment, the electronic components are operatively coupled as blocks within an integrated circuit. As will be shown ahead, this integration arrangement performs its specific functions efficiently with a minimum number of components. This is because the circuit components are partitioned between structures within an integrated circuit and discrete components, as well as innovative partitioning of analog and digital functions, to achieve the required performance with a minimum number of components and minimum power consumption.

Figure 29:
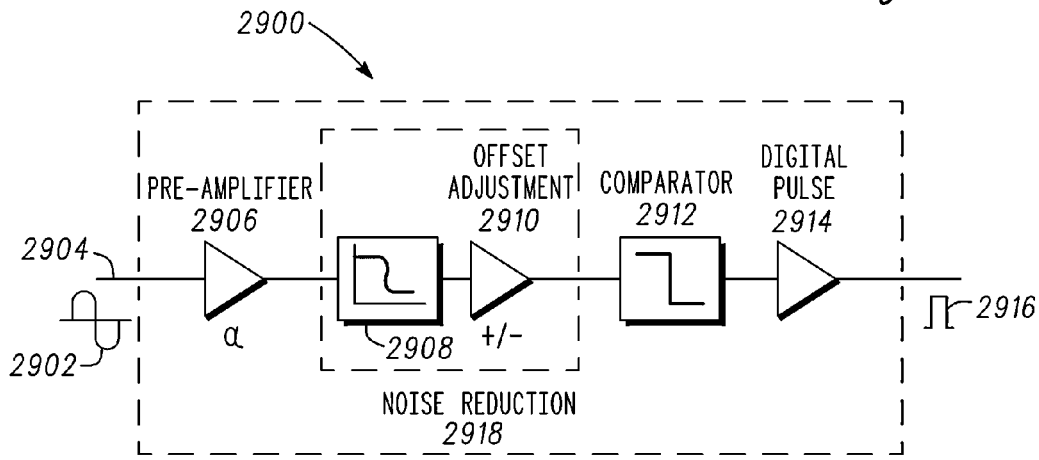
FIG. 29 is a block diagram of a zero-crossing receiver in accordance with one embodiment.

FIG. 29 is a block diagram of a zero-crossing receiver 2900 in accordance with one embodiment. In a first embodiment, the zero-crossing receiver 2900 is provided to detect transition states of energy waves, such as the transition of each energy wave through a mid-point of a symmetrical or cyclical waveform. This enables capturing of parameters including, but not limited to, transit time, phase, or frequency of the energy waves. The receiver rapidly responds to a signal transition and outputs a digital pulse that is consistent with the energy wave transition characteristics and with minimal delay. The zero-crossing receiver 2900 further discriminates between noise and the energy waves of interest, including very low level waves by way of adjustable levels of noise reduction. A noise reduction section 2918 comprises a filtering stage and an offset adjustment stage to perform noise suppression accurately over a wide range of amplitudes including low level waves.

In a second embodiment, a zero-crossing receiver 2900 is provided to convert an incoming symmetrical, cyclical, or sine wave to a square or rectangular digital pulse sequence with superior performance for very low level input signals. The digital pulse sequence represents pulse timing intervals that are consistent with the energy wave transition times. The zero-crossing receiver 2900 is coupled with a sensing assembly to generate the digital pulse sequence responsive to evaluating transitions of the incoming sine wave. This digital pulse sequence conveys timing information related to parameters of interest, such as applied forces, associated with the physical changes in the sensing assembly.

In a third embodiment, the integrated zero-crossing receiver is incorporated within a propagation tuned oscillator (PTO) to maintain positive closed-loop feedback when operating in a continuous wave mode, pulse mode, or pulse-echo mode. The integrated edge zero-crossing receiver is electrically integrated with the PTO by multiplexing input and output circuitry to achieve ultra low-power and small compact size. Electrical components of the PTO are integrated with components of the zero-crossing receiver to assure adequate sensitivity to low-level signals.

In one embodiment, low power zero-crossing receiver 2900 can be integrated with other circuitry of the propagation tuned oscillator to further improve performance at low signal levels. The zero-crossing receiver 2900 comprises a preamplifier 2906, a filter 2908, an offset adjustment circuitry 2910, a comparator 2912, and a digital pulse circuit 2914. The filter 2908 and offset adjustment circuitry 2910 constitute a noise reduction section 2918 as will be explained ahead. The zero-crossing receiver 2900 can be implemented in discrete analog components, digital components or combination thereof. The integrated zero-crossing receiver 2900 practices measurement methods that detect the midpoint of energy waves at specified locations, and under specified conditions, to enable capturing parameters including, but not limited to, transit time, phase, or frequency of energy waves. A brief description of the method of operation is as follows.

An incoming energy wave 2902 is coupled from an electrical connection, antenna, or transducer to an input 2904 of zero-crossing receiver 2900. Input 2904 of zero-crossing receiver 2900 is coupled to pre-amplifier 2906 to amplify the incoming energy wave 2902. The amplified signal is filtered by filter 2908. Filter 2908 is coupled to an output of pre-amplifier 2906 and an input of offset adjustment circuitry 2910. In one configuration, filter 2908 is a low-pass filter to remove high frequency components above the incoming energy wave 2902 bandwidth. In another arrangement, the filter is a band-pass filter with a pass-band corresponding to the bandwidth of the incoming energy wave 2902. It is not however limited to either arrangement. The offset of the filtered amplified wave is adjusted by offset adjustment circuitry 2910. An input of comparator 2912 is coupled to an output of offset adjustment circuitry 2910. Comparator 2912 monitors the amplified waveforms and triggers digital pulse circuitry 2914 whenever the preset trigger level is detected. Digital pulse circuit 2914 has an input coupled to the output of comparator 2912 and an output for providing digital pulse 2916. The digital pulse 2916 can be further coupled to signal processing circuitry, as will be explained ahead.

In a preferred embodiment, the electronic components are operatively coupled together as blocks of integrated circuits. As will be shown ahead, this integrated arrangement performs its specific functions efficiently with a minimum number of components. This is because the circuit components are partitioned between structures within an integrated circuit and discrete components, as well as innovative partitioning of analog and digital functions, to achieve the required performance with a minimum number of components and minimum power consumption.

Figure 30:
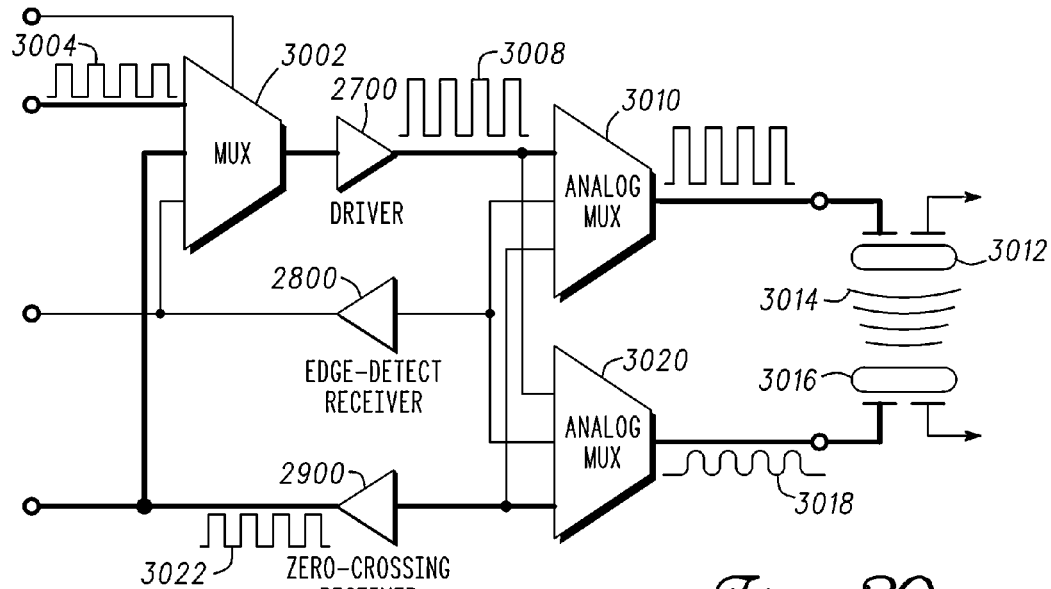
FIG. 30 is a sensor interface diagram incorporating the zero-crossing receiver in a continuous wave multiplexing arrangement for maintaining positive closed-loop feedback in accordance with one embodiment.

FIG. 30 is a sensor interface diagram incorporating the zero-crossing receiver 2900 in a continuous wave multiplexing arrangement for maintaining positive closed-loop feedback in accordance with one embodiment. The positive closed-loop feedback is illustrated by the bold line path. Initially, multiplexer (mux) 3002 receives as input a clock signal 3004, which is passed to the transducer driver 2700 to produce the drive line signal 3008. Analog multiplexer (mux) 3010 receives drive line signal 3008, which is passed to the transmitter transducer 3012 to generate energy waves 3014. Transducer 3012 is located at a first location of an energy propagating medium. The emitted energy waves 3014 propagate through the energy propagating medium. Receiver transducer 3016 is located at a second location of the energy propagating medium. Receiver transducer 3016 captures the energy waves 3014, which are fed to analog mux 3020 and passed to the zero-crossing receiver 2900. The captured energy waves by transducer 3016 are indicated by electrical waves 3018 provided to mux 3020. Zero-crossing receiver 2900 outputs a pulse corresponding to each zero crossing detected from captured electrical waves 3018. Alternatively, edge-detect receiver 2800 can be used to detect propagated energy waves. The zero crossings are counted and used to determine changes in the phase and frequency of the energy waves propagating through the energy propagating medium. In a non-limiting example, a parameter such as applied force is measured by relating the measured phase and frequency to a known relationship between the parameter (e.g. force) and the material properties of the energy propagating medium. In general, pulse sequence 3022 corresponds to the detected signal frequency. The zero-crossing receiver 2900 is in a feedback path of the propagation tuned oscillator. The pulse sequence 3022 is coupled through mux 3002 in a positive closed-loop feedback path. The pulse sequence 3022 disables the clock signal 3004 such that the path providing pulse sequence 3022 is coupled to driver 2700 to continue emission of energy waves into the energy propagating medium and the path of clock signal 3004 to driver 2700 is disabled. The pulse sequence can comprise one or more pulses. Thus, closing the loop continues a process of energy wave emission, energy wave propagation, and detection of the energy wave in the energy propagation medium with the detection generating a new signal to initiate a next emission.

Figure 31:
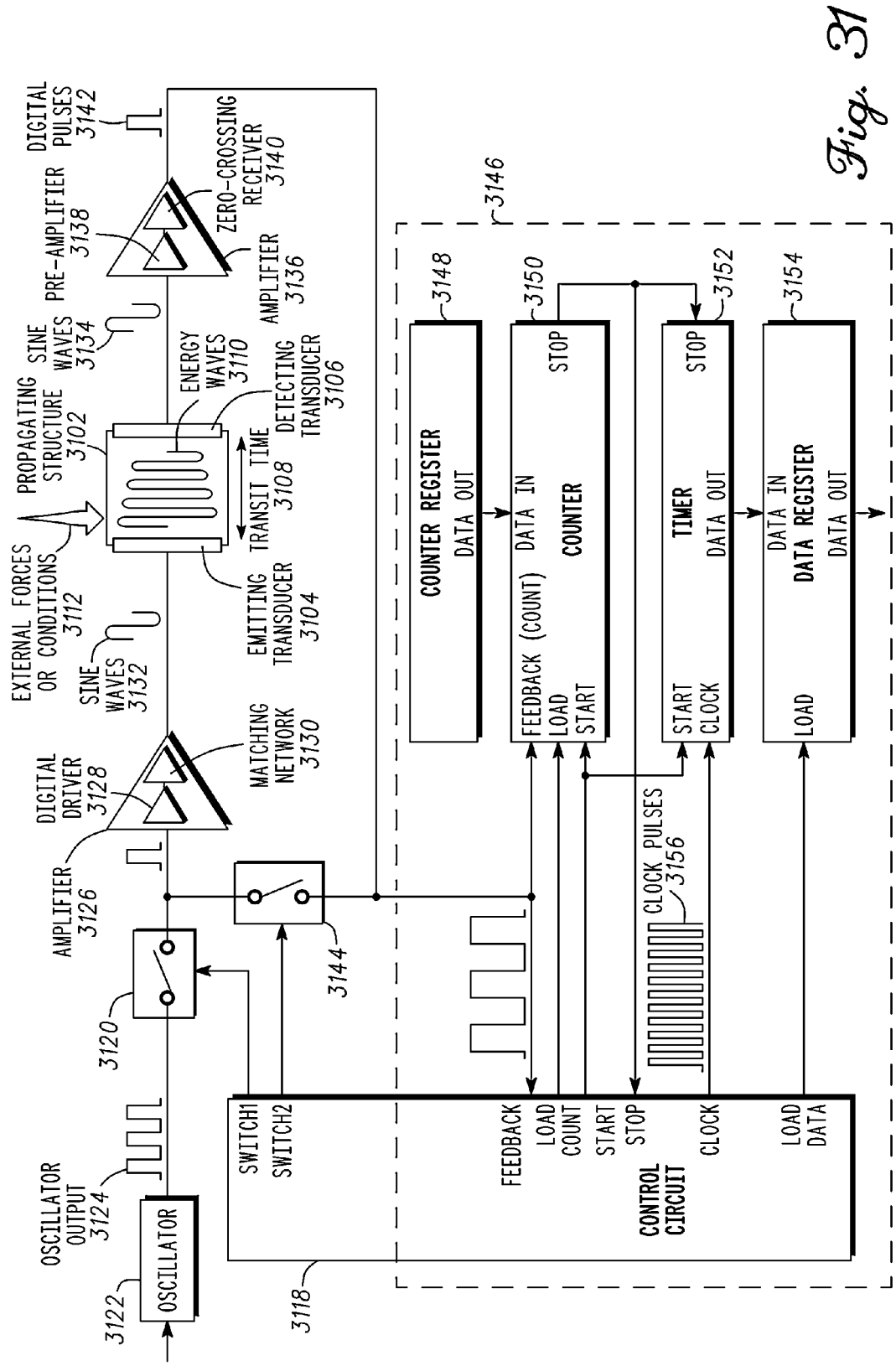
FIG. 31 is an exemplary block diagram of a propagation tuned oscillator (PTO) incorporating the zero-crossing receiver for operation in continuous wave mode.

FIG. 31 is an exemplary block diagram of a propagation tuned oscillator (PTO) incorporating the zero-crossing receiver 3140 for operation in continuous wave mode. In particular, it illustrates closed loop measurement of the transit time of ultrasound waves within a waveguide by the operation of the propagation tuned oscillator as disclosed hereinabove. Alternatively, an edge-detect receiver can be used for energy wave detection. This example is for operation in continuous wave mode. The system can also be operated in pulse mode and a pulse-echo mode. Pulse mode and pulsed echo-mode use a pulsed energy wave. Pulse-echo mode uses reflection to direct an energy wave within the energy propagation medium. Briefly, the digital logic circuit 3146 digitizes the frequency of operation of the propagation tuned oscillator.

In continuous wave mode of operation a sensor comprising transducer 3104, propagating structure 3102, and transducer 3106 is used to measure the parameter. In general, the parameter to be measured affects the properties of the propagating medium. For example, an external force or condition 3112 is applied to propagating structure 3102 that changes the length of the waveguide in a path of a propagating energy wave. A change in length corresponds to a change in transit time 3108 of the propagating wave. Similarly, the length of propagating structure 3102 corresponds to the applied force 3112. A length reduction corresponds to a higher force being applied to the propagating structure 3102. Conversely, a length increase corresponds to a lowering of the applied force 3112 to the propagating structure 3102. The length of propagating structure 3102 is measured and is converted to force by way of a known length to force relationship.

Transducer 3104 is an emitting device in continuous wave mode. The sensor for measuring a parameter comprises transducer 3104 coupled to propagating structure 3102 at a first location. A transducer 3106 is coupled to propagating structure 3102 at a second location. Transducer 3106 is a receiving transducer for capturing propagating energy waves. In one embodiment, the captured propagated energy waves are electrical sine waves 3134 that are output by transducer 3106.

A measurement sequence is initiated when control circuitry 3118 closes switch 3120 coupling oscillator output 3124 of oscillator 3122 to the input of amplifier 3126. One or more pulses provided to amplifier 3126 initiates an action to propagate energy waves 3110 having simple or complex waveforms through energy propagating structure or medium 3102. Amplifier 3126 comprises a digital driver 3128 and matching network 3130. In one embodiment, amplifier 3126 transforms the oscillator output of oscillator 3122 into sine waves of electrical waves 3132 having the same repetition rate as oscillator output 3124 and sufficient amplitude to excite transducer 3104.

Emitting transducer 3104 converts the sine waves 3132 into energy waves 3110 of the same frequency and emits them at the first location into energy propagating structure or medium 3102. The energy waves 3110 propagate through energy propagating structure or medium 3102. Upon reaching transducer 3106 at the second location, energy waves 3110 are captured, sensed, or detected. The captured energy waves are converted by transducer 3106 into sine waves 3134 that are electrical waves having the same frequency.

Amplifier 3136 comprises a pre-amplifier 3138 and zero-cross receiver 3140. Amplifier 3136 converts the sine waves 3134 into digital pulses 3142 of sufficient duration to sustain the behavior of the closed loop circuit. Control circuitry 3118 responds to digital pulses 3142 from amplifier 3136 by opening switch 3120 and closing switch 3144. Opening switch 3120 decouples oscillator output 3124 from the input of amplifier 3126. Closing switch 3144 creates a closed loop circuit coupling the output of amplifier 3136 to the input of amplifier 3126 and sustaining the emission, propagation, and detection of energy waves through energy propagating structure or medium 3102.

An equilibrium state is attained by maintaining unity gain around this closed loop circuit wherein sine waves 3132 input into transducer 3104 and sine waves 3134 output by transducer 3106 are in phase with a small but constant offset. Transducer 3106 as disclosed above, outputs the sine waves 3134 upon detecting energy waves propagating to the second location. In the equilibrium state, an integer number of energy waves 3110 propagate through energy propagating structure or medium 3102.

Movement or changes in the physical properties of energy propagating structure or medium 3102 change a transit time 3108 of energy waves 3110. The transit time 3108 comprises the time for an energy wave to propagate from the first location to the second location of propagating structure 3102. Thus, the change in the physical property of propagating structure 3102 results in a corresponding time period change of the energy waves 3110 within energy propagating structure or medium 3102. These changes in the time period of the energy waves 3110 alter the equilibrium point of the closed loop circuit and frequency of operation of the closed loop circuit. The closed loop circuit adjusts such that sine waves 3132 and 3134 correspond to the new equilibrium point. The frequency of energy waves 3110 and changes to the frequency correlate to changes in the physical attributes of energy propagating structure or medium 3102.

The physical changes may be imposed on energy propagating structure 3102 by external forces or conditions 3112 thus translating the levels and changes of the parameter or parameters of interest into signals that may be digitized for subsequent processing, storage, and display. Translation of the operating frequency into digital binary numbers facilitates communication, additional processing, storage, and display of information about the level and changes in physical parameters of interest. Similarly, the frequency of energy waves 3110 during the operation of the closed loop circuit, and changes in this frequency, may be used to measure movement or changes in physical attributes of energy propagating structure or medium 3102.

Prior to measurement of the frequency or operation of the propagation tuned oscillator, control logic 3118 loads the loop count into digital counter 3150 that is stored in count register 3148. The first digital pulses 3142 initiates closed loop operation within the propagation tuned oscillator and signals control circuit 3118 to start measurement operations. At the start of closed loop operation, control logic 3118 enables digital counter 3150 and digital timer 3152. In one embodiment, digital counter 3150 decrements its value on the rising edge of each digital pulse output by zero-crossing receiver 3140. Digital timer 3152 increments its value on each rising edge of clock pulses 3156. When the number of digital pulses 3142 has decremented, the value within digital counter 3150 to zero a stop signal is output from digital counter 3150. The stop signal disables digital timer 3152 and triggers control circuit 3118 to output a load command to data register 3154. Data register 3154 loads a binary number from digital timer 3152 that is equal to the period of the energy waves or pulses times the value in counter 3148 divided by clock period 3156. With a constant clock period 3156, the value in data register 3154 is directly proportional to the aggregate period of the energy waves or pulses accumulated during the measurement operation. Duration of the measurement operation and the resolution of measurements may be adjusted by increasing or decreasing the value preset in the count register 3148.

Figure 32:
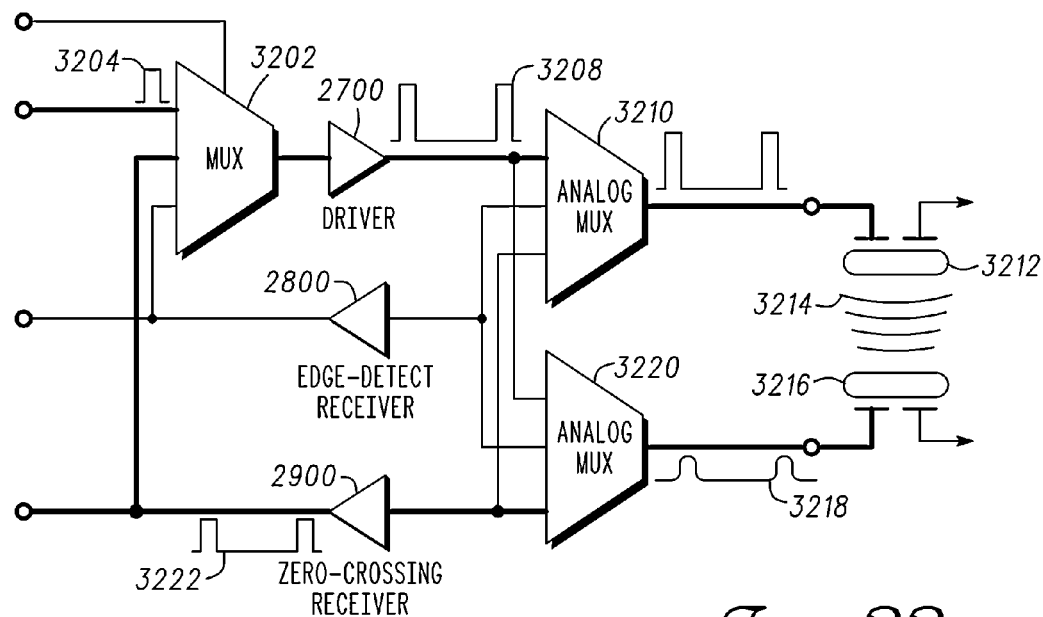
FIG. 32 is a sensor interface diagram incorporating the integrated zero-crossing receiver in a pulse multiplexing arrangement for maintaining positive closed-loop feedback in accordance with one embodiment.

FIG. 32 is a sensor interface diagram incorporating the integrated zero-crossing receiver 2900 in a pulse multiplexing arrangement for maintaining positive closed-loop feedback in accordance with one embodiment. In one embodiment, the circuitry other than the sensor is integrated on an application specific integrated circuit (ASIC). The positive closed-loop feedback path of the circuit is illustrated by the bold line path. Initially, mux 3202 is enabled to couple one or more digital pulses 3204 to the transducer driver 2700. Transducer driver 2700 generates a pulse sequence 3208 corresponding to digital pulses 3204. Analog mux 3210 is enabled to couple pulse sequence 3208 to the transmitter transducer 3212. Transducer 3212 is coupled to a medium at a first location. Transducer 3212 responds to pulse sequence 3208 and generates corresponding energy pulses 3214 that are emitted into the medium at the first location. The energy pulses 3214 propagate through the medium.

A receiver transducer 3216 is located at a second location on the medium. Receiver transducer 3216 captures the energy pulses 3214 and generates a corresponding signal of electrical pulses 3218. Transducer 3216 is coupled to a mux 3220. Mux 3220 is enabled to couple to zero-cross receiver 2900. Electrical pulses 3218 from transducer 3216 are coupled to zero-cross receiver 2900. Zero-cross receiver 2900 counts zero crossings of electrical pulses 3218 to determine changes in phase and frequency of the energy pulses responsive to an applied force, as previously explained. Alternatively edge-detect receiver 2800 could be used to detect propagated energy waves. Zero-cross receiver 2900 outputs a pulse sequence 3222 corresponding to the detected signal frequency. Pulse sequence 3222 is coupled to mux 3202. Mux 3202 is decoupled from coupling digital pulses 3204 to driver 2700 upon detection of pulses 3222. Simultaneously, mux 3202 is enabled to couple pulses 3222 to driver 2700 upon detection of pulses 3222 thereby creating a positive closed-loop feedback path. Thus, in pulse mode, zero-cross receiver 2900 is part of the closed-loop feedback path that continues emission of energy pulses into the medium at the first location and detection at the second location to measure a transit time and changes in transit time of pulses through the medium.

Figure 33:
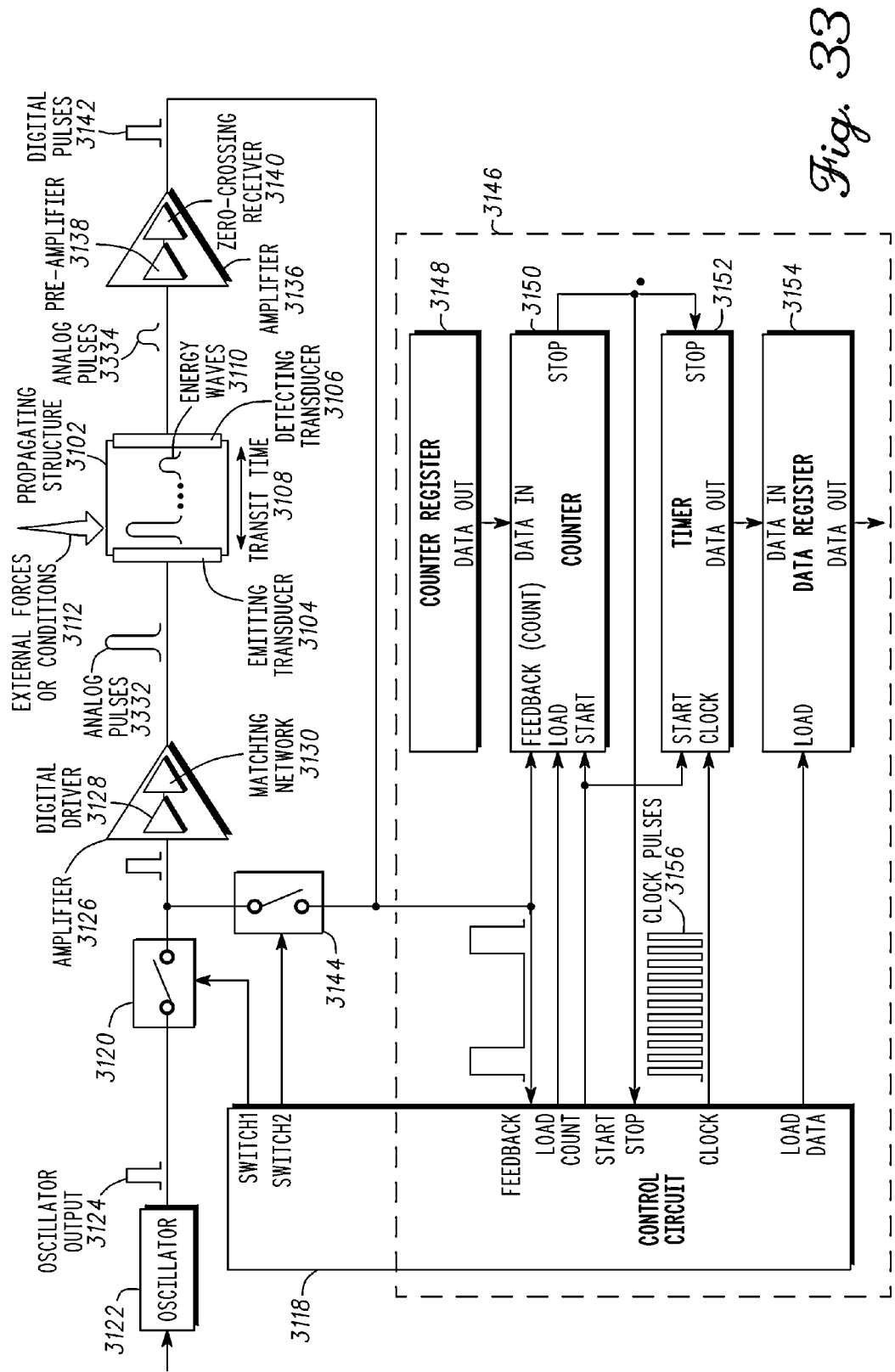
FIG. 33 is an exemplary block diagram of a propagation tuned oscillator (PTO) incorporating the zero-crossing receiver for operation in pulse mode in accordance with one embodiment.

FIG. 33 is an exemplary block diagram of a propagation tuned oscillator (PTO) incorporating the zero-crossing receiver 3140 for operation in pulse mode. In particular, it illustrates closed loop measurement of the transit time of ultrasound waves within a waveguide by the operation of a propagation tuned oscillator as disclosed above. This example is for operation in pulse mode. The system can also be operated in continuous wave mode, pulse mode, and pulse-echo mode. Continuous wave mode uses a continuous wave signal. Pulse-echo mode uses reflection to direct an energy wave within the energy propagation medium. Briefly, the digital logic circuit 3146 digitizes the frequency of operation of the propagation tuned oscillator.

In pulse mode of operation, a sensor comprising transducer 3104, propagating structure 3102, and transducer 3106 is used to measure the parameter. In general, the parameter to be measured affects the properties of the propagating medium. For example, an external force or condition 3112 is applied to propagating structure 3102 that changes the length of the waveguide in a path of a propagating energy wave. A change in length corresponds to a change in transit time 3108 of the propagating wave. The length of propagating structure 3102 is measured and is converted to a force measurement by way of a known length to force relationship. One benefit of pulse mode operation is the use of a high magnitude pulsed energy wave. In one embodiment, the magnitude of the energy wave decays as it propagates through the medium. The use of a high magnitude pulse is a power efficient method to produce a detectable signal if the energy wave has to traverse a substantial distance or is subject to a reduction in magnitude as it propagated due to the medium.

A measurement sequence is initiated when control circuitry 3118 closes switch 3120 coupling oscillator output 3124 of oscillator 3122 to the input of amplifier 3126. One or more pulses provided to amplifier 3126 initiates an action to propagate energy waves 3110 having simple or complex waveforms through energy propagating structure or medium 3102. Amplifier 3126 comprises a digital driver 3128 and matching network 3130. In one embodiment, amplifier 3126 transforms the oscillator output of oscillator 3122 into analog pulses of electrical waves 3332 having the same repetition rate as oscillator output 3124 and sufficient amplitude to excite transducer 3104.

Emitting transducer 3104 converts the analog pulses 3332 into energy waves 3110 of the same frequency and emits them at a first location into energy propagating structure or medium 3102. The energy waves 3110 propagate through energy propagating structure or medium 3102. Upon reaching transducer 3106 at the second location, energy waves 3110 are captured, sensed, or detected. The captured energy waves are converted by transducer 3106 into analog pulses 3334 that are electrical waves having the same frequency as energy waves 3110.

Amplifier 3136 comprises a pre-amplifier 3138 and zero-cross receiver 3140. Amplifier 3136 converts the analog pulses 3334 into digital pulses 3142 of sufficient duration to sustain the behavior of the closed loop circuit. Alternatively, detection can be achieved using an edge detect receiver. Control circuitry 3118 responds to digital pulses 3142 from amplifier 3136 by opening switch 3120 and closing switch 3144. Opening switch 3120 decouples oscillator output 3124 from the input of amplifier 3126. Closing switch 3144 creates a closed loop circuit coupling the output of amplifier 3136 to the input of amplifier 3126 and sustaining the emission, propagation, and detection of energy waves through energy propagating structure or medium 3102.

An equilibrium state is attained by maintaining unity gain around this closed loop circuit wherein pulses 3332 input into transducer 3104 and pulses 3334 output by transducer 3106 are in phase with a small but constant offset. Transducer 3106 as disclosed above, outputs the pulses 3334 upon detecting energy waves propagating to the second location. In the equilibrium state, an integer number of energy waves 3110 propagate through energy propagating structure or medium 3102.

Movement or changes in the physical properties of energy propagating structure or medium 3102 change a transit time 3108 of energy waves 3110. The transit time 3108 comprises the time for an energy wave to propagate from the first location to the second location of propagating structure 3102. Thus, the change in the physical property of propagating structure 3102 results in a corresponding time period change of the energy waves 3110 within energy propagating structure or medium 3102. These changes in the time period of the energy waves 3110 alter the equilibrium point of the closed loop circuit and frequency of operation of the closed loop circuit. The closed loop circuit adjusts such that pulses 3332 and 3334 correspond to the new equilibrium point. The frequency of energy waves 3110 and changes to the frequency correlate to changes in the physical attributes of energy propagating structure or medium 3102.

The physical changes may be imposed on energy propagating structure 3102 by external forces or conditions 3112 thus translating the levels and changes of the parameter or parameters of interest into signals that may be digitized for subsequent processing, storage, and display. Translation of the operating frequency into digital binary numbers facilitates communication, additional processing, storage, and display of information about the level and changes in physical parameters of interest as disclosed in more detail hereinabove. Similarly, the frequency of energy waves 3110 during the operation of the closed loop circuit, and changes in this frequency, may be used to measure movement or changes in physical attributes of energy propagating structure or medium 3102.

Figure 34:
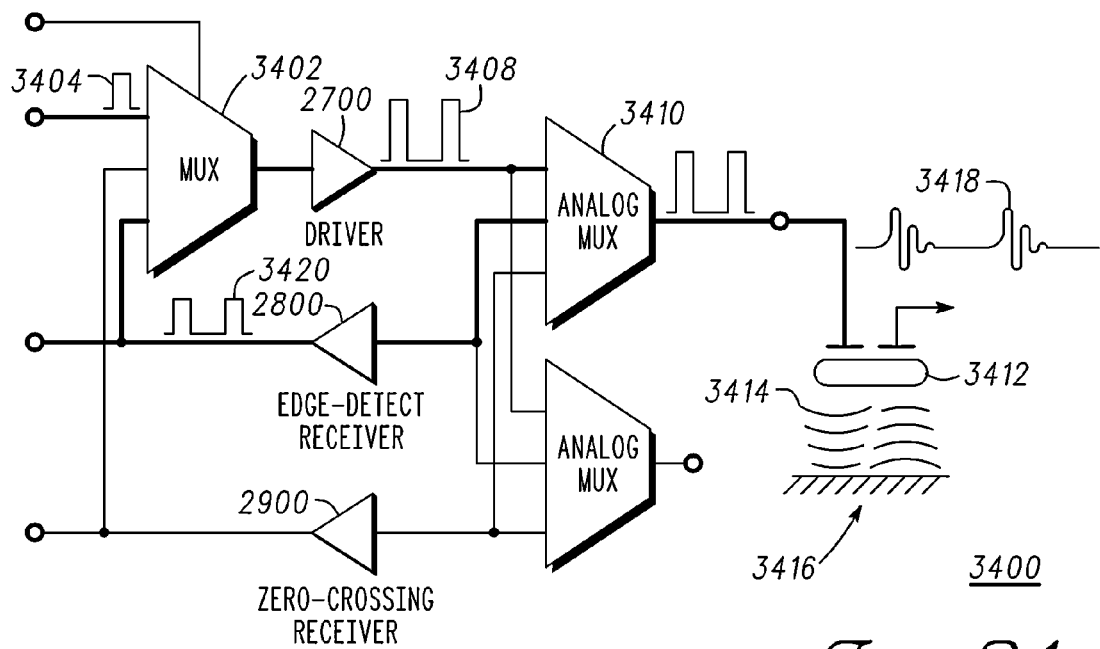
FIG. 34 is a sensor interface diagram incorporating the edge-detect receiver circuit in a pulse-echo multiplexing arrangement for maintaining positive closed-loop feedback in accordance with one embodiment.

FIG. 34 is a sensor interface diagram incorporating the edge-detect receiver circuit 2800 in a pulse-echo multiplexing arrangement for maintaining positive closed-loop feedback in accordance with one embodiment. The positive closed-loop feedback of the circuit is illustrated by the bold line path. Initially, multiplexer (mux) 3402 receives as input a digital pulse 3404, which is passed to the transducer driver 2700 to produce the pulse sequence 3408. Analog multiplexer (mux) 3410 receives pulse sequence 3408, which is passed to the transducer 3412 to generate energy pulses 3414. Energy pulses 3414 are emitted into a first location of a medium. Energy pulses 3414 propagate through the medium towards a second location having a reflective surface 3416. In the pulse-echo example, energy pulses 3414 are reflected off surface 3416 at the second location of the medium, for example, the end of a waveguide or reflector, and echoed back to the transducer 3412.

The transducer 3412 proceeds to capture the reflected pulse echo. In pulsed echo mode, the transducer 3412 performs as both a transmitter and a receiver. As disclosed above, transducer 3412 toggles back and forth between emitting and receiving energy waves. Transducer 3412 captures the reflected echo pulses, which are coupled to analog mux 3410 and directed to the edge-detect receiver 2800. The captured reflected echo pulses are indicated by electrical waves 3418. Edge-detect receiver 2800 locks on to a leading edge of signal 3418 corresponding to the wave front of a propagated energy wave to determine changes in phase and frequency of the energy pulses 3414 responsive to an applied force, as previously explained. In the embodiment, the energy wave is a reflected pulsed energy wave. Alternatively, zero-crossing receiver 2900 can be used to detect the captured reflected echo pulses.

Among other parameters, edge-detect receiver 2800 generates a pulse sequence 3420 corresponding to the detected signal frequency. The pulse sequence 3420 is coupled to mux 3402 and directed to driver 2700 to initiate one or more energy waves being emitted into the medium by transducer 3412. Pulse 3404 is decoupled from being provided to driver 2700. Thus, a positive closed loop feedback is formed that repeatably emits energy waves into the medium until mux 3402 prevents a signal from being provided to driver 2700.

Figure 35:
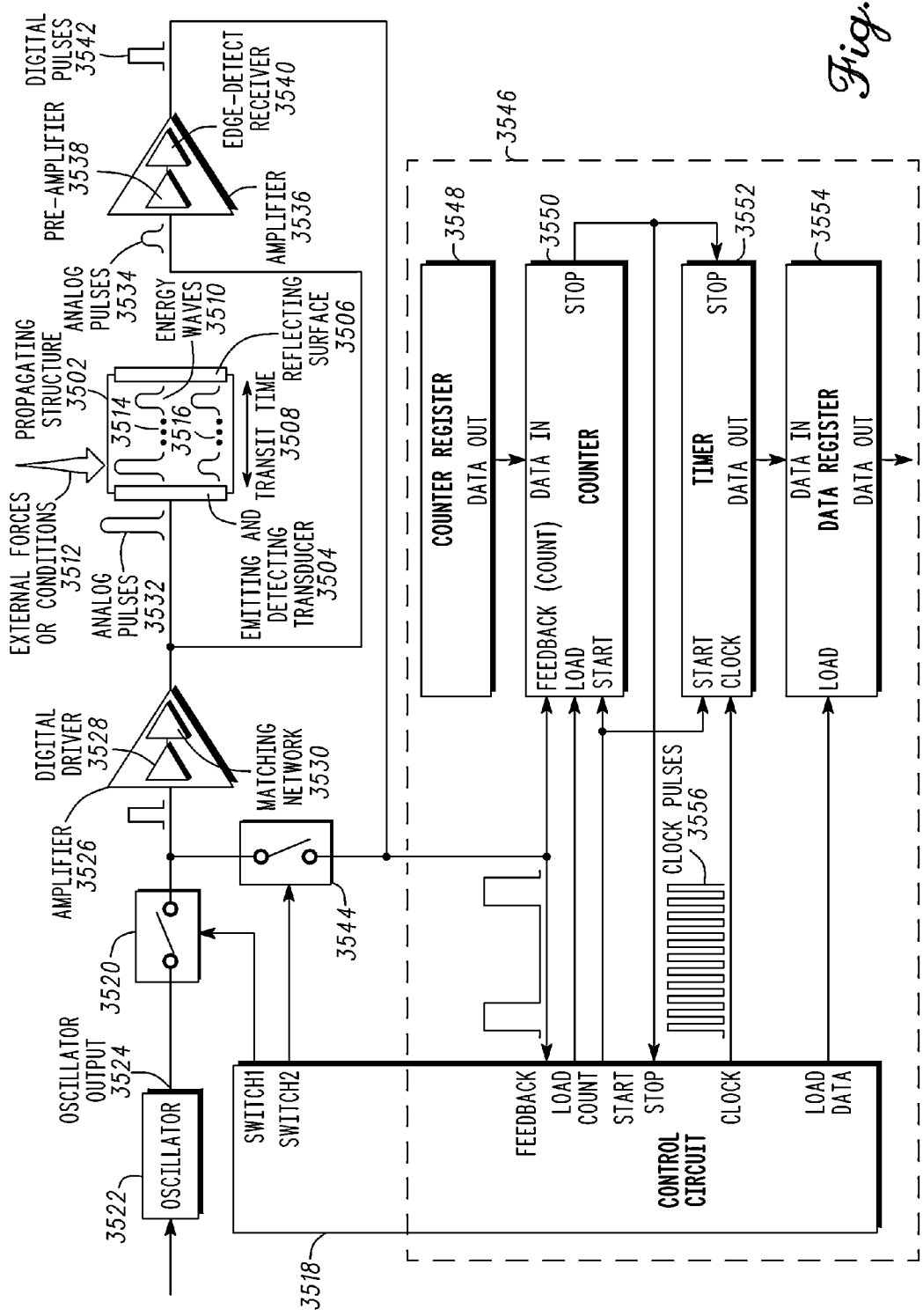
FIG. 35 is an exemplary block diagram of a propagation tuned oscillator (PTO) incorporating the edge-detect receiver circuit for operation in pulse echo mode in accordance with one embodiment.

FIG. 35 is an exemplary block diagram of a propagation tuned oscillator (PTO) incorporating the edge-detect receiver circuit 3440 for operation in pulse echo mode. In particular, it illustrates closed loop measurement of a transit time of reflected ultrasound waves propagating within the waveguide by the operation of a propagation tuned oscillator as disclosed above. This example is for operation in a pulse echo mode. The system can also be operated in pulse mode and a continuous wave mode. Pulse mode does not use a reflected signal. Continuous wave mode uses a continuous signal. Briefly, the digital logic circuit 3446 digitizes the frequency of operation of the propagation tuned oscillator.

In pulse-echo mode of operation a sensor comprising transducer 3404, propagating structure 3402, and reflecting surface 3406 is used to measure the parameter. In general, the parameter to be measured affects the properties of the propagating medium. For example, an external force or condition 3412 is applied to propagating structure 3402 that changes the length of the waveguide in a path of a propagating energy wave. A change in length corresponds to a change in transit time of the propagating wave. Similarly, the length of propagating structure 3402 corresponds to the applied force 3412. A length reduction corresponds to a higher force being applied to the propagating structure 3402. Conversely, a length increase corresponds to a lowering of the applied force 3412 to the propagating structure 3402. The length of propagating structure 3402 is measured and is converted to force by way of a known length to force relationship.

Transducer 3404 is both an emitting device and a receiving device in pulse-echo mode. The sensor for measuring a parameter comprises transducer 3404 coupled to propagating structure 3402 at a first location. A reflecting surface is coupled to propagating structure 3402 at a second location. Transducer 3404 has two modes of operation comprising an emitting mode and receiving mode. Transducer 3404 emits an energy wave into the propagating structure 3402 at the first location in the emitting mode. The energy wave propagates to a second location and is reflected by reflecting surface 3406. The reflected energy wave is reflected towards the first location. Transducer 3404 subsequently receives the reflected energy wave and generates a signal in the receiving mode corresponding to the reflected energy wave.

A measurement sequence in pulse echo mode is initiated when control circuitry 3418 closes switch 3420 coupling digital output 3424 of oscillator 3422 to the input of amplifier 3426. One or more pulses provided to amplifier 3426 starts a process to emit one or more energy waves 3410 having simple or complex waveforms into energy propagating structure or medium 3402. Amplifier 3426 comprises a digital driver 3428 and matching network 3430. In one embodiment, amplifier 3426 transforms the digital output of oscillator 3422 into pulses of electrical waves 3432 having the same repetition rate as digital output 3424 and sufficient amplitude to excite transducer 3404.

Transducer 3404 converts the pulses of electrical waves 3432 into pulses of energy waves 3410 of the same repetition rate and emits them into energy propagating structure or medium 3402. The pulses of energy waves 3410 propagate through energy propagating structure or medium 3402 as shown by energy wave propagation 3414 towards reflecting surface 3406. Upon reaching reflecting surface 3406, energy waves 3410 are reflected by reflecting surface 3406. Reflected energy waves propagate towards transducer 3404 as shown by energy wave propagation 3416. The reflected energy waves are detected by transducer 3404 and converted into pulses of electrical waves 3434 having the same repetition rate.

Amplifier 3436 comprises a pre-amplifier 3438 and edge-detect receiver 3440. Amplifier 3436 converts the pulses of electrical waves 3434 into digital pulses 3442 of sufficient duration to sustain the pulse behavior of the closed loop circuit. Control circuitry 3418 responds to digital output pulses 3442 from amplifier 3436 by opening switch 3420 and closing switch 3444. Opening switch 3420 decouples oscillator output 3424 from the input of amplifier 3426. Closing switch 3444 creates a closed loop circuit coupling the output of amplifier 3436 to the input of amplifier 3426 and sustaining the emission, propagation, and detection of energy pulses through energy propagating structure or medium 3402.

An equilibrium state is attained by maintaining unity gain around this closed loop circuit wherein electrical waves 3432 input into transducer 3404 and electrical waves 3434 output by transducer 3404 are in phase with a small but constant offset. Transducer 3404 as disclosed above, outputs the electrical waves 3434 upon detecting reflected energy waves reflected from reflecting surface 3406. In the equilibrium state, an integer number of pulses of energy waves 3410 propagate through energy propagating structure or medium 3402.

Movement or changes in the physical properties of energy propagating structure or medium 3402 change a transit time 3408 of energy waves 3410. The transit time 3408 comprises the time for an energy wave to propagate from the first location to the second location of propagating structure 3402 and the time for the reflected energy wave to propagate from the second location to the first location of propagating structure 3402. Thus, the change in the physical property of propagating structure 3402 results in a corresponding time period change of the energy waves 3410 within energy propagating structure or medium 3402. These changes in the time period of the repetition rate of the energy pulses 3410 alter the equilibrium point of the closed loop circuit and repetition rate of operation of the closed loop circuit. The closed loop circuit adjusts such that electrical waves 3432 and 3434 correspond to the new equilibrium point. The repetition rate of energy waves 3410 and changes to the repetition rate correlate to changes in the physical attributes of energy propagating structure or medium 3402.

The physical changes may be imposed on energy propagating structure 3402 by external forces or conditions 3412 thus translating the levels and changes of the parameter or parameters of interest into signals that may be digitized for subsequent processing, storage, and display. Translation of the operating frequency into digital binary numbers facilitates communication, additional processing, storage, and display of information about the level and changes in physical parameters of interest. Similarly, the frequency of energy waves 3410 during the operation of the closed loop circuit, and changes in this frequency, may be used to measure movement or changes in physical attributes of energy propagating structure or medium 3402.

Prior to measurement of the frequency or operation of the propagation tuned oscillator, control circuitry 3418 loads the loop count into digital counter 3450 that is stored in count register 3448. The first digital pulses 3442 initiates closed loop operation within the propagation tuned oscillator and signals control circuit 3418 to start measurement operations. At the start of closed loop operation, control circuit 3418 enables digital counter 3450 and digital timer 3452. In one embodiment, digital counter 3450 decrements its value on the rising edge of each digital pulse output by edge-detect receiver 3440. Digital timer 3452 increments its value on each rising edge of clock pulses 3456. A stop signal is output from digital counter 3450 when digital pulses 3442 has decremented the value within digital counter 3450 to zero. The stop signal disables digital timer 3452 and triggers control circuit 3418 to output a load command to data register 3454. Data register 3454 loads a binary number from digital timer 3452 that is equal to the period of the energy waves or pulses times the value in counter 3448 divided by clock period 3456. With a constant clock period 3456, the value in data register 3454 is directly proportional to the aggregate period of the energy waves or pulses accumulated during the measurement operation. Duration of the measurement operation and the resolution of measurements may be adjusted by increasing or decreasing the value preset in the count register 3448.

Figure 36:
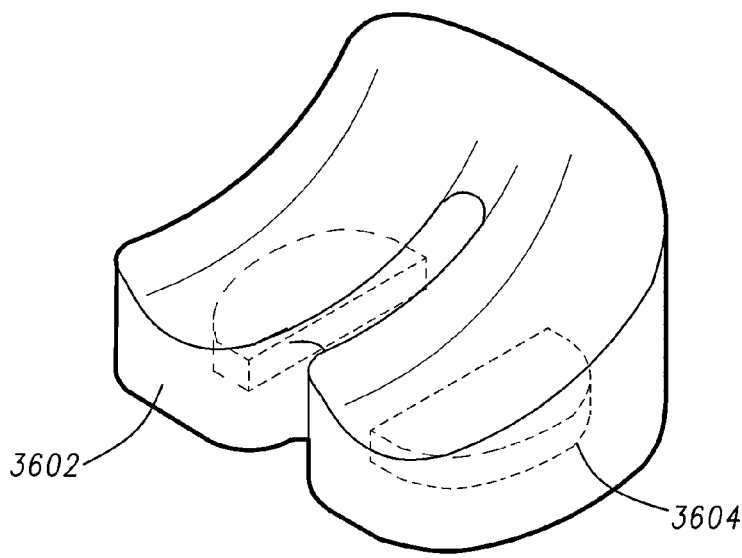
FIG. 36 is a final insert in accordance with an exemplary embodiment.

FIG. 36 is a final insert 3602 in accordance with an exemplary embodiment. In the example, the final insert 3602 is a prosthetic component for a total knee reconstruction. Insert 3602 comprises two bearing surfaces that couple to the condyles of a femur or femoral prosthetic component. A bottom surface of insert 3602 couples to a major surface of the tibial implant. The final insert 3602 is an active device for measuring a parameter of the muscular-skeletal system. A sensing module 3604 as disclosed hereinabove underlies each bearing surface of insert 3602. In one embodiment, a contacting surface of insert 3602 couples to the bearing surface. In one embodiment, insert 3602 has a conformal surface that is similar to the bearing surface. The final insert 3602 is a permanent or quasi-permanent member of the joint prosthesis that provides long term post-operative sensing of the joint. Quasi-permanent refers to the fact that insert 3602 has a wear surface that has a finite life time that could need replacing depending on a number of factors such as life style, physical shape, and length of use. Final insert 3602 replaces a passive insert that has no sensing capability. In one embodiment, an external charging device proximally located to the knee prosthetics can inductively charge the sensing module 3604. A super capacitor is charged in sensing module 3604 that powers the sensor and circuitry to perform the one or more measurements. Alternatively, a battery or other temporary energy storage device can be used to power sensing module 3604 and be charged with the external charging device.

Figure 37:
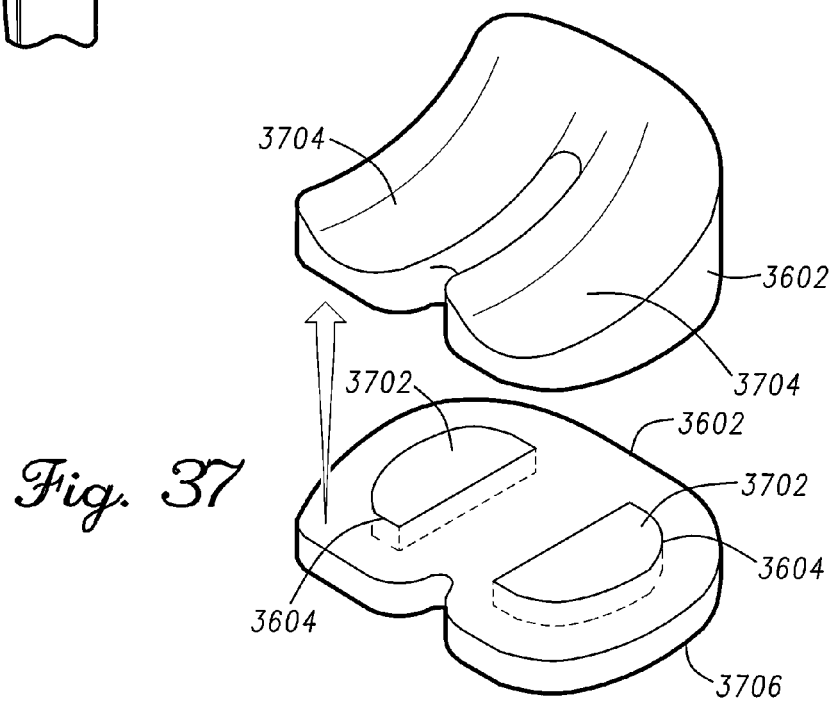
FIG. 37 is a perspective view of sensing modules in final insert in accordance with an exemplary embodiment.

FIG. 37 is a perspective view of sensing modules 3604 in final insert 3602 in accordance with an exemplary embodiment. Final insert 3602 is shown being separated in two halves via a horizontal cut to show sensing modules 3604. Final insert 3602 is used in a total knee reconstruction where both knee compartments are replaced. A single sensing module 3604 would be used for a partial reconstruction. Bearing surfaces 3704 couple to a femoral prosthetic component (not shown) such that the articulating surfaces allow movement of the muscular-skeletal system. In the example, a bottom surface 3706 of the final insert 3602 aligns and couples to a tibial prosthetic component. In the example, the bottom surface 3706 is a support surface that retains insert 3602 in a fixed position relative to a mechanical axis of the leg. Furthermore, the bottom surface 3706 and a surface of the tibial prosthetic component are non-articulating.

Sensing modules 3604 underlie bearing surfaces 3704. A parameter of the muscular-skeletal system is applied to the bearing surface 3704 and couples through the material of final insert 3602 to contacting surfaces 3702 of sensing modules 3604. The bearing surfaces 3704 are typically a high strength polymer such as ultra high molecular weight polyethylene. In a non-limiting example, a force, pressure, or load is the parameter measured by sensing module 3604. Sensing module 3604 can measure parameter magnitude and the location where the parameter is applied. Sensing module 3604 can have a surface that mirrors or replicates the surface of bearing surfaces 3704.

In one embodiment, the final insert 3602 can be precision molded in two or more pieces that allow the positioning and insertion of sensing module 3604. As shown, the final insert is formed in two halves. The upper half includes the bearing surfaces 3704. The insert can be formed of a composite material. The composite material will at least include the bearing surface material and a second material that is attached or bonded together. A cavity is formed in predetermined locations that receive sensing modules 3604. The cavities correspond to bearing surfaces 3604 for each compartment of the knee. The sensing modules 3604 are placed in each cavity. The halves of final insert 3602 are then fastened together whereby the contacting surface 3702 operatively couples to a corresponding bearing surface 3704. The contact surfaces 3702 have a relational position to bearing surfaces 3604 allowing position detection where the parameter is applied. The halves of final insert 3602 can be mechanically fastened, attached by adhesive, thermally bonded, or connected by other method such that halves will not separate under all operating conditions. The fastening process can also form a seal that isolates sensing modules 3604 from the external environment.

Figure 38:
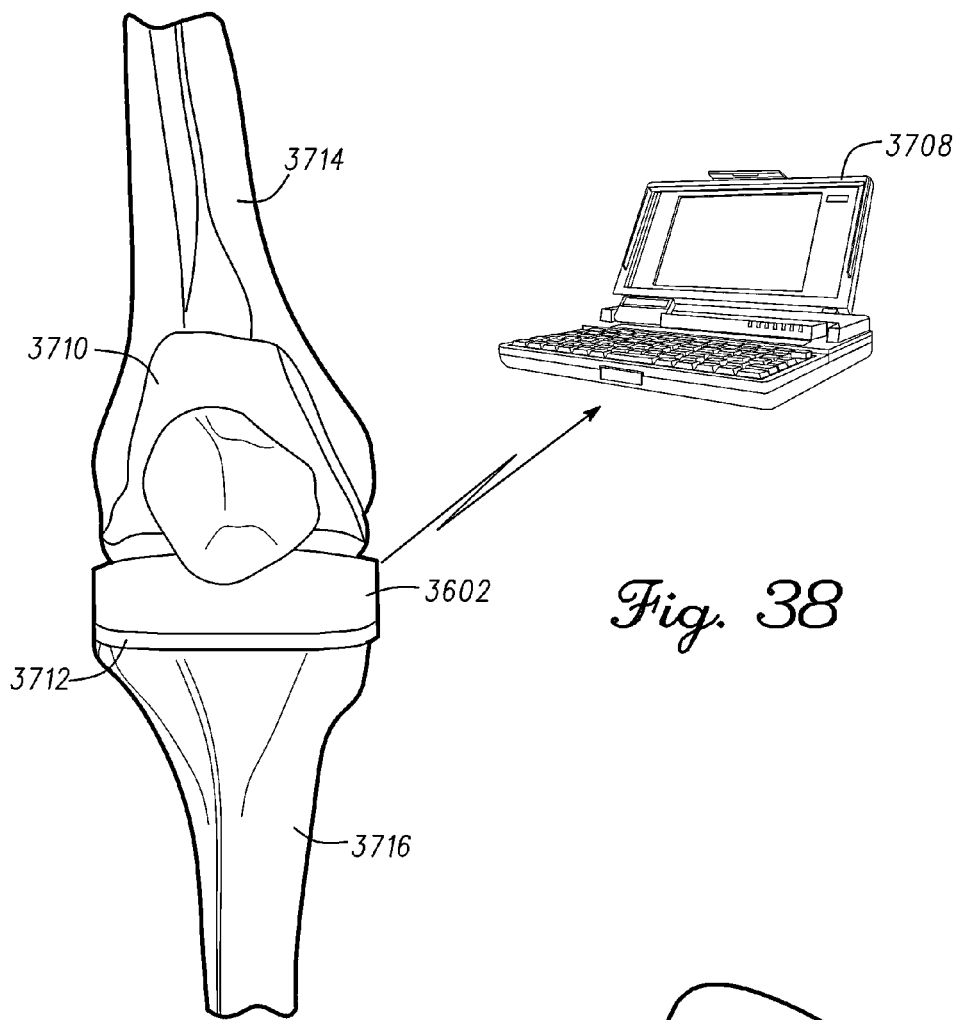
FIG. 38 is an illustration of the final insert installed in a knee in accordance with an exemplary embodiment.

FIG. 38 is an illustration of the final insert 3602 installed in a knee in accordance with an exemplary embodiment. In the example, a femoral prosthetic component 3710 is coupled to a prepared 3714 femur. Similarly, a tibial prosthetic component 3712 is coupled to a prepared tibia 3716. The preparation includes alignment of the prosthetic components to a mechanical axis. The insert 3602 is placed between the tibial prosthetic component 3712 and femoral prosthetic component 3710. In general, the insert 3602 is substantially equivalent in dimensions to a passive final insert. The artificial condyles of femoral prosthetic component 3710 articulate with a bearing surface of final insert 3602 that allows movement of the leg.

As disclosed above, final insert 3602 includes a sensing module that can transmit data to a processor 3708. The processor can be in a tool, equipment, computer, display, or other device. As shown, the processor is in a notebook computer. Receiver circuitry is coupled to processor 3708 that can communicate with the sensing module. Typically, the receiver circuitry is placed in close proximity to final insert 3602 to receive the short-range transmission. In one embodiment, the sensing module can only transmit data. In a second embodiment, the sensing module can have two-way communication between the sensing module and processor 3708.

The loading, balance, and position can be adjusted during surgery within predetermined quantitatively measured ranges through surgical techniques and adjustments using data from a trial insert and final insert 3602. Both the trial and final inserts include the sensing module to provide measured data to processor 3708 for display. The final insert 3602 is also used to monitor the reconstructed joint long term. The data can be used by the patient and health care providers to ensure that the joint is functioning properly during rehabilitation and as the patient returns to an active normal lifestyle. Conversely, the patient or health care provider is notified when the measured parameters are out of specification. This provides early detection of a problem that can be resolved with minimal stress to the patient. The data from final insert 3602 can be displayed on a screen in real time using data from the embedded sensing module. In one embodiment, a handheld device is used to receive data from final insert 3602. The handheld device can be held in proximity to the knee allowing a strong signal to be obtained for reception of the data.

In general, final insert 3602 is an example of a sensor system that can be integrated into prosthetic components. The form factor of the sensing assemblages, layout architecture, electronic circuitry, and housing allow it to fit in one or more prosthetic components. Moreover, it is a self-contained device that performs measurements without extraneous devices. The sensing module can also be placed in femoral prosthetic component 3710 or tibial prosthetic component 3712 to measure a parameter of interest. Data generated by the device can be sent to a database for analysis.

Artificial components for other joint replacement surgeries have a similar operational form as the knee joint example. The joint typically comprises two or more bones with a cartilaginous surface as a bearing surface that allows joint movement. The cartilage also acts to absorb loading on the joint and prevents bone-to-bone contact. Reconstruction of the hip, spine, shoulder, and other joints has similar functioning insert structures having at least one bearing surface. Like the knee joint, these other insert structures typically comprise a polymer material. The polymer material is formed for a particular joint structure. For example, the hip insert is formed in a cup shape that is fitted into the pelvis. In general, the size and thickness of these other joint inserts allow the integration of the sensing module. It should be noted that the sensing module disclosed herein contemplates use in both trial inserts and permanent inserts for the other joints of the muscular-skeletal system thereby providing quantitative parameter measurements during and post surgery.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the invention.

What is claimed is:

1. A sensing module for measuring a force, pressure, or load applied by the muscular-skeletal system comprising:
a first surface for coupling to the muscular-skeletal system where the first surface includes a predetermined area comprising a polygon;
a second surface; and
at least three force sensors coupled between the first and second surfaces where each sensor underlies a vertex of the polygon, where the sensing module is configured to measure the force, pressure, or load applied by the muscular-skeletal system, and where the sensing module is configured to identify a position of applied load on the first surface.

2. The sensing module of claim 1 further including:
electronic circuitry coupled to the at least three force sensors:
a transmitter coupled to the electronic circuitry configured to transmit sensor data; and
a power source configured to power the electronic circuitry and transmitter.

3. The sensing module of claim 2 further includes an encapsulating enclosure to house the electronic circuitry, transmitter, power source, and the at least three force sensors.

4. The sensing module of claim 3 where the polygon is a triangle.

5. The sensing module of claim 4 further including a flexible interconnect coupling the electronic circuitry to the at least three force sensors.

6. The sensing module of claim 5 further including a remote system configured to receive and display data from the sensing module.

7. The sensing module of claim further including a structure configured to distribute loading applied to the first surface to the at least three force sensors.

8. The sensing module of claim 7 where the first surface is configured to move under a force.

9. The sensing module of claim 8 were the at least three force sensors are plezo-resistive sensors.

10. The sensing module of claim where the electronic circuitry underlies the at least three force sensors.

11. A sensing module for measuring a force, pressure, or load applied by the muscular-skeletal system comprising:
a first surface for coupling to the muscular-skeletal system where the first surface includes a predetermined area comprising a polygon;
a second surface;
at least three force sensors coupled between the first and second surfaces where each sensor underlies a vertex of the polygon, where the sensing module is configured to measure a force applied by the muscular-skeletal system to the first surface, and where the sensing module is configured to identify a position of applied load on the first surface; and
at least one structure to distribute loading coupled between the first surface and the at least three force.

12. The sensing module of claim 11 where the sensing module is configured to measure a force applied by the muscular-skeletal system within the predetermined area and where the sensing module is configured to identify the position of applied load within the predetermined area.

13. The sensing module of claim 12 where the polygon is a triangle.

14. The sensing module of claim 13 where the sensing module is an insert prosthetic component further comprising;
electronic circuitry coupled to the at least three force sensors;
a transmitter coupled to the electronic circuitry configured to transmit sensor data; and
a power source configured to power the electronic circuitry and transmitter.

15. The sensing module of claim 14 where the electronic circuitry, transmitter, power source, and at least three force sensors are housed in the insert prosthetic component and isolated from an external environment.

16. The sensing module of claim 15 where the first surface is an articular surface.

17. The sensing module of claim 16 where the sensing module is configured to send data such that the force and position of applied load is displayed on a remote system in real time and where the at least three force sensors comprises one of a piezo-resistive sensor, MEMS sensor, strain gauge, or mechanical sensor.

18. A sensing module for measuring a force applied by the muscular-skeletal system comprising:
a first surface for coupling to the muscular-skeletal system where the first surface includes a predetermined area comprising a polygon;
a second surface; and
at least three piezo-resistive sensors coupled between the first and second surfaces where each sensor underlies a vertex of the polygon, where the sensing module is configured to measure the force applied by the muscular-skeletal system, and where the sensing module is configured to identify a position of applied load on the first surface.

19. The sensing module of claim 18 where the sensing module is configured to measure a force applied by the muscular-skeletal system within the predetermined area and where the sensing module is configured to identify the position of applied load within the predetermined area.

20. The sensing module of claim 19 where at least one structure to distribute loading is coupled between the first surface and the at least three piezo-resistive sensors.

\* \* \* \* \*